United States Patent
Buggy et al.

(10) Patent No.: US 9,371,281 B2
(45) Date of Patent: *Jun. 21, 2016

(54) INDOLE DERIVATIVES AS INHIBITORS OF HISTONE DEACETYLASE

(71) Applicant: Pharmacyclics LLC, Sunnyvale, CA (US)

(72) Inventors: Joseph J. Buggy, Mountain View, CA (US); Sriram Balasubramanian, San Carlos, CA (US); Erik Verner, San Mateo, CA (US); Vincent W. F. Tai, San Mateo, CA (US); Chang-Sun Lee, Belle Mead, NJ (US)

(73) Assignee: Pharmacyclics LLC, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/527,666

(22) Filed: Oct. 29, 2014

(65) Prior Publication Data

US 2015/0299119 A1    Oct. 22, 2015

Related U.S. Application Data

(60) Continuation of application No. 13/683,880, filed on Nov. 21, 2012, now Pat. No. 8,900,565, which is a division of application No. 11/687,565, filed on Mar. 16, 2007, now Pat. No. 8,338,416.

(60) Provisional application No. 60/783,287, filed on Mar. 16, 2006.

(51) Int. Cl.

| | |
|---|---|
| *A61K 45/06* | (2006.01) |
| *C07D 209/08* | (2006.01) |
| *C07D 209/12* | (2006.01) |
| *C07D 209/14* | (2006.01) |
| *C07D 209/42* | (2006.01) |
| *C07D 403/06* | (2006.01) |
| *A61K 31/404* | (2006.01) |
| *A61K 31/5377* | (2006.01) |

(52) U.S. Cl.
CPC ............ *C07D 209/08* (2013.01); *A61K 31/404* (2013.01); *A61K 31/5377* (2013.01); *A61K 45/06* (2013.01); *C07D 209/12* (2013.01); *C07D 209/14* (2013.01); *C07D 209/42* (2013.01); *C07D 403/06* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,399,559 A * | 3/1995 | Curtze | ................... | A01N 43/38 514/235.2 |
| 6,069,156 A | 5/2000 | Oku et al. | | |
| 6,303,600 B1 * | 10/2001 | Cox | ...................... | C07D 209/12 514/235.5 |
| 8,338,416 B2 * | 12/2012 | Buggy | ................... | A61K 45/06 514/235.2 |
| 8,896,769 B2 | 11/2014 | Huang et al. | | |
| 8,900,565 B2 | 12/2014 | Buggy et al. | | |
| 2007/0043057 A1 * | 2/2007 | Matteucci | ............ | C07D 209/42 514/252.04 |
| 2010/0190768 A1 * | 7/2010 | Sone | .................... | C07D 209/12 514/210.21 |

FOREIGN PATENT DOCUMENTS

| | | |
|---|---|---|
| WO | WO-02-055017 | 7/2002 |
| WO | WO-03-013493 | 2/2003 |
| WO | WO-2007-048841 | 5/2007 |
| WO | WO-2008-060721 | 5/2008 |
| WO | WO-2008-061160 | 5/2008 |

OTHER PUBLICATIONS

Balasubramanian et al. Caplus an 2005:580843 (2008).
Bhalla. Epigenetic and Chromatin Modifiers as Targeted Therapy of Hematologic Malignancies. J. Clin. Oncol. 23:3971-3993 (2005).
Buggy et al. Cloning and characteristics of a novel human histone deacetylase, HDAC8. Biochem. J. 350 Pt. 1:199-205 (2000).
Carta et al. Histone deacetylase inhibitors prevent exocytosis of interleukin- 1β-containing secretory lysosomes: role of microtubules. Blood 108(5):1618-1626 (2006).
Chawla et al. Challenges in Polymorphism of Pharmaceuticals. CRIPS; 5(1):9-12 (Jan.-Mar. 2004).
Fuino et al. Histone deacetylase inhibitor LAQ824 down-regulates Her-2 and sensitizes human breast cancer cells to trastuzumab, taxotere, gemcitibine, and epothilone B, Mol. Cancer Ther. 2:971-984 (2003).
Jacobs et al. Substituted 3-(Phenylmethyl)-1 H-indole-5-carboxamides and 1-(Phenylmethyl)indole-6-carboxamides as Potent, Selective, Orally Active Antagonists of the Peptidoleukotrienes. J. Med. Chem. 36:394-409 (1993).
Leoni et al. The antitumor histone deacetylase inhibitor suberoylanilide hydroxamic acid exhibits antiinflammatory properties via suppression of cytokines. PNAS USA 99:2995-3000 (2002).
Leukemia. 2013. http://my.clevelandclinic.org/leukemia/hic_leukemia.aspx.
Lymphoma. 2013. http://www.uptodate.com/contents/treatment-and-prognosis-of-adult-t-cell-leukemia-lymphma?topicKey=HEME%2F4736&rlapsedTimeMs=1&view=print&displayedView=full.
Miller et al. Histone deacetylase inhibitors. J. Med. Chem. 46(24):5097-5116 (2003).
Newman et al. Solid-State Analysis of the Active Pharmaceutical Ingredient in Drug Products. DDT 8(19):898-905 (Oct. 2003).
PCT/US2007/06714 International Preliminary Report on Patentability dated Sep. 16, 2008.

(Continued)

Primary Examiner — Sun Jae Yoo
(74) Attorney, Agent, or Firm — Foley Hoag LLP

(57) ABSTRACT

Described herein are compounds and pharmaceutical compositions containing such compounds, which inhibit the activity of histone deacetylase 8 (HDAC8). Also described herein are methods of using such HDAC8 inhibitors, alone and in combination with other compounds, for treating diseases or conditions that would benefit from inhibition of HDAC8 activity.

21 Claims, 18 Drawing Sheets

(56) References Cited

OTHER PUBLICATIONS

PCT/US2007/06714 International Search Report dated May 27, 2008.
Somoza et al. Structural Snapshots of Human HDAC8 Provide Insights into the Class 1 Histone Deacytelases. Structure 12:1325-1334 (2004).
U.S. Appl. No. 11/687,565 Office Action dated Aug. 9, 2010.
U.S. Appl. No. 11/687,565 Office Action dated Jan. 27, 2010.
U.S. Appl. No. 11/687,565 Office Action dated May 19, 2009.
U.S. Appl. No. 11/687,565 Office Action dated Nov. 10, 2010.
U.S. Appl. No. 13/683,880 Office Action dated Aug. 2, 2013.
U.S. Appl. No. 13/683,880 Office Action dated Jan. 16, 2014.
Vannini et al. Crystal structure of a eukaryotic zinc-dependent histone deacetylase, human HDAC8, complexed with a hydroxamic acid inhibitor. PNAS 101(42):15064-15069 (2004).
Yoo et al. Epigenetic therapy of cancer: past, present and future. Nat. Rev. Drug Discov. 5:37-50 (2006).

\* cited by examiner

INDOLE DERIVATIVES AS INHIBITORS OF HISTONE DEACETYLASE

RELATED APPLICATIONS

This application is a continuation of U.S. application Ser. No. 13/683,880, filed Nov. 21, 2012, which is divisional of U.S. application Ser. No. 11/687,565, filed on Mar. 16, 2007, now issued as U.S. Pat. No. 8,338,416 on Dec. 25, 2012, which claims priority from U.S. Provisional Application No. 60/783,287, filed Mar. 16, 2006, all of which are incorporated herein by reference in their entireties.

FIELD OF THE INVENTION

Described herein are compounds, methods of making such compounds, pharmaceutical compositions and medicaments that include such compounds, and methods of using such compounds to inhibit the activity of histone deacetylase.

BACKGROUND OF THE INVENTION

Histone deacetylases (HDACs) catalyze the removal of acetyl groups from histones, proteins that organize and modulate the structure of chromatin in nucleosomes. HDAC-mediated deacetylation of chromatin-bound histones regulates the expression of a variety of genes throughout the genome. Importantly, HDACs have been linked to cancer, as well as other health conditions. To date, eleven major HDAC isoforms have been described (HDACs 1-11). HDACs are categorized into two classes. Class I HDACs include HDAC1, HDAC2, HDAC3, HDAC8 and HDAC11. Class II HDACs include HDAC4, HDAC5, HDAC6, HDAC7, HDAC9 and HDAC10. Small molecule HDAC inhibitors that are isoform-selective are useful as therapeutic agents with reduced toxicity and as tools for probing the biology of the HDAC isoforms.

SUMMARY OF THE INVENTION

In one aspect provided herein are indole-6-carboxylic acid hydroxyamide compounds and indole-5-carboxylic acid hydroxyamide compounds, pharmaceutically acceptable salts, pharmaceutically acceptable N-oxides, pharmaceutically active metabolites, pharmaceutically acceptable prodrugs, and pharmaceutically acceptable solvates thereof, which selectively inhibit HDAC8 activity and may be used to treat patients where inhibition of HDAC8 activity would provide benefit. Compounds described herein are selective HDAC8 inhibitors.

Described herein are compounds, compositions and methods for selectively inhibiting HDAC8 activity. In one embodiment, described herein are indole-6-carboxylic acid hydroxyamide compounds and indole-5-carboxylic acid hydroxyamide compounds that are selective HDAC8 inhibitors.

In one embodiment, described herein is a 1,3-disubstituted-1H-indole-6-carboxylic acid hydroxyamide compound, wherein the substituent at the 1-position is $-X^2-R^2$ and the substituent at the 3-position is $R^3$, wherein:

$X^2$ is a bond, or a substituted or unsubstituted group selected from among $C_1$-$C_6$alkylene, $C_2$-$C_6$alkenylene, $C_2$-$C_6$ alkynylene, $C_1$-$C_6$fluoroalkylene, $C_2$-$C_6$fluoroalkenylene, $C_1$-$C_6$haloalkylene, $C_2$-$C_6$haloalkenylene, $C_1$-$C_6$heteroalkylene; $-C(=O)-$, and $-C(=O)-C_1$-$C_6$alkylene;

$R^2$ is a substituted or unsubstituted group selected from among aryl, heteroaryl, cycloalkyl, and heterocycloalkyl;

where if $R^2$ is substituted, then each substituent on $R^2$ is selected from among hydrogen, halogen, $-CN$, $-NO_2$, $-S(=O)_2NH_2$, $-CO_2H$, $-CO_2R^{10}$, $-C(=O)R^{11}$, $-S-R^{11}$, $-S(=O)-R^{11}$, $-S(=O)_2-R^{11}$, $-NR^{10}C(=O)-R^{11}$, $-C(=O)N(R^{10})_2$, $-S(=O)_2N(R^{10})_2$, $-NR^{10}S(=O)_2-R^{11}$, $-OC(=O)N(R^{10})_2$, $-NR^{10}C(=O)O-R^{11}$, $-OC(=O)O-R^{11}$, $-NHC(=O)NH-R^{11}$, $-OC(=O)-R^{11}$; $-N(R^{10})_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl;

$R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, aryl, and heteroaryl;

$R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;

$R^3$ is hydrogen, halogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, or $-X^6-R^6$;

$X^6$ is a $C_1$-$C_6$alkylene, $C_1$-$C_6$fluoroalkylene, $C_2$-$C_6$alkenylene, $C_2$-$C_6$heteroalkylene;

$R^6$ is hydrogen, halogen, $-CN$, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl, phenyl, heteroaryl, or $-X^7-R^7$;

$X^7$ is a bond, $-O-$, $-S-$, $-S(=O)-$, $-S(=O)_2-$, $-NR^a-$, $-C(=O)-$, $-C(=O)O-$, $-OC(=O)-$, $-NHC(=O)-$, $-C(=O)NR^a-$, $-S(=O)_2NR^a-$, $-NHS(=O)_2-$, $-OC(=O)NR^a-$, $-NHC(=O)O-$, $-OC(=O)O-$, $-NHC(=O)NR^a-$;

$R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl, $R^a$ is selected from among hydrogen, $C_1$-$C_6$alkyl, $C_2$-$C_6$alkenyl, hydroxy, $C_1$-$C_6$alkoxy, $C_1$-$C_6$fluoroalkoxy, $C_1$-$C_6$heteroalkyl; or $R^a$ and $R^7$ together with the N atom to which they are attached form a 5-, 6-, or 7-membered heterocycloalkyl;

or an active metabolite, pharmaceutically acceptable solvate, pharmaceutically acceptable salt, pharmaceutically acceptable N-oxide, or pharmaceutically acceptable prodrug thereof.

For any and all of the embodiments, substituents can be selected from among from a subset of the listed alternatives. For example, in some embodiments, $X^2$ is a substituted or unsubstituted group selected from among $C_1$-$C_6$alkylene, $C_2$-$C_6$alkenylene, $C_1$-$C_6$fluoroalkylene, $C_2$-$C_6$fluoroalkenylene, and $C_1$-$C_6$heteroalkylene. In other embodiments, $X^2$ is a substituted or unsubstituted group selected from among $C_1$-$C_6$alkylene, and $C_2$-$C_6$alkenylene.

In some embodiments, $R^2$ is an optionally substituted group selected from among phenyl, naphthyl, monocyclic heteroaryl, bicyclic heteroaryl, $C_3$-$C_8$ cycloalkyl, monocyclic heterocycloalkyl, and bicyclic heterocycloalkyl. In other embodiments, $R^2$ is an optionally substituted group selected from among phenyl, naphthyl, (monocyclic heteroaryl containing 0-2 N atoms, 0-1 O atoms, and 0-1 S atoms), (bicyclic heteroaryl containing 0-2 N atoms, 0-1 O atoms, and 0-1 S atoms), $C_3$-$C_8$ cycloalkyl, monocyclic heterocycloalkyl containing 0-2 N atoms, and bicyclic heterocycloalkyl 0-2 N atoms; where if $R^2$ is substituted, then each substituent on $R^2$ is selected from among hydrogen, halogen, —CN, —NO$_2$, —S(=O)$_2$NH$_2$, —CO$_2$H, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —NR$^{10}$S(=)$_2$—R$^{11}$, —OC(=O)—R$^{11}$; —N(R$^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl; $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, phenyl, and heteroaryl; $R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, phenyl, and heteroaryl.

In some embodiments, $R^2$ is an optionally substituted group selected from among phenyl, naphthyl, (monocyclic heteroaryl containing 0-2 N atoms, 0-1 O atoms, and 0-1 S atoms), (bicyclic heteroaryl containing 0-2 N atoms, 0-1 O atoms, and 0-1 S atoms), $C_3$-$C_8$ cycloalkyl; where if $R^2$ is substituted, then each substituent on $R^2$ is selected from among hydrogen, halogen, —CN, —NO$_2$, —S(=O)$_2$NH$_2$, —CO$_2$H, —CO$_2$R$^{10}$, —C(=O)R$^{11}$, —S—R$^{11}$, —S(=O)—R$^{11}$, —S(=O)$_2$—R$^{11}$, —NR$^1$C(=O)—R$^{11}$, —C(=O)N(R$^{10}$)$_2$, —S(=O)$_2$N(R$^{10}$)$_2$, —NR$^{10}$S(=O)$_2$—R$^{11}$, —OC(=O)—R$^{11}$; —N(R$^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl; $R^{10}$ is hydrogen, or a substituted or unsubstituted group selected from among $C_1$-$C_6$alkyl, $C_1$-$C_6$fluoroalkyl, $C_1$-$C_6$heteroalkyl, and phenyl; $R^{11}$ is a substituted or unsubstituted group selected from among $C_1$-$C_6$alkyl, $C_1$-$C_6$fluoroalkyl, and phenyl.

In some embodiments, $R^3$ is hydrogen, halogen, substituted or unsubstituted $C_1$-$C_6$alkyl, substituted or unsubstituted $C_2$-$C_6$alkenyl, substituted or unsubstituted $C_1$-$C_6$heteroalkyl, substituted or unsubstituted phenyl, or —X$^6$—R$^6$; X$^6$ is a $C_1$-$C_6$alkylene, $C_1$-$C_6$fluoroalkylene, $C_2$-$C_6$alkenylene, or $C_2$-$C_6$heteroalkylene; $R^6$ is hydrogen, halogen, —CN, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl, phenyl, heteroaryl, or —X$^7$—R$^7$; X$^7$ is a bond, —O—, —S—, —S(=O)—, —S(=O)$_2$—, —NR$^a$—, —C(=O)—, —C(=O)O—, —OC(=O)—, —NHC(=O)—, —C(=O)NR$^a$—, —S(=O)$_2$NR$^a$—, —NHS(=O)$_2$—, —OC(=O)NR$^a$—, —NHC(=O)O—, —OC(=O)O—, —NHC(=O)NR$^a$—; $R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl; $R^a$ is selected from among hydrogen, $C_1$-$C_6$alkyl, $C_2$-$C_6$alkenyl, hydroxy, $C_1$-$C_6$alkoxy, $C_1$-$C_6$fluoroalkoxy, $C_1$-$C_6$heteroalkyl; or $R^a$ and $R^7$ together with the N atom to which they are attached form a 5-, 6-, or 7-membered heterocycloalkyl.

In some embodiments, $R^3$ is hydrogen, halogen, substituted or unsubstituted $C_1$-$C_6$alkyl, or —X$^6$—R$^6$.

In some embodiments, $X^6$ is $C_1$-$C_6$alkylene; $R^6$ is hydrogen, halogen, —CN, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl containing 0-2 N atoms, phenyl, heteroaryl containing 0-2 N atoms, or —X$^7$—R$^7$; X$^7$ is a bond, —O—, —S—, —S(=O)—, —S(=O)$_2$—, —NR$^a$—, —C(=O)—, —C(=O)O—, —OC(=O)—, —NHC(=O)—, —C(=O)NR$^a$—, —S(=O)$_2$NR$^a$—, —NHS(=O)$_2$—; $R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl; $R^a$ is selected from among hydrogen, $C_1$-$C_6$alkyl, $C_2$-$C_6$alkenyl, hydroxy, $C_1$-$C_6$alkoxy, $C_1$-$C_6$fluoroalkoxy, $C_1$-$C_6$heteroalkyl; or $R^a$ and $R^7$ together with the N atom to which they are attached form a 5-, 6-, or 7-membered heterocycloalkyl.

In some embodiments, $R^6$ is —X$^7$—R$^7$.

In some embodiments, $X^7$ is a bond, —O—, —S—, —S(=O)—, —S(=O)$_2$—, —NR$^a$—, or —C(=O)—.

In some embodiments, $R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, phenyl, phenylC$_1$-$C_4$alkyl, heteroaryl, heteroarylC$_1$-$C_4$alkyl; $R^a$ is selected from among hydrogen, $C_1$-$C_6$alkyl, hydroxy, $C_1$-$C_6$alkoxy, $C_1$-$C_6$fluoroalkoxy, $C_1$-$C_6$heteroalkyl; or $R^a$ and $R^7$ together with the N atom to which they are attached form a 5-, or 6-membered heterocycloalkyl.

In some embodiments, $X^7$ is a bond, —O—, or —NR$^a$—. In some embodiments, $X^7$ is a bond, or —NR$^a$—.

In some embodiments, $R^a$ is selected from among hydrogen, $C_1$-$C_6$alkyl, hydroxy, $C_1$-$C_6$alkoxy, $C_1$-$C_6$heteroalkyl. In other embodiments, $R^a$ is selected from among hydrogen, $C_1$-$C_6$alkyl, and $C_1$-$C_6$heteroalkyl.

In some embodiments, $R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, phenyl, phenylC$_1$-$C_4$alkyl, heteroaryl, heteroarylC$_1$-$C_4$alkyl; $R^a$ is selected from among hydrogen, $C_1$-$C_6$alkyl, hydroxy, $C_1$-$C_6$alkoxy, $C_1$-$C_6$heteroalkyl; or $R^a$ and $R^7$ together with the N atom to which they are attached form a 5-, or 6-membered heterocycloalkyl.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In one embodiment, provided herein is a compound selected from among: 1-(3,4-dichloro-phenylmethyl)-1H-indole-6-carboxylic acid hydroxyamide (Compound 1); 1-(2-methyl-phenylmethyl)-1H-indole-6-carboxylic acid hydroxyamide (Compound 2); 1-(3,4,5-trimethoxy-phenylmethyl)-1H-indole-6-carboxylic acid hydroxyamide (Compound 3); 1-(3-fluoro-phenylmethyl)-1H-indole-6-carboxylic acid hydroxyamide (Compound 4); 1-(3-methyl-phenylmethyl)-1H-indole-6-carboxylic acid hydroxyamide (Compound 5); 1-(benzyl)-1H-indole-6-carboxylic acid hydroxyamide (Compound 6); 1-(3,5-dimethoxy-phenylmethyl)-1H-indole-6-carboxylic acid hydroxyamide (Compound 7); 1-(1-methyl-1-phenylmethyl)-1H-indole-6-carboxylic acid hydroxyamide (Compound 8); 1-(4-fluoro-phenylmethyl)-1H-indole-6-carboxylic acid hydroxyamide (Compound 9); 1-(2-fluoro-phenylmethyl)-1H-indole-6-carboxylic acid hydroxyamide (Compound 10); 1-(2-chloro-phenylmethyl)-1H-indole-6-carboxylic acid hydroxyamide (Compound 11); 1-(3-methoxy-phenylmethyl)-1H-indole-6-carboxylic acid hydroxyamide (Compound 12); 1-(naphth-2-ylmethyl)-1H-indole-6-carboxylic acid hydroxyamide (Compound 13); 1-(3-phenylpropyl)-1H-indole-6-carboxylic acid hydroxyamide (Compound 14); 1-(cyclohexylmethyl)-1H-indole-6-carboxylic acid hydroxyamide (Compound 15); 1-[1-(phenyl)-propen-3-yl]-1H-indole-6-carboxylic acid hydroxyamide (Compound 16); 1-[4-(trifluoromethoxy)-phenylmethyl]-1H-indole-6-carboxylic acid hydroxyamide (Compound 17); 1-(4-chloro-phenylmethyl)-1H-indole-6-carboxylic acid hydroxyamide (Compound 18); 1-(benzo[2,1,3]oxadiazol-5-ylmethyl)-1H-indole-6-carboxylic acid hydroxyamide (Compound 19; 1-(4-methyl-phenylmethyl)-1H-indole-6-carboxylic acid hydroxyamide (Compound 20); 1-(3-fluoro-4-methoxy-phenylmethyl)-1H-indole-6-carboxylic acid hydroxyamide (Compound 21); 1-[4-(difluoromethoxy)-phenylmethyl]-1H-indole-6-carboxylic acid hydroxyamide (Compound 22); 1-(4-methoxy-phenylmethyl)-1H-indole-6-carboxylic acid hydroxyamide (Compound 23); 1-(phenethyl)-1H-indole-6-carboxylic acid hydroxyamide (Compound 24); 1-(3-chloro-phenylmethyl)-1H-indole-6-carboxylic acid hydroxyamide (Compound 25); 1-[N-(t-butoxycarbonyl)piperidin-4-ylmethyl]-1H-indole-6-carboxylic acid hydroxyamide (Compound 26); 1-(piperidin-4-ylmethyl)-1H-indole-6-carboxylic acid hydroxyamide (Compound 27); 1-(N-methylsulfonyl-3-aminobenzyl)-1H-indole-6-carboxylic acid hydroxyamide (Compound 28); 3-(Dimethylaminomethyl)-1-(4-methoxybenzyl)-1H-indole-6-carboxylic acid hydroxyamide (Compound 29); 3-(N-Morpholinomethyl)-1-(4-methoxybenzyl)-1H-indole-6-carboxylic acid hydroxyamide (Compound 30); 3-(N-Pyrrolidinomethyl)-1-(4-methoxybenzyl)-1H-indole-6-carboxylic acid hydroxyamide (Compound 31); 3-(N-Benzylaminomethyl)-1-(4-methoxybenzyl)-1H-indole-6-carboxylic acid hydroxyamide (Compound 32); and 3-(Ethyl)-1-(4-methoxybenzyl)-1H-indole-6-carboxylic acid hydroxyamide (Compound 33).

Compounds described herein are selective histone deacetylase 8 (HDAC8) inhibitors. In one embodiment, the selective HDAC8 inhibitor has an $IC_{50}$ for histone deacetylase 8 activity that is at least 10 fold lower than the $IC_{50}$ of histone deacetylase 1, histone deacetylase 2, histone deacetylase 3, histone deacetylase 6, histone deacetylase 10, or histone deacetylase 11.

In one embodiment, provided herein is a 1,3-disubstituted-1H-indole-5-carboxylic acid hydroxyamide compound, wherein the substituent at the 1-position is $R^4$ and the substituent at the 3-position is $-X^5-R^5$, wherein:

$R^4$ is hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, or $-X-R^8$;

$X^8$ is a $C_2$-$C_6$alkylene, $C_2$-$C_6$fluoroalkylene, $C_2$-$C_6$alkenylene, or $C_2$-$C_6$heteroalkylene;

$R^8$ is hydrogen, halogen, —CN, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl, phenyl, heteroaryl, or $-X^9-R^9$;

$X^9$ is a bond, —O—, —S—, —S(=O)—, —S(=O)$_2$—, —NR$^a$—, —C(=O)—, —C(=O)O—, —OC(=O)—, —NHC(=O)—, —C(=O)NR$^a$—, —S(=O)$_2$NR$^a$—, —NHS(=O)$_2$—, —OC(=O)NR$^a$—, —NHC(=O)O—, —OC(=O)O—, —NHC(=O)NR$^a$—;

$R^9$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl, $R^a$ is selected from among hydrogen, $C_1$-$C_6$alkyl, $C_2$-$C_6$alkenyl, hydroxy, $C_1$-$C_6$alkoxy, $C_1$-$C_6$fluoroalkoxy, $C_1$-$C_6$heteroalkyl; or $R^a$ and $R^9$ together with the N atom to which they are attached form a 5-, 6-, or 7-membered heterocycloalkyl;

$X^5$ is a bond, or a substituted or unsubstituted group selected from among $C_1$-$C_6$alkylene, $C_2$-$C_6$alkenylene, $C_2$-$C_6$alkynylene, $C_1$-$C_6$fluoroalkylene, $C_2$-$C_6$fluoroalkenylene, $C_1$-$C_6$haloalkylene, $C_2$-$C_6$haloalkenylene, $C_1$-$C_6$heteroalkylene, —C(=O)—, and —C(=O)—$C_1$-$C_6$alkylene;

$R^5$ is a substituted or unsubstituted group selected from among aryl, heteroaryl, $C_3$-$C_8$cycloalkyl, and heterocycloalkyl;

where if $R^5$ is substituted, then each substituent on $R^5$ is selected from among hydrogen, halogen, —CN, —NO$_2$, —S(=O)$_2$NH$_2$, —CO$_2$H, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —NR$^{10}$S(=O)$_2$—R$^{11}$, —OC(=O)N(R$^{10}$)$_2$, —NR$^{10}$C(=O)O—R$^{11}$, —OC(=O)O—R$^{11}$, —NHC(=O)NH—R$^{11}$, —OC(=O)—R$^{11}$; —N(R$^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl;

$R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, aryl, and heteroaryl;

$R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;

or an active metabolite, pharmaceutically acceptable solvate, pharmaceutically acceptable salt, pharmaceutically acceptable N-oxide, or pharmaceutically acceptable prodrug thereof.

For any and all of the embodiments, substituents can be selected from among from a subset of the listed alternatives. For example, in some embodiments, $R^4$ is hydrogen, substituted or unsubstituted $C_1$-$C_6$alkyl, substituted or unsubstituted $C_2$-$C_6$alkenyl, substituted or unsubstituted $C_1$-$C_6$alkoxy, substituted or unsubstituted $C_1$-$C_6$heteroalkyl, substituted or unsubstituted phenyl, or —X—$R^8$; $X^8$ is a $C_2$-$C_6$alkylene, $C_2$-$C_6$fluoroalkylene, $C_2$-$C_6$alkenylene, or $C_2$-$C_6$heteroalkylene; $R^8$ is hydrogen, halogen, —CN, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl, phenyl, heteroaryl, or —$X^9$—$R^9$; $X^9$ is a bond, —O—, —S—, —$NR^a$—, C(=O)—; $R^9$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl; $R^a$ is selected from among hydrogen, $C_1$-$C_6$alkyl, $C_2$-$C_6$alkenyl, hydroxy, $C_1$-$C_6$alkoxy, and $C_1$-$C_6$heteroalkyl; or $R^a$ and $R^9$ together with the N atom to which they are attached form a 5-, or 6-membered heterocycloalkyl.

In other embodiments, $R^4$ is hydrogen, substituted or unsubstituted $C_1$-$C_6$alkyl, substituted or unsubstituted $C_1$-$C_6$heteroalkyl, substituted or unsubstituted phenyl, or —$X^8$—$R^8$; $X^8$ is a $C_2$-$C_6$alkylene; $R^8$ is hydrogen, halogen, —CN, hydroxy, amino, $C_1$-$C_6$alkylamino, di($C_1$-$C_6$alkyl) amino, $C_1$-$C_6$alkoxy, $C_3$-$C_8$cycloalkyl, $C_2$-$C_8$heterocycloalkyl, phenyl, heteroaryl, or —$X^9$—$R^9$; $X^9$ is a bond, —O—, —S—, —$NR^a$—, —C(=O)—; $R^9$ is hydrogen, $C_1$-$C_6$alkyl, $C_1$-$C_6$heteroalkyl, $C_1$-$C_6$haloalkyl, $C_2$-$C_8$heterocycloalkyl, heterocycloalkylalkyl, phenyl, phenylalkyl, heteroaryl, heteroarylalkyl; $R^a$ is selected from among hydrogen, $C_1$-$C_6$alkyl, hydroxy, $C_1$-$C_6$alkoxy; or $R^a$ and $R^9$ together with the N atom to which they are attached form a 5-, or 6-membered heterocycloalkyl.

In some embodiments, $X^5$ is a bond, or a substituted or unsubstituted group selected from among $C_1$-$C_6$alkylene, $C_2$-$C_6$alkenylene, $C_1$-$C_6$fluoroalkylene, and $C_1$-$C_6$heteroalkylene. In other embodiments, $X^5$ is a bond, or a substituted or unsubstituted $C_1$-$C_6$alkylene.

In some embodiment, $R^5$ is a substituted or unsubstituted group selected from among aryl, heteroaryl, $C_3$-$C_8$cycloalkyl, and heterocycloalkyl; where if $R^5$ is substituted, then each substituent on $R^5$ is selected from among hydrogen, halogen, —CN, —$NO_2$, —S(=O)$_2NH_2$, —$CO_2H$, —$CO_2R^{10}$, —C(=O)$R^{11}$, —S—$R^{11}$, —S(=O)—$R^{11}$, —S(=O)$_2$—$R^{11}$, —S(=O)$_2$N($R^{10}$)$_2$, —$NR^{10}$C(=O)—$R^{11}$, —C(=O)N ($R^{10}$)$_2$, —S(=O)$_2$N($R^{10}$)$_2$, —$NR^{10}$S(=O)$_2$—$R^{11}$, —OC (=O)N($R^{10}$)$_2$, —$NR^{10}$C(=O)O—$R^{11}$, —OC(=O)O—$R^{11}$, —NHC(=O)NH—$R^{11}$, —OC(=O)—$R^{11}$; —N($R^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl; $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, aryl, and heteroaryl; $R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl; provided that $R^5$ is not optionally substituted pyrrole or optionally substituted 2,5-dioxo-pyrrole.

In some embodiments, $R^5$ is a substituted or unsubstituted group selected from among phenyl, naphthyl, (heteroaryl containing 0-2 N atoms, 0-1 O atoms, 0-1 S atoms), $C_3$-$C_8$cycloalkyl, and heterocycloalkyl containing 0-2 N atoms, provided that $R^5$ is not optionally substituted pyrrole or optionally substituted 2,5-dioxo-pyrrole.

In some embodiments, $R^5$ is a substituted or unsubstituted group selected from among phenyl, naphthyl, (heteroaryl containing 0-2 N atoms, 0-1 O atoms, 0-1 S atoms), $C_3$-$C_8$cycloalkyl, and heterocycloalkyl containing 0-2 N atoms.

In some embodiments, if $R^5$ is substituted, then each substituent on $R^5$ is selected from among hydrogen, halogen, —CN, —$NO_2$, —S(=O)$_2NH_2$, —$CO_2H$, —$CO_2R^{10}$, —C(=O)$R^{11}$, —S—$R^{11}$, —S(=O)—$R^{11}$, —S(=O)$_2$—$R^{11}$, —$NR^{10}$C(=O)—$R^{11}$, —C(=O)N($R^{10}$)$_2$, —S(=O)$_2$N ($R^{10}$)$_2$, —$NR^{10}$S(=)$_2$—$R^{11}$, —OC(=O)—$R^{11}$; —N($R^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted heterocycloalkyl, substituted or unsubstituted phenyl, and substituted or unsubstituted heteroaryl; $R^{10}$ is hydrogen, or a substituted or unsubstituted group selected from among $C_1$-$C_6$alkyl, $C_1$-$C_6$fluoroalkyl, $C_1$-$C_6$heteroalkyl, phenyl, and heteroaryl; $R^{11}$ is a substituted or unsubstituted group selected from among $C_1$-$C_6$alkyl, $C_1$-$C_6$fluoroalkyl, phenyl, and heteroaryl.

In some embodiments, $R^5$ is a substituted or unsubstituted group selected from among phenyl, naphthyl, (monocyclic heteroaryl containing 0-2 N atoms, 0-1 O atoms, 0-1 S atoms), and $C_2$-$C_8$heterocycloalkyl containing 0-2 N atoms.

In some embodiment, $R^5$ is not optionally substituted pyrrole or optionally substituted 2,5-dioxo-pyrrole.

In some embodiments, $R^5$ is a substituted or unsubstituted group selected from among phenyl, naphthyl, (monocyclic heteroaryl containing 0-2 N atoms, 0-1 O atoms, 0-1 S atoms), and $C_2$-$C_8$heterocycloalkyl containing 0-2 N atoms, provided that $R^5$ is not optionally substituted pyrrole or optionally substituted 2,5-dioxo-pyrrole.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In one embodiment, provided herein is a compound selected from among: 1-methyl-3-(4-nitro-phenylmethyl)-1H-indole-5-carboxylic acid hydroxyamide (Compound 34); 1-ethyl-3-(phenylmethyl)-1H-indole-5-carboxylic acid hydroxyamide (Compound 35); 1-methyl-3-[4-(phenylcarbonylamino)-phenylmethyl]-1H-indole-5-carboxylic acid hydroxyamide (Compound 36); 1-isopropyl-3-(phenylmethyl)-1H-indole-5-carboxylic acid hydroxyamide (Compound 37); 1-methyl-3-(4-amino-phenylmethyl)-1H-indole-5-carboxylic acid hydroxyamide (Compound 38); 1-methyl-3-(4-fluoro-phenylmethyl)-1H-indole-5-carboxylic acid hydroxyamide (Compound 39); 1-phenyl-3-(phenylmethyl)-1H-indole-5-carboxylic acid hydroxyamide (Compound 40); and 1-methyl-3-[4-(t-butoxycarbonyl)piperazin-1-ylmethyl]-1H-indole-5-carboxylic acid hydroxyamide (Compound 41).

Compounds described herein are selective histone deacetylase 8 (HDAC8) inhibitors. In one embodiment, the selective HDAC8 inhibitor has an $IC_{50}$ for histone deacetylase 8 activity that is at least 10 fold lower than the $IC_{50}$ of the selective HDAC8 inhibitor for histone deacetylase 1, histone deacetylase 2, histone deacetylase 3, histone deacetylase 6, histone deacetylase 10, or histone deacetylase 11. In some embodiments, compounds described have an $IC_{50}$ for histone deacetylase 8 that is at least 20 fold lower than the $IC_{50}$ for histone deacetylase 1, histone deacetylase 2, histone deacetylase 3, histone deacetylase 6, and histone deacetylase 10.

In one aspect, provided herein is a pharmaceutical composition, which includes an effective amount of a compound provided herein, and a pharmaceutically acceptable excipient.

In another aspect, provided herein are pharmaceutical compositions that include a compound, pharmaceutically acceptable salt, pharmaceutically acceptable N-oxide, pharmaceutically active metabolite, pharmaceutically acceptable prodrug, or pharmaceutically acceptable solvate of any compound described herein. In a further aspect, provided herein are compositions further including a pharmaceutically acceptable diluent, excipient or binder. In a further aspect, provided are compositions further including a second pharmaceutically active ingredient.

In certain embodiments, provided herein is a pharmaceutical composition containing: i) a physiologically acceptable carrier, diluent, and/or excipient; and ii) one or more compounds described herein.

In any of the aforementioned aspects are further embodiments that include single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments that include multiple administrations of the effective amount of the compound, including further embodiments in which (i) the compound is administered in a single dose; (ii) the time between multiple administrations is every 6 hours; (iii) the compound is administered to the mammal every 8 hours. In further or alternative embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

In one aspect, provided herein is a method of treating T-cell lymphoma or leukemia in a subject in need thereof, comprising administering to the subject a pharmaceutical composition containing a therapeutically effective amount of a compound described herein.

In one aspect, the T-cell lymphoma is peripheral T cell lymphoma. In another aspect, the T-cell lymphoma or leukemia is T cell lymphoblastic leukemia/lymphoma. In yet another aspect, the T-cell lymphoma is cutaneous T cell lymphoma. In another aspect, the T-cell lymphoma is adult T cell lymphoma.

In one aspect, the methods described herein include administering to the subject a second therapeutic agent other than a selective inhibitor of histone deacetylase 8. In one aspect, the second therapeutic agent is selected from among abarelix (Plenaxis®); aldesleukin (Prokine®); Aldesleukin (Proleukin®); Alemtuzumab (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacizumab (Avastin®); bexarotene (Targretin®); bleomycin (Blenoxane®); bortezomib (Velcade®); busulfan (Busulfex®); busulfan (Myleran®); calusterone (Methosarb®); capecitabine (Xeloda®); carboplatin Paraplatin®); carmustine (BCNU, BiCNU); carmustine (Gliadel®); celecoxib (Celebrex®); cetuximab (Erbitux®); chlorambucil (Leukeran®); cisplatin (Platinol®); cladribine (Leustatin®); clofarabine (Clolar®); cyclophosphamide (Cytoxan®); cytarabine (Cytosar-U®); cytarabine liposomal (DepoCyt); dacarbazine (DTIC-Dome); dactinomycin (actinomycin D, Cosmegen®); Darbepoetin alfa (Aranesp®); dasatinib (Sprycel®); daunorubicin liposomal (DanuoXome); daunorubicin (daunomycin, Daunorubicin®); daunorubicin (daunomycin, Cerubidine®); decitabine (Dacogen®); denileukin (Ontak®); dexrazoxane (Zinecard®); docetaxel (Taxotere®); doxorubicin (Adriamycin®); doxorubicin liposomal (Doxil®); dromostanolone propionate; epirubicin (Ellence®); Epirubicin; Epoetin alfa (EPOGEN®); erlotinib (Tarceva®); estramustine (Emcyt®); etoposide phosphate (Etopophos®); etoposide (VP-16; Vepesid®); exemestane (AROMASIN®); Filgrastim (Neupogen®); floxuridine (FUDR); fludarabine (Fludara®); fluorouracil (5-FU, Adrucil®); fulvestrant (Faslodex®); gefitinib (Iressa®); gemcitabine (Gemzar®); gemtuzumab ozogamicin (Mylotarg®); goserelin acetate (Zoladex®); histrelin acetate (Histrelin®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Leucovorin®); Leuprolide Acetate (Eligard®); levamisole (Ergamisol®); lomustine, CCNU CeeBU®); meclorethamine (nitrogen mustard, Mustargen®); megestrol acetate (Megace®); melphalan (Alkeran®); mercaptopurine (6-MP, Purinethol®); methotrexate (Rheumatrex®, Trexall®); methoxsalen (Uvadex®); mitomycin C (Mutamycin®); mitomycin C (Mitozytrex®); mitotane (Lysodren®); mitoxantrone (Novantrone®); nandrolone phenpropionate (Durabolin-50); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pegademase (Adagen®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); rituximab (Rituxan®); sargramostim (Leukine®); Sargramostim (Prokine®); sorafenib (Nexavar®); streptozocin (Zanosar®); sunitinib maleate (Sutent®); tamoxifen (Nolvadex®); temozolomide (Temodar®); teniposide (VM-26, Vumon®); testolactone (Teslac®); thalidomide (Thalomid®); thioguanine (6-TG, Thioguanine®); thiotepa (Thioplex®); topotecan (Hycamtin®); toremifene (Fareston®); tositumomab (Bexxar®); tositumomab/I-131 tositumomab (Bexxar®); trastuzumab (Herceptin®); tretinoin (ATRA, Vesanoid®); Uracil Mustard; valrubicin (Valstar®); vinblastine (Velban®); vincristine (Oncovin®); vinorelbine (Navelbine®); vorinostat (Zolinza®); zoledronate (Zometa®); and zoledronic acid (Zometa®).

In one aspect, provided herein is a method of treating a disease or condition mediated by interleukin-1 beta (IL-1b), comprising administering to the patient a therapeutically effective amount of a compound, pharmaceutically acceptable salt, pharmaceutically acceptable N-oxide, pharmaceutically active metabolite, pharmaceutically acceptable prodrug, or pharmaceutically acceptable solvate of a compound described herein. In one embodiment, the compound used in the method is a selective HDAC8 inhibitor compound described herein.

In one aspect the disease or condition is an autoimmune disease or condition. In one embodiment, the disease or condition is selected from among osteoarthritis, rheumatoid arthritis, septic arthritis, gout, pseudogout, juvenile arthritis, Still's disease, Ankylosing spondylitis, systemic lupus erythematosus (SLE), Henoch-Schdnlein purpura, psoriatic arthritis, reactive arthritis (Reiter's syndrome), hemochromatosis, hepatitis, Wegener's granulomatosis, Familial Mediterranean fever (FMF), HIDS (hyperimmunoglobulinemia D and periodic fever syndrome), TRAPS (TNF-alpha receptor associated periodic fever syndrome), inflammatory bowel disease, Crohn's Disease, ulcerative colitis, recurrent fever, anemia, leukocytosis, asthma, chronic obstructive pulmonary disease, and myalgia.

In some embodiments, the methods provided herein include administering to the subject a second therapeutic agent other than a selective inhibitor of histone deacetylase 8. In one aspect, the second therapeutic agent is selected from among immunosuppressants, glucocorticoids, non-steroidal anti-inflammatory drugs, Cox-2-specific inhibitors, leflunomide, gold thioglucose, gold thiomalate, aurofin, sulfasalazine, hydroxychloroquinine, minocycline, anti-TNF-α agents, abatacept, anakinra, interferon-β, interferon-γ, interleukin-2, allergy vaccines, antihistamines, antileukotrienes, beta-agonists, theophylline, and anticholinergics. In another embodiment, the second therapeutic agent is selected from among tacrolimus, cyclosporin, rapamicin, methotrexate, cyclophosphamide, azathioprine, mercaptopurine, mycophenolate, or FTY720, prednisone, cortisone acetate, prednisolone, methylprednisolone, dexamethasone, betamethasone, triamcinolone, beclometasone, fludrocortisone acetate, deoxycorticosterone acetate, aldosterone, aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, celecoxib, rofecoxib, valdecoxib, parecoxib, etoricoxib, lumiracoxib, CS-502, JTE-522, L-745,337 and NS398, leflunomide, gold thioglucose, gold thiomalate, aurofin, sulfasalazine, hydroxychloroquinine, minocycline, infliximab, etanercept, adalimumab, abatacept, anakinra, interferon-β, interferon-γ, interleukin-2, allergy vaccines, antihistamines, antileukotrienes, beta-agonists, theophylline, and anticholinergics.

In one embodiment, provided herein is a use of a compound described herein for the formulation of a medicament for the selective inhibition of histone deacetylase 8 activity or for the treatment of a disease or condition that would benefit from the selective inhibition of the activity of histone deacetylase 8. In one embodiment, the compound is a selective HDAC8 inhibitor.

Articles of manufacture, which include packaging material, a selective HDAC8 inhibitor compound described herein, which is effective for selectively inhibiting histone deacetylase 8 activity, within the packaging material, and a label that indicates that the compound or composition, or pharmaceutically acceptable salt, pharmaceutically acceptable N-oxide, pharmaceutically active metabolite, pharmaceutically acceptable prodrug, or pharmaceutically acceptable solvate thereof, is used for inhibiting the activity of histone deacetylase 8, or for the treatment, prevention or amelioration of one or more symptoms of a disease or condition that would benefit from inhibition of histone deacetylase 8 activity, are provided.

One aspect described herein relates to treating T-cell lymphoma by administering (e.g., orally, bucally, transdermally, intranasally, intravenously, or rectally) to a subject in need (e.g., a human) a pharmaceutical composition containing a therapeutically effective amount of a selective HDAC8 inhibitor. The T-cell lymphoma can be, e.g., peripheral T cell lymphoma, lymphoblastic lymphoma, cutaneous T cell lymphoma, NK/T-cell lymphoma, or adult T cell leukemia/lymphoma.

In one embodiment, the subject to be treated also suffers from an insulin deficiency. In some embodiments, the subject is administered, in addition to the selective HDAC8 inhibitor composition, one or more anticancer agents, e.g., topical steroids, BCNU (Carmustine), nitrogen mustards, photo therapy, topical imiquimod, EBD, MTX, doxorubicin (Doxil), gemcitibine, etoposide, pentostatin, cytokines, interferon, 5-aza-2'-deoxycytidine, all trans retinoic acid, doxorubicin, vincristine, etoposide, gemcitabine, imatinib (Gleevec®), 17-N-Allylamino-17-Demethoxygeldanamycin (17-AAG), flavopiridol, LY294002, bortezomib, trastuzumab, BAY 11-7082, PKC412, or PD184352 in any combination.

Another aspect described herein relates to treating T-cell lymphoma by administering to a subject in need a plurality of autologous T-cells that have been exposed to a pharmaceutical composition containing a therapeutically effective amount of a selective HDAC8 inhibitor ex vivo.

A further aspect described herein relates to decreasing somatostatin expression in a subject in need by administering to the subject a pharmaceutical composition containing a therapeutically effective amount of a selective HDAC8 inhibitor. In some embodiments, the subject in need of decreased somatostatin expression suffers from a growth hormone deficiency. In one embodiment, the subject suffering from a growth hormone deficiency is administered, in addition to the selective HDAC8 inhibitor composition, a therapeutically effective amount of a growth hormone secretagogue, or growth hormone.

Yet another aspect described herein relates to increasing growth hormone expression in a subject in need by administering to the subject a pharmaceutical composition containing a therapeutically effective amount of a selective HDAC8 inhibitor. In some embodiments, the subject in need of increased growth hormone expression is administered, in addition to the selective HDAC8 inhibitor composition, a therapeutically effective amount of a growth hormone secretagogue (e.g., arginine, L-3,4-dihydroxyphenylalanine, glucagon, vasopressin, pituitary adenylyl cyclase activating peptide, a muscarinic receptor agonist, or growth hormone releasing peptide), or growth hormone.

In some embodiments of any of the methods described herein, the selective inhibitor of HDAC8 binds to HDAC8.

In one aspect of any of the methods described herein, the selective HDAC8 inhibitor has an $IC_{50}$ for HDAC8 that is at least 10 fold lower than the $IC_{50}$ for HDAC1, HDAC2, HDAC3, HDAC6, HDAC10, or HDAC11.

In some embodiments, selective HDAC8 inhibitors described herein have an $IC_{50}$ for HDAC8 that is at least 15 fold lower than the $IC_{50}$ for HDAC1, HDAC2, HDAC3, HDAC6, and HDAC10. In some embodiments, selective HDAC8 inhibitors described herein have an $IC_{50}$ for HDAC8 that is at least 20 fold lower than the $IC_{50}$ for HDAC1, HDAC2, HDAC3, HDAC6, and HDAC10. In some embodiments, selective HDAC8 inhibitors described herein have an $IC_{50}$ for HDAC8 that is at least 100 fold lower than the $IC_{50}$ for HDAC1, HDAC2, HDAC3, HDAC6, and HDAC10.

In some embodiments, selective HDAC8 inhibitors described herein have an $IC_{50}$ for HDAC8 that is at least 10 fold lower than the $IC_{50}$ for HDAC1. In some embodiments, selective HDAC8 inhibitors described herein have an $IC_{50}$ for HDAC8 that is at least 20 fold lower than the $IC_{50}$ for HDAC1. In some embodiments, selective HDAC8 inhibitors described herein have an $IC_{50}$ for HDAC8 that is at least 40 fold lower than the $IC_{50}$ for HDAC1. In some embodiments, selective HDAC8 inhibitors described herein have an $IC_{50}$ for HDAC8 that is at least 100 fold lower than the $IC_{50}$ for HDAC1. In some embodiments, selective HDAC8 inhibitors described herein have an $IC_{50}$ for HDAC8 that is at least 150 fold lower than the $IC_{50}$ for HDAC1.

In some embodiments, compounds provided herein are administered to a human.

In some embodiments, compounds provided herein are orally administered.

In some embodiments, compounds provided herein are used for inhibiting the activity of HDAC8. In some embodiments, compounds provided herein are used for inhibiting the activity of HDAC8 or for the treatment of a disease or condition that would benefit from inhibition of HDAC8 activity.

In other embodiments, compounds provided herein are used for the formulation of a medicament for the inhibition of HDAC8 activity.

Other objects, features and advantages of the methods, compounds, and compositions described herein will become apparent from the following detailed description. It should be understood, however, that the detailed description and the specific examples, while indicating specific embodiments, are given by way of illustration only, since various changes and modifications within the spirit and scope of the disclosure will become apparent to those skilled in the art from this detailed description. All references cited herein, including patents, patent applications, and publications, are hereby incorporated by reference in their entirety.

BRIEF DESCRIPTION OF THE FIGURES

FIG. 1A: brain neuron and glia; FIG. 1O: thymus epithelium lymphocytes.

FIG. 2A: anti-HDAC8 antibody (Celara); FIG. 2B: anti-HDAC8 antibody (Celara) and anti-insulin antibody; FIG. 2C: anti-HDAC8 antibody (Celara) and anti-glucagon antibody; FIG. 2D: anti-HDAC8 antibody (Celara) and anti-somatostatin antibody; FIG. 2E: anti-HDAC8 antibody (SC-11405); FIG. 2F: anti-HDAC8 antibody (SC-11405) and anti-insulin antibody; FIG. 2G: anti-HDAC8 antibody (SC-11405) and anti-glucagon antibody; FIG. 2H: anti-HDAC8 antibody (SC-11405) and anti-somatostatin antibody;

FIG. 3A: pancreas malignant cells; FIG. 3B: pancreas lymphocytes and plasma cells; FIG. 3C: thymus lymphocytes; FIG. 3D: thymus inflammatory cells; FIG. 3E: hear cardiac myoctes; FIG. 3F: heart plasma cells; FIG. 3G: lung malignant cells; FIG. 3H: lung plasma cells.

FIG. 8A: lymphoma H33HJ-JA1 tumor cells (IC50=18 uM); FIG. 8B: ovary OVCAR-3 tumor cells (IC50=15 uM); FIG. 8C: pancreas MIA PaCa-2 tumor cells (IC50=17 uM); FIG. 8D: pancreas PANC-1 tumor cells (IC50=78 uM). Compound 23 does not inhibit growth of selected solid tumor lines.

FIG. 9A: HCT-116, 48 hours, Alamar Blue assay.

INCORPORATION BY REFERENCE

Figure 1A:
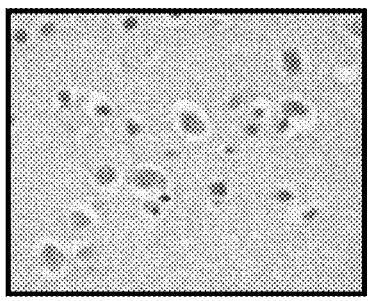
FIGS. 1A-O are illustrative panels of photomicrographs of normal human tissue sections stained for HDAC8 expression using an anti-HDAC8 antibody.
Figure 1B:
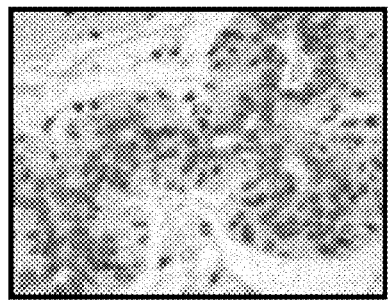
FIG. 1B: breast duct.
Figure 1C:
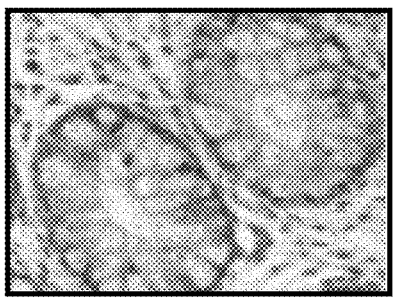
FIG. 1C: colon mucosa.
Figure 1D:
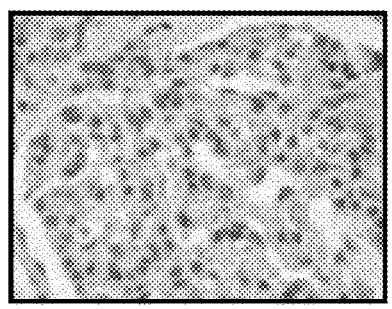
FIG. 1D: kidney glomerulus.
Figure 1E:
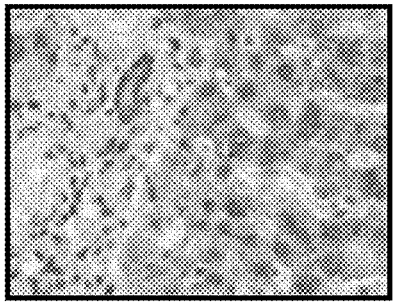
FIG. 1E: liver portal triad and hepatocytes.
Figure 1F:
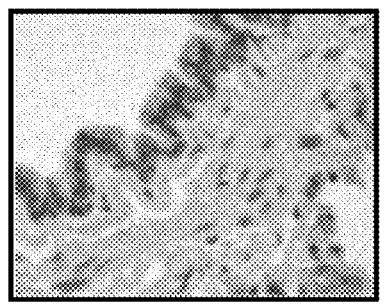
FIG. 1F: lung bronchiole.
Figure 1G:
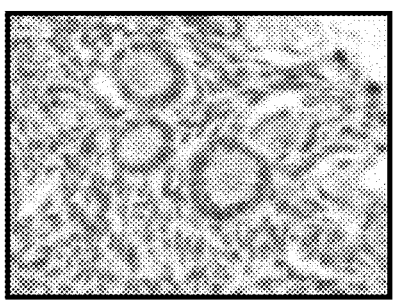
FIG. 1G: ovary follicles and stroma.
Figure 1H:
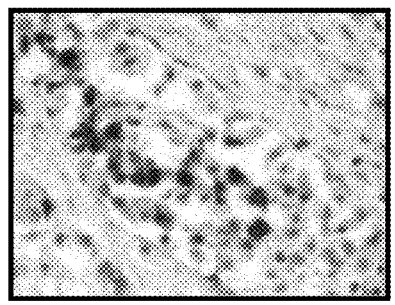
FIG. 1H: pancrease adjacent residual islet.
Figure 1I:
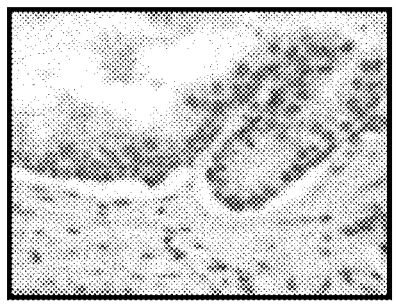
FIG. 1I: prostate glandular epithelium and stroma.
Figure 1J:
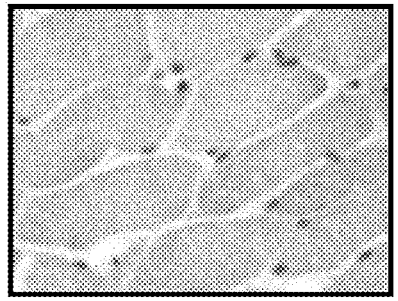
FIG. 1J: skeletal muscle myocytes.
Figure 1K:
FIG. 1K: skin squamous epithelium.
Figure 1L:
FIG. 1L: small intestine villi.
Figure 1M:
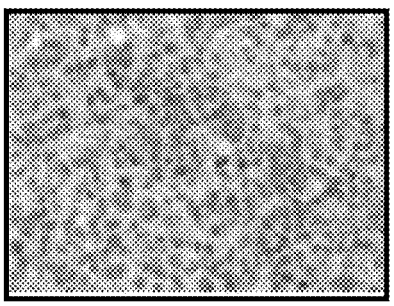
FIG. 1M: spleen red pulp.
Figure 1N:
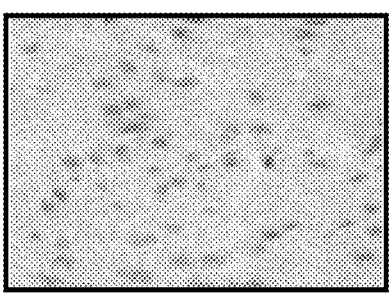
FIG. 1N: stomach: muscularis propria.
Figure 1O:
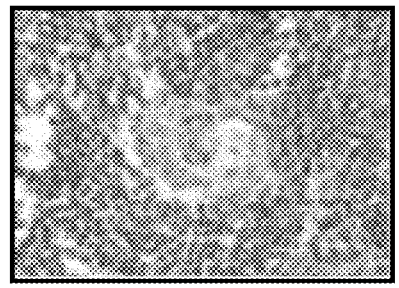
Figure 2A:
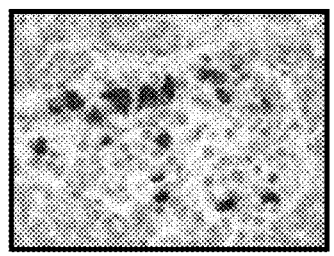
FIGS. 2A-H are illustrative panels of photomicrographs of human pancreatic tissue sections (islet DELTA cells) labeled with two independently-derived antibodies to HDAC8 (left panels, top and bottom) or double labeled with one of the anti-HDAC8 antibodies and an antibody to insulin, glucagon, or somatostatin.
Figure 2B:
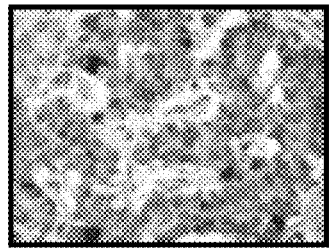
Figure 2C:
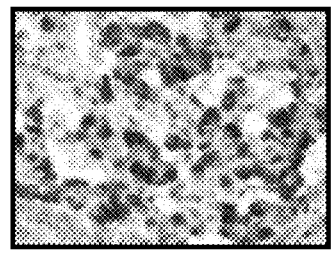
Figure 2D:
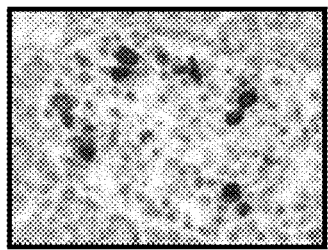
Figure 2E:
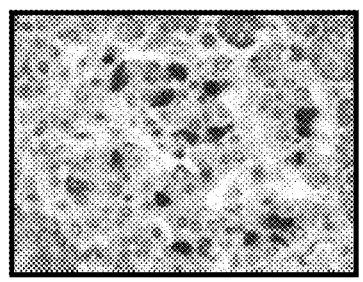
Figure 2F:
Figure 2G:
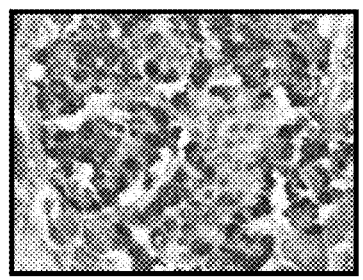
Figure 2H:
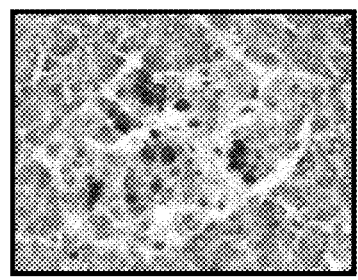
Figure 3A:
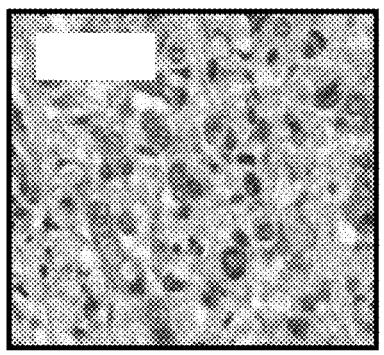
FIGS. 3A-H are illustrative panels of photomicrographs of plasma cells found in various human tissues and stained for HDAC8 expression with an anti-HDAC8 antibody.
Figure 3B:
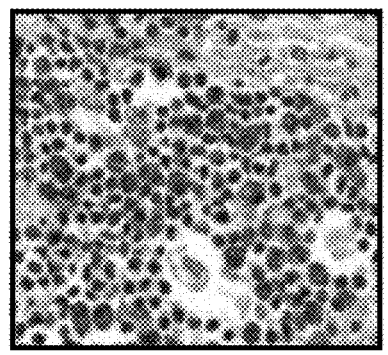
Figure 3C:
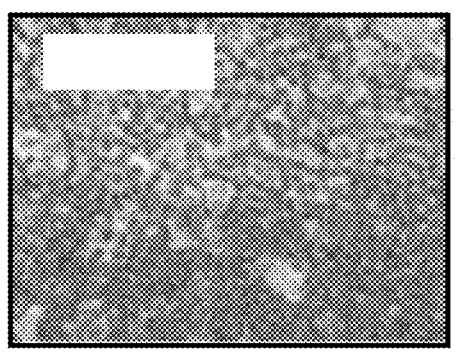
Figure 3D:
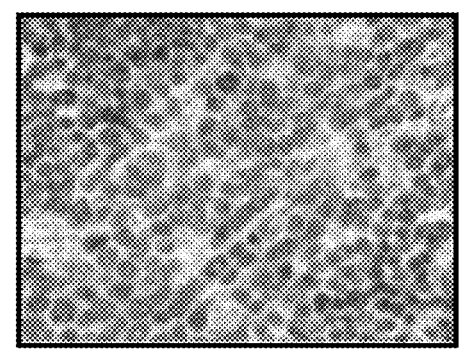
Figure 3E:
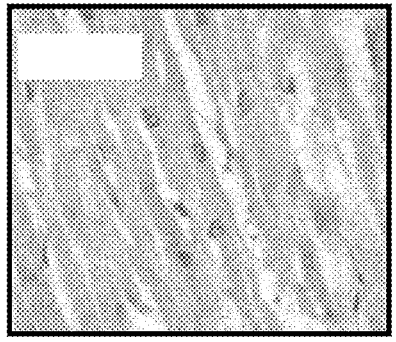
Figure 3F:
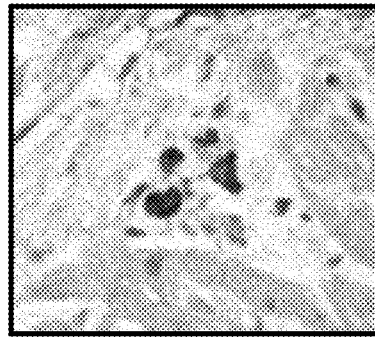
Figure 3G:
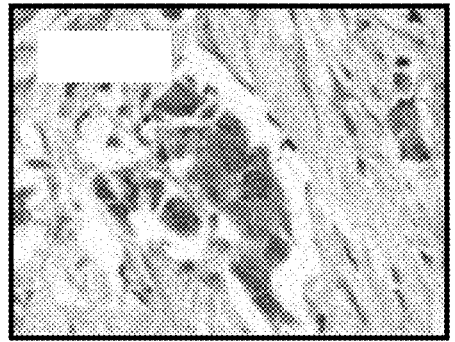
Figure 3H:
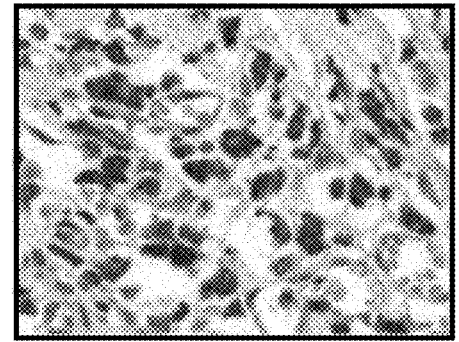

All publications and patent applications mentioned in this specification are herein incorporated by reference to the same extent as if each individual publication or patent application was specifically and individually indicated to be incorporated by reference.

DETAILED DESCRIPTION

Covalent modification of histone proteins through acetylation and deacetylation is an important determinant of chromatin structure and a regulator of gene expression. Acetylation of histone proteins occurs on lysine residues near the N-termini of these proteins. In conjunction with other modifications of histone proteins and DNA, the acetylation state of histones determines whether the chromatin is in a condensed, transcriptionally silent state or in a form more accessible to the transcription machinery of the cell. In general, hyperacetylation of histone proteins is associated with transcriptional activation of genes. The steady-state histone acetylation level arises from the opposing action of histone acetyltransferase (HAT) and histone deacetylase (HDAC) enzymes.

Histone deacetylases (HDACs) catalyze the removal of acetyl groups from lysine ε-amino groups near the N-termini of histones. This reaction promotes the condensation of chromatin, leading to repression of transcription.

HDAC inhibitors (HDIs) modify gene expression positively or negatively in a cell- and gene-specific manner. HDIs increase the accumulation of acetylated histones, directly influencing chromatin structure and, thereby, the relationship of the nucleosome to gene promoter elements.

Histone deacetylase (HDAC) enzymes modulate gene expression through the deacetylation of acetylated lysine residues on histone proteins. They operate in biological systems as part of multiprotein corepressor complexes. Histone deacetylases have been grouped into three classes. Class I and class II histone deacetylases (HDACs) are zinc containing hydrolase enzymes. The division of the proteins into classes I and II is based on protein size, sequence similarity, and organization of the protein domains.

Members of class I are related to the yeast RPD3 gene product. Class I HDACs include: HDAC1 (GenBank Accession Number NP_004955; Wolffe, A. P., *Science* 272, 5260, 371-372, 1996); HDAC2 (GenBank Accession Number NP_001518; Furukawa, et al., *Cytogenet. Cell Genet.* 73; 1-2, 130-133, 1996); HDAC3 (GenBank Accession Number NP_003874; Yang, et al., *J. Biol. Chem.* 272, 44, 28001-28007, 1997); HDAC8 (GenBank Accession Number NP_060956; Buggy, et al., *Biochem. J.* 350 Pt 1, 199-205, 2000); HDAC11 (GenBank Accession Number NP_079103; Gao, L. et al., *J. Biol. Chem.* 277, 28, 25748-25755, 2002).

HDAC8 is a 377 residue, 42 kDa protein localized to the nucleus of a wide array of tissues, as well as several human tumor cell lines. The wild-type form of full length HDAC8 is described in GenBank Accession Number NP 060956; Buggy, J. J. et al., *Biochem. J.*, 350 (Pt 1), 199-205 (2000). The HDAC8 structure was solved with four different hydroxamate inhibitors bound (Somoza et al., *Structure*, 2004, 12, 1325)

Class II are homologues of the yeast HDA1 protein (de Ruijter et. al. *Biochem J.* 2003, 370(Pt 3), 737-49), and include:

HDAC4 (GenBank Accession Number NP_006028; Wolffe, A. P., *Nature* 387, 6628, 16-17, 1997); HDAC5 (GenBank Accession Number NP_631944; Nagase, T., et al., *DNA Res.* 5 (1), 31-39, 1998); HDAC6 (GenBank Accession Number NP_006035; Wolffe, A. P., *Nature* 387, 6628, 16-17, 1997); HDAC7 (GenBank Accession Number NP_057680; Kao, H. Y., et al., *Genes Dev.* 14 (1), 55-66, 2000); HDAC9 (GenBank Accession Number NP_478056; Sparrow, et al., *EMBO J.* 18 (18), 5085-5098, 1999); HDAC10 (GenBank Accession Number NP_114408; Kao, H. Y., et al., *J. Biol. Chem.* 277 (1), 187-193, 2002).

Class II HDACs have been further subdivided into classes IIa (HDACs 4, 5, 7, and 9) and IIb (HDACs 6 and 10).

The third class of deacetylases consists of the members of the Sir2 family of enzymes. These enzymes have histone deacetylase activity but are structurally and evolutionarily unrelated to the class I and class II proteins. They are (nicotinamide adenine dinucleotide) NAD-dependent and unlike class I HDACs and class II HDACs, they do not contain a catalytic zinc site In the cell, HDAC proteins are recruited as part of multicomponent repressor complexes. Several HDAC containing complexes have been characterized, including the N-CoR/SMRT, Sin3, NuRD, and CoREST complexes. Within these complexes, HDACs 1 and 2 typically interact with the mSin3, Mi-2, or CoREST proteins. HDAC3 and the class IIa HDACs have been shown to interact with SMRT and the related N-CoR protein. A large number of transcription factors have been shown to bind to one of the corepressor complexes as a means of regulating transcription. The recruitment of HDACs by DNA-binding proteins allows histone deacetylation to be directed toward specific regions of the chromatin in order to promote targeted transcriptional repression HDAC proteins are promising therapeutic targets on account of their involvement in regulating genes involved in cell cycle progression and control. Inhibition of HDACs has been shown to upregulate genes, including p21WAF/CIP1, $p^{27}$, p53, and cyclin E, and to downregulate genes such as cyclin A and cyclin D. Growth inhibition in several lines of cancer cells has been observed upon treatment with HDAC inhibitors, and in vivo studies have shown that some of these inhibitors are efficacious in slowing tumor growth. The biological activity of each of the HDAC isozymes is determined by a combination of the intrinsic activity of the enzyme and the effects of cofactor binding on reactivity and substrate recognition (Schultz et al., *Biochemistry*, 2004, 43, 11083-11091).

Methods for determining HDAC activity in vivo or in vitro are known in the art, as disclosed in, e.g., Kim et al. (2006), *Methods Mol Biol.*, 325:273-283.

Non-selective HDAC inhibitors inhibit the deacetylase activity of most, if not all, of the HDACs with equal potency. The mechanisms of the anticancer effects of SAHA, a non-selective HDAC inhibitor, are not completely understood, and likely result from both altered gene expression and altered function of proteins regulating cell proliferation and cell death pathways. Non-selective HDAC inhibitors, such as SAHA, can induce the accumulation of acetylated histone proteins and non histone proteins. Non-histone proteins that are acetylated include, but are not limited to:

Bcl-6 (Oncoprotein); LEF/TCF (Lymphoid enhancer factor); P53 (Tumor suppressor); Ku70 (Autoantigen with multiple function, including DNA repair); H1F-1α (angiogenesis); GATA-1 (Transcription factor); WRN (Werner helicase); E2F-1 (Transcription factor); Smad7 (Transcription factor); Rb (Tumor suppressor); TFIIF (Transcription machinery); c-Jun (Transcription factor); α-Tubulin (Structural protein); HMGI(Y) (Chromatin structure); ACTR (Nuclear receptor coactivator); Androgen Receptor (Signal transduction); EKLF (Erythroid kruppel-like factor); YY-1 (Transcription factor); NF-κB(RelA) (Transcription factor); MyoD (Transcription factor); Importin a7 (Nuclear pore protein); Hsp90 (Chaperone protein); TFIIE (Transcription machinery); b-Catenin (Signaltransduction); TFJB (Transcription factor).

Genes whose transcription is altered by histone deacetylase inhibitors include:

1) Genes that are induced by HDAC inhibitors: Cell cycle (p1 and cyclin E); Proapoptotic (Bak, BAX, CD95, and its ligand gelsolin, GADD45β, p53, Apaf-1 DFF45a, Bim, BAD, TRAIL, DR5, Fas and its ligand, and Caspase 9, -8 and -3); Redox Components (Thioredoxin-binding protein-1, thioredoxin, glutaredoxin and methallothionein IL); Chromatin structure (Histone H2B); Retinoic acid pathway (RARβ).

2) Genes that are repressed by HDAC inhibitors: Cell cycle (Cyclin D1 and A, and thymidylate synthase); Antiapoptotic (Bcl-2, Bcl-XL, c-FLIP, survivin, XIAP); Angiogenic factor (Vascular endothelial growth factor and HIF-Loc); Lipopolysaccharide-induced inflammatory cytokines (TNF-α, IFN-g and IL-1b and -6); Signaltransducer and activator of transcription 5-controlled genes (STATS).

The pharmaceutical industry seeks novel anti-cancer therapies targeting the underlying molecular defects that cause cancer with less toxicity than traditional chemotherapy (Miller et al., *J. Med. Chem.*, 2003, vol. 46, no. 24, 5097-5116). The inappropriate deacetylation of tumour suppressor genes, a molecular defect, may silence these genes, resulting in the progression of cancer. HDAC inhibitors selectively switch on these tumour suppressor genes, something traditional chemotherapy may not do.

HDAC enzymes or isoforms appear to be involved in many different types of cancer. Inhibition of HDACs with HDAC inhibitors results in multiple and desirable anti-cancer effects such as, but not limited to, (i) the inhibition of cancer cell proliferation, (ii) the induction of apoptosis (cell death) of cancer cells, (iii) cell cycle regulation, (iv) the induction of tumour suppressor genes, and (v) the blocking of tumour angiogenesis (development of new tumour blood vessels). These multiple effects provided by HDAC inhibitors provide a method of treating cancer.

Interest in histone deacetylase enzymes (HDACs) as targets for pharmaceutical development has centered on the role of HDACs in regulating genes associated with cell-cycle progression and the development and progression of cancer (Kramer et. al. *Trends Endocrinol. Metab.* 12, 294-300, (2001)). Several studies have shown that treatment of various cell lines with HDAC inhibitors leads to hyper acetylation of histone proteins and cell-cycle arrest in late $G_1$ phase or at the $G_2$/M transition. Genes involved in the cell cycle that have been shown to be up regulated by HDAC inhibitors include p21, p27, p53 and cyclin E. Cyclin A and cyclin D have been reported to be down regulated by HDAC inhibitors. In tumor cell lines, several studies have shown that treatment with HDAC inhibitors can lead to growth inhibition, growth arrest, terminal differentiation and/or apoptosis. In vivo studies have demonstrated growth inhibition of tumors and a reduction in tumor metastasis as a result of treatment with HDAC inhibitors.

The clearest link between abnormal HDAC activity and cancer occurs in acute promyelocytic leukemia. In this condition, a chromosomal translocation leads to the fusion of the retinoic acid receptor RARα with the promyelocytic leukemia (PML) or promyelocytic leukemia zinc-finger (PLZF) proteins. Both PML-RARα and PLZF-RARα promote the progression of leukemia by repressing retinoic acid-regulated genes through the abnormal recruitment of SMRT-mSin3-HDAC complex (Lin et. al. *Nature* 391, 811-814 (1998)); Grignani et al. *Nature* 391, 815-818 (1998)). Whereas the PML-RARα form of the disease is treatable with retinoic acid, the PLZF-RARα form is resistant to this treatment. For a patient with the retinoic acid-resistant form of the disease, the addition of the HDAC inhibitor sodium butyrate to the dosing regimen led to complete clinical and cytogenic remission (Warrell et al. *J. Natl. Cancer. Inst.* 90, 1621-1625, (1998)). HDACs have also been associated with Huntington's disease (Steffan, et al., *Nature* 413:739-744, "Histone deacetylase inhibitors arrest polyglutamine-dependent neurodegeneration in *Drosophila*").

In general, almost all of the inhibitors targeting HDACs are broad spectrum compounds, inhibiting all of the HDAC isoforms with equal potency. These broad spectrum HDAC inhibitors cause the induction of differentiation, growth arrest and/or apoptosis in a large number of tumor cell lines in vitro.

Clinical administration of broad spectrum HDAC inhibitors (pan HDAC inhibitors) has been associated with many dose limiting toxicities. These include thrombocytopenia, and other hematological toxicities, QTc prolongation and other cardiac toxicities, nausea, fever, fatigue, and anorexia (For example, see *Clinical Cancer Research* 2003, 9(10), 3578-3588; *Clinical Cancer Research* 2002, 8(7), 2142-2148; and *Proceedings of the American Association of Cancer Research* 2005, 46, Abs 3978). Selective HDAC inhibitors that selectively inhibit only one HDAC isoform, as opposed to a pan-selective inhibitor, is expected to produce a drug with an improved toxicity profile.

Adverse effects in humans have been reported in several clinical trials using pan-HDAC inhibitors (Kelly et al., (2003). "Phase I clinical trial of histone deacetylase inhibitor: suberoylanilide hydroxamic acid administered intravenously." *Clin Cancer Res* 9: 3578-3588. Kelly et al. (2005). "Phase I study of an oral histone deacetylase inhibitor, suberoylanilide hydroxamic acid, in patients with advanced cancer." *J Clin Oncol* 10: 3923-3931.2003, 2005; Ryan et al., (2005). Phase I and pharmacokinetic study of MS-275, a histone deacetylase inhibitor, in patients with advanced and refractory solid tumors or lymphoma." *J Clin Oncol* 10: 3912-3922.2005). Originally designed for oncological applications, such toxicities might not be crucial when taking into consideration their therapeutic effects and the high mortality rate of cancer. HDAC inhibitor compounds with reduced toxicities would be beneficial and could be used in the treatment of diseases or conditions other than cancer.

There is an ongoing need for compositions and therapeutic methods based on inhibition of specific histone deacetylases. Described herein are selective HDAC8 inhibitor compounds. Compounds described herein selectively inhibit HDAC8 over other HDAC isoforms (e.g. HDACs 1, 2, 3, 6, 10, and 11).

As described herein, HDAC8 is expressed primarily in delta cells of the islets of Langerhans in the pancreas; in small intestinal epithelial cells; and in neuroendocrine cells. Of note, delta cells express and secrete somatostatin, a peptide hormone that inhibits the secretion of insulin and growth hormone. Without being bound by theory, it is believed that HDAC8 activity drives the expression of somatostatin in delta cells. Thus, inhibiting HDAC8 activity is expected to decrease somatostatin expression and secretion from delta cells, and consequently increase systemic insulin and growth hormone levels.

Described herein are methods for inhibiting somatostatin expression in a subject by administering to the subject a selective HDAC8 inhibitor composition. Further, described herein are methods for treating a subject suffering from an insulin deficiency or a growth hormone deficiency by administering a selective HDAC8 inhibitor to the subject.

T-Cell Lymphomas or Leukemias

HDAC8 is expressed at unusually high levels in tumor cell lines, e.g., Jurkat, HuT78, K562, PC3, and OVCR-3. In fact, as described herein, inhibiting HDAC8 activity decreases proliferation of T-cell derived tumor cells (e.g., Jurkat cells) by apoptosis. In contrast, HDAC8 inhibition does not affect the proliferation of either non-cancerous cells (e.g., peripheral blood mononuclear cells) or tumor cell lines other than T-cell derived lines. Thus, selective HDAC8 inhibitors are useful for slowing or arresting the progression of T-cell derived cancers with lessened or no toxicity to non-cancerous cells.

Selective HDAC8 inhibitor compounds described herein were screened against a large panel of tumor cell lines in vitro, and were found to induce apoptosis in cell lines derived from T-cell lymphomas or leukemias. Selective HDAC8 inhibitor compounds described herein at low micromolar concentrations inhibits the growth of Jurkat and HuT78 cell lines while doses as high as 20 micromolar have no effect on B cell or myeloid-derived lymphomas or solid tumor lines. Unlike broad spectrum inhibitors, selective HDAC8 inhibitor compounds described herein do not cause detectable histone or tubulin acetylation, but lead to a dose dependent decrease in HDAC8 protein levels in treated cells. Selective HDAC8 inhibitor compounds described herein activated caspases 3, 8 and 9, showing that both intrinsic and extrinsic apoptic pathways were involved; accordingly, apoptosis was blocked completely by pan-caspase inhibitors but only partially by inhibitors of specific caspases. Thus, selective HDAC8 inhibitor compounds described herein may be of benefit in the treatment of T-cell lymphomas and leukemias.

Described herein are methods for treating a subject suffering from a T-cell lymphoma by administering to the subject a selective HDAC8 inhibitor composition. Also described herein are methods for treating a subject suffering from a T-cell lymphoma by administering to the subject a population of autologous T-cells that have been exposed to a selective HDAC8 inhibitor composition ex vivo.

Selective HDAC8 inhibitor compounds and compositions thereof can be used to treat a subject suffering from a T-cell lymphoma, e.g., a peripheral T-cell lymphoma, a lymphoblastic lymphoma, a cutaneous T-cell lymphoma, or an adult T-cell lymphoma.

In some embodiments, the T-cell lymphoma treatment method includes administering to a subject a therapeutically effective amount of a selective HDAC8 inhibitor pharmaceutical composition.

In other embodiments, the T-cell lymphoma treatment can include administering, in addition to a selective HDAC8 inhibitor pharmaceutical composition, one or more additional anti-cancer agents described herein in any combination.

The methods described herein include administering a pharmaceutical composition containing a selective HDAC8 inhibitor in a quantity sufficient to decrease HDAC8 deacetylase activity in vivo by a therapeutically effective amount. In some embodiments, cells derived from a subject to be treated (i.e. autologous cells) are exposed, ex vivo, to a pharmaceutical composition containing a selective HDAC8 inhibitor composition in a quantity sufficient to decrease HDAC8 deacetylase activity in vitro.

In one embodiment, T-cells from a donor subject suffering a T-cell lymphoma are cultured and expanded, ex vivo, in the presence of a selective HDAC8 inhibitor at a concentration that is effective for selectively killing transformed T-cells. Afterwards, the expanded T-cell population, free of transformed T-cells, can be introduced into the donor subject. T-cell culture, in vitro expansion, and in vivo transfer is described in, e.g., Porter et al. (2006), *Blood*, 107(4):1325-1331; Rapoport et al. (2005), *Nat. Med.*, 1230-1237; Laport et al. (2003), *Blood*, 102(6):2004-2013.

Inhibition of IL-1b Secretion

Pan-HDAC inhibitors have been examined for their application in immunological disorders. Cytokine production is regulated through selective patterns of histone acetylation (Avni et al. *Nature Immunol.*, 2002, 3, 643). It is known that broad spectrum HDAC inhibitors (e.g. suberoylanilide hydroxamic acid (SAHA), trichostatin (TSA)) decrease LPS-stimulated cytokine production in vitro and in vivo and have anti-inflammatory properties (Leoni et al. *PNAS USA*, 2002, 99, 2995; Mascagni et al., International Patent Publication WO 03/013493). Nonselective HDAC inhibitors, such as SAHA and TSA, have also been shown to antagonize systemic lupus erythematosus in a mouse model (International patent publication WO 02/55017; Mishra et al., *J. Clin. Invest.*, 2003, 111, 539).

Histone deacetylase inhibitors prevent exocytosis of interleukin-1b-containing secretory lysosomes. A functional microtubule network is required for IL-1b secretion and disruption of tubulin is the mechanism by which HDAC inhibitors reduce cytokine secretion (Carta et al. *Blood.* 2006, 1; 108(5):1618-26). Carta et al. examined the effects of pan-HDAC inhibitors (e.g. SAHA, TSA) on IL-1b secretion, and concluded that the effects of the pan-HDAC inhibitors on secretion of IL-1b is acheived by the inhibition cytoplasmic HDAC6. Carta et al. also showed that HDAC inhibitors inhibit the secretion of IL-1b, but do not inhibit the synthesis of its presursor.

As described herein, selective HDAC8 inhibitor compounds described herein reduce the secretion of proinflammatory cytokines including but not limited to interleukin-1 beta (IL-1b). Thus, HDAC8 is the HDAC enzyme involved in cytokine secretion. The use of selective HDAC8 inhibitor compounds provides a method of reducing cytokine secretion with reduced toxicity, due to the selective inhibition of one HDAC isoform (vs. the use of pan-HDAC inhibitors that inhibit all of the HDAC isoforms).

Selective HDAC8 inhibitor compounds described herein inhibit, in a dose dependent fashion, lipopolysaccharide (LPS) and/or ATP stimulated secretion of IL-1b from purified human peripheral blood mononuclear cells (PBMCs) as well as from the monocyte cell line THP-1. In some embodiments, the $EC_{50}$ for inhibition ranges from 0.5 micromolar to 5 micromolar.

The production and secretion of IL-1b is via a non-classical pathway of protein secretion, involving potassium efflux, the autocatalytic processing of procaspase-1, the cleavage by active caspase-1 of the IL-1b precursor, the influx of calcium ions, and the activation of specific phospholipases including PLA-2. Selective HDAC8 inhibitor compounds described herein inhibit one or more steps in this secretory pathway.

Selective HDAC8 inhibitors may be used to treat diseases or conditions that are mediated or linked to IL-1b secretion and activity. Selective HDAC8 inhibitor compounds may be used to treat autoimmune diseases or conditions in which IL-1b is contributor to the signs and symptoms of the diseases or conditions (Burger et al., *Best Practice & Research Clinical Rheumatology*, Vol. 20, No. 5, pp. 879-896, 2006; Dayer et al., *Current Opinions in Rheum.*, 2001, 13:170-176; Abramson et al., *Rheumatology*, 2002; 41; 972-980). Selective HDAC8 inhibitor compounds may be used to inhibit IL-1b secretion and thus find utility in the treatment of diseases or conditions that are linked to IL-1b secretion and activity, which include, but are not limited to, osteoarthritis, rheumatoid arthritis, septic arthritis, gout, pseudogout, juvenile arthritis, Still's disease, Ankylosing spondylitis, systemic lupus erythematosus (SLE), Henoch-Schönlein purpura, psoriatic arthritis, reactive arthritis (Reiter's syndrome), hemochromatosis, hepatitis, Wegener's granulomatosis, Familial Mediterranean fever (FMF), HIDS (hyperimmunoglobulinemia D and periodic fever syndrome), TRAPS (TNF-alpha receptor associated periodic fever syndrome), inflammatory bowel disease, Crohn's Disease, ulcerative colitis, recurrent fever, anemia, leukocytosis, asthma, chronic obstructive pulmonary disease, myalgia; Adult Still's disease, Systemic-onset juvenile idiopathic arthritis, Lupus arthritis, Ankylosing spondylitis, familial Mediterranean fever (FMF), TNF receptor-associated periodic syndrome (TRAPS), hyperimmunoglobulinemia D with periodic fever syndrome (HIDS), Blau syndrome, FCAS, MWS, neonatal-onset multisystem inflammatory disease (NOMID) and cryopyrin-associated periodic syndrome (CAPS), familial cold autoinflammatory syndrome (FCAS); Muckle-Wells syndrome (MWS); neonatal-onset multisystem inflammatory disease (NOMID); chronic infantile neurologic, cutaneous, articular syndrome (CINCA); cryopyrin-associated periodic syndrome (CAPS); pyogenic sterile arthritis, pyoderma gangrenosum, and acne syndrome (PAPA).

Chronic inflammation in patients has been linked to cancer development (Coussens et al., *Nature*, 420, 860-867, 2002). Cancers associated with chronic inflammation include, but are not limited to, lung, esophageal, gastric, pancreatic, cervical, bladder, prostate and colorectal cancers. The role of the inflammatory microenvironment as a causative factor in the etiology of cancer is also supported by findings that regular use of non-steroidal anti-inflammatory drugs (NSAIDs) is associated with a reduced incidence of colorectal, breast and gastric cancer. Pro-inflammatory cytokines are mediators of chronic inflammatory responses, and have effects on malignant processes.

Pro-inflammatory cytokines are involved in carcinogenesis and malignant transformation, tumor growth, invasion and metastasis. Persistent expression of proinflammatory cytokines, in or near tumors, exerts a range of effects, including but not limited to, increasing growth and invasiveness of the malignant cells, metastsis, tumorigenesis, to activation of immune-mediated mechanisms, leading to the destruction of tumor cells and inhibition of tumor growth. IL-1b-transfected tumor cells have been reported to fail to induce effective antitumor immune responses. In several human cancers, local IL-1b expression by the malignant cells or the microenvironment has been associated with aggressive tumor growth and poor prognosis.

In IL-1b-transfected fibrosarcoma cells, an up-regulation of MMP-2 and MMP-9 and TGFβ, genes that are involved in invasiveness, was observed, as opposed to the shut-off of these genes in IL-1α-transfected fibrosarcomas cells. IL-1b may also enhance the invasiveness of already existing tumor cells by switching on angiogenesis and by the induction of inflammatory molecules, such as MMPs, heparanase, chemokines or integrins on the malignant cells or endothelial cells, leading to tumor dissemination and metastasis. Il-1b induces secretion of growth and invasiveness-promoting factors, e.g. matrix metalloproteinases and angiogenic factors (i.e. VEGF and bFGF and ELR-positive CXC chemokines, i.e. IL-8 and MCP-1). (Apte et al., seminars in *Cancer Biology*, vol. 12, 2002, 277-290).

Secreted IL-1b seems to be involved in tumor growth and invasion. Inhibition of IL-1b secretion, e.g. by using selective HDAC8 compounds, in malignant cells, or in the tumor's microenvironment may provide a method for cancer therapy.

Thus in one embodiment, selective HDAC8 compounds described herein, may be used in cancer therapy. In one embodiment, selective HDAC8 compounds described herein, may be used in the treatment of sarcomas. In another embodiment, selective HDAC8 compounds described herein, may be used in the treatment of sarcomas selected from among alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, kaposi's sarcoma, leiomyosarcoma, liposarcoma, lymphangiosarcoma, malignant fibrous histiocytoma, neurofibrosarcoma, rhabdomyosarcoma, synovial sarcoma, askin's tumor, ewing's, malignant hemangioendothelioma, malignant schwannoma, osteosarcoma, chondrosarcoma.

Compounds

Compounds described herein, pharmaceutically acceptable salts, pharmaceutically acceptable N-oxides, pharmaceutically active metabolites, pharmaceutically acceptable prodrugs, or pharmaceutically acceptable solvates thereof, inhibit HDAC8 activity, and may be used to treat patients where inhibition of HDAC8 activity provides benefit. Compounds described herein are selective HDAC8 inhibitor compounds.

In some embodiments of any of the methods described herein, the selective HDAC8 inhibitor has an $IC_{50}$ for HDAC8 that is at least 10 fold lower than the $IC_{50}$ for HDAC1, HDAC2, HDAC3, HDAC6, HDAC10, or HDAC11. In some embodiments of any of the methods described herein, the selective HDAC8 inhibitor has an $IC_{50}$ for HDAC8 that is less than 100 nM and that is at least 10 fold lower than the $IC_{50}$ for HDAC1, HDAC2, HDAC3, HDAC6, HDAC10, or HDAC11. In some embodiments of any of the methods described herein, the selective HDAC8 inhibitor has an $IC_{50}$ for HDAC8 that is less than 50 nM and that is at least 10 fold lower than the $IC_{50}$ of the selective inhibitor for HDAC1, HDAC2, HDAC3, HDAC6, HDAC10, or HDAC11.

In some embodiments, selective HDAC8 inhibitors described herein have an $IC_{50}$ for HDAC8 that is at least 15 fold lower than the $IC_{50}$ for HDAC1, HDAC2, HDAC3, HDAC6, and HDAC10. In some embodiments, selective HDAC8 inhibitors described herein have an $IC_{50}$ for HDAC8 that is at least 20 fold lower than the $IC_{50}$ for HDAC1, HDAC2, HDAC3, HDAC6, and HDAC10. In some embodiments, selective HDAC8 inhibitors described herein have an $IC_{50}$ for HDAC8 that is at least 100 fold lower than the $IC_{50}$ for HDAC1, HDAC2, HDAC3, HDAC6, and HDAC10. In addition, selective HDAC8 inhibitors described herein have an $IC_{50}$ for HDAC8 that is less than 100 nM while the $IC_{50}$ for HDAC1, HDAC2, HDAC3, HDAC6, and HDAC10 is greater than 100 nM.

In some embodiments, selective HDAC8 inhibitors described herein have an $IC_{50}$ for HDAC8 that is at least 10 fold lower than the $IC_{50}$ for HDAC1. In some embodiments, selective HDAC8 inhibitors described herein have an $IC_{50}$ for HDAC8 that is at least 20 fold lower than the $IC_{50}$ for HDAC1. In some embodiments, selective HDAC8 inhibitors described herein have an $IC_{50}$ for HDAC8 that is at least 40 fold lower than the $IC_{50}$ for HDAC1. In some embodiments, selective HDAC8 inhibitors described herein have an $IC_{50}$ for HDAC8 that is at least 100 fold lower than the $IC_{50}$ for HDAC1. In some embodiments, selective HDAC8 inhibitors described herein have an $IC_{50}$ for HDAC8 that is at least 150 fold lower than the $IC_{50}$ for HDAC1. In yet other embodiments, selective HDAC8 inhibitors described herein have an $IC_{50}$ for HDAC8 that is at least 200 fold lower than the $IC_{50}$ for HDAC1.

In some embodiments, selective HDAC8 inhibitors described herein have $IC_{50}$ for HDAC8 that is less than 100 nM and that is at least 20 fold lower than the $IC_{50}$ for other HDAC isoforms (HDAC1, HDAC2, HDAC3, HDAC6, HDAC10), wherein the $IC_{50}$ for the other HDAC isoforms is greater than 100 nM.

In one embodiment, described herein are substituted indole-6-carboxylic acid hydroxyamide compounds and substituted indole-5-carboxylic acid hydroxyamide compounds that are selective HDAC8 inhibitors. Compounds described herein are selective histone deacetylase 8 (HDAC8) inhibitors. In one embodiment, the selective HDAC8 inhibitor has an $IC_{50}$ for histone deacetylase 8 activity that is at least 10 fold lower than the $IC_{50}$ of the selective HDAC8 inhibitor for activity of histone deacetylase 1, histone deacetylase 2, histone deacetylase 3, histone deacetylase 6, histone deacetylase 10, or histone deacetylase 11.

In one embodiment, described herein is a 1,3-disubstituted-1H-indole-6-carboxylic acid hydroxyamide compound, wherein the substituent at the 1-position is $—X^2—R^2$ and the substituent at the 3-position is $R^3$, wherein:

$X^2$ is a bond, or a substituted or unsubstituted group selected from among $C_1$-$C_6$alkylene, $C_2$-$C_6$alkenylene, $C_2$-$C_6$ alkynylene, $C_1$-$C_6$fluoroalkylene, $C_2$-$C_6$fluoroalkenylene, $C_1$-$C_6$haloalkylene, $C_2$-$C_6$haloalkenylene, $C_1$-$C_6$heteroalkylene; —C(=O)—, and —C(=O)—$C_1$-$C_6$alkylene;

$R^2$ is a substituted or unsubstituted group selected from among aryl, heteroaryl, cycloalkyl, and heterocycloalkyl;
  where if $R^2$ is substituted, then each substituent on $R^2$ is selected from among hydrogen, halogen, —CN, —NO$_2$, —S(=O)$_2$NH$_2$, —CO$_2$H, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —NR$^{10}$S(=O)$_2$—R$^{11}$, —OC(=O)N(R$^{10}$)$_2$, —NR$^{10}$C(=O)O—R$^{11}$, —OC(=O)O—R$^{11}$, —NHC(=O)NH—R$^{11}$, —OC(=O)—R$^{11}$; —N(R$^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl;
    $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, aryl, and heteroaryl;
    $R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;
$R^3$ is hydrogen, halogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, or —X$^6$—R$^6$;
$X^6$ is a $C_1$-$C_6$alkylene, $C_1$-$C_6$fluoroalkylene, $C_2$-$C_6$alkenylene, $C_2$-$C_6$heteroalkylene;
$R^6$ is hydrogen, halogen, —CN, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl, phenyl, heteroaryl, or —X$^7$—R$^7$
$X^7$ is a bond, —O—, —S—, —S(=O)—, —S(=O)$_2$—, —NR$^a$—, —C(=O)—, —C(=O)O—, —OC(=O)—, —NHC(=O)—, —C(=O)NR$^a$—, —S(=O)$_2$NR$^a$—, —NHS(=O)$_2$—, —OC(=O) NR$^a$—, —NHC(=O)O—, —OC(=O)O—, —NHC(=O)NR$^a$—;
$R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl,
  $R^a$ is selected from among hydrogen, $C_1$-$C_6$alkyl, $C_2$-$C_6$alkenyl, hydroxy, $C_1$-$C_6$alkoxy, $C_1$-$C_6$fluoroalkoxy, $C_1$-$C_6$heteroalkyl; or
  $R^a$ and $R^7$ together with the N atom to which they are attached form a 5-, 6-, or 7-membered heterocycloalkyl;

or an active metabolite, pharmaceutically acceptable solvate, pharmaceutically acceptable salt, pharmaceutically acceptable N-oxide, or pharmaceutically acceptable prodrug thereof.

For any and all of the embodiments, substituents can be selected from among from a subset of the listed alternatives. For example, in some embodiments, $X^2$ is a substituted or unsubstituted group selected from among $C_1$-$C_6$alkylene, $C_2$-$C_6$alkenylene, $C_1$-$C_6$fluoroalkylene, $C_2$-$C_6$fluoroalkenylene, and $C_1$-$C_6$heteroalkylene. In other embodiments, $X^2$ is a substituted or unsubstituted group selected from among $C_1$-$C_6$alkylene, and $C_2$-$C_6$alkenylene. In some embodiments, $X^2$ is —CH$_2$—, —CH$_2$CH$_2$—, —CH (CH$_3$)—, —(CH$_2$)$_3$—, or —CH$_2$CH=CH—. In some embodiments, $X^2$ is —CH$_2$—.

In some embodiments, $R^2$ is an optionally substituted group selected from among phenyl, naphthyl, monocyclic heteroaryl, bicyclic heteroaryl, $C_3$-$C_8$ cycloalkyl, monocyclic heterocycloalkyl, and bicyclic heterocycloalkyl. In other embodiments, $R^2$ is an optionally substituted group selected from among phenyl, naphthyl, (monocyclic heteroaryl containing 0-2 N atoms, 0-1 O atoms, and 0-1 S atoms), (bicyclic heteroaryl containing 0-2 N atoms, 0-1 O atoms, and 0-1 S atoms), $C_3$-$C_8$ cycloalkyl, monocyclic heterocycloalkyl containing 0-2 N atoms, and bicyclic heterocycloalkyl 0-2 N atoms; where if $R^2$ is substituted, then each substituent on $R^2$ is selected from among hydrogen, halogen, —CN, —NO$_2$, —S(=O)$_2$NH$_2$, —CO$_2$H, —CO$_2$R$^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —NR$^{10}$S(=)$_2$—R$^{11}$, —OC(=O)—R$^{11}$; —N(R$^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl; $R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, phenyl, and heteroaryl; $R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, phenyl, and heteroaryl.

In some embodiments, $R^2$ is an optionally substituted group selected from among phenyl, naphthyl, (monocyclic heteroaryl containing 0-2 N atoms, 0-1 O atoms, and 0-1 S atoms), (bicyclic heteroaryl containing 0-2 N atoms, 0-1 O atoms, and 0-1 S atoms), $C_3$-$C_8$ cycloalkyl; where if $R^2$ is substituted, then each substituent on $R^2$ is selected from among hydrogen, halogen, —CN, —NO$_2$, —S(=O)$_2$NH$_2$, —CO$_2$H, —CO$_2$R$^{10}$, —C(=O)R$^{11}$, —S—R$^{11}$, —S(=O)—R$^{11}$, —S(=O)$_2$—R$^{11}$, —NR$^1$C(=O)—R$^{11}$, —C(=O)N(R$^{10}$)$_2$, —S(=O)$_2$N(R$^{10}$)$_2$, —NR$^1$S(=O)$_2$—R$^{11}$, —OC(=O)—R$^{11}$; —N(R$^{10}$)$_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl; $R^{10}$ is hydrogen, or a substituted or unsubstituted group selected from among $C_1$-$C_6$alkyl, $C_1$-$C_6$fluoroalkyl, $C_1$-$C_6$heteroalkyl, and phenyl; $R^{11}$ is a substituted or unsubstituted group selected from among $C_1$-$C_6$alkyl, $C_1$-$C_6$fluoroalkyl, and phenyl.

In some embodiments, $R^2$ is selected from among phenyl, 2-methylphenyl, 3-methylphenyl, 4-methylphenyl, 3,4-dimethylphenyl, 2-fluorophenyl, 3-fluorophenyl, 4-fluorophenyl, 3,4-difluorophenyl, 2-chlorophenyl, 3-chlorophenyl, 4-chlorophenyl, 3,4-dichlorophenyl, 3-methoxyphenyl, 3-methoxyphenyl, 4-methoxyphenyl, 3,5-dimethoxyphenyl, 3,4,5-trimethoxyphenyl, naphth-2-yl, cyclopentyl, cyclohexyl, cycloheptyl, 2-(trifluoromethyl)-phenyl, 3-(trifluoromethyl)-phenyl, 4-(trifluoromethyl)-phenyl, 2-(trifluoromethoxy)-phenyl, 3-(trifluoromethoxy)-phenyl, 4-(trifluoromethoxy)-phenyl, benzo[2,1,3]oxadiazol-5-yl, 3-fluoro-4-methoxyphenyl, 2-(difluoromethoxy)-phenyl, 3-(difluoromethoxy)-phenyl, 4-(difluoromethoxy)-phenyl, N-(t-butoxycarbonyl)piperidin-4-yl, piperidin-4-yl, N-methylsulfonyl-2-aminophenyl, N-methylsulfonyl-3-aminophenyl, N-methylsulfonyl-4-aminophenyl, N-phenylsulfonyl-2-aminophenyl, N-phenylsulfonyl-3-aminophenyl, N-phenylsulfonyl-4-aminophenyl, 2-nitrophenyl, 3-nitrophenyl, 4-nitrophenyl, 2-aminophenyl, 3-aminophenyl, 4-aminophenyl, 2-dimethylaminophenyl, 3-dimethylaminophenyl, 4-dimethylaminophenyl, N-acetyl-2-aminophenyl, N-acetyl-3-aminophenyl, N-acetyl-4-aminophenyl, N-benzoyl-2-aminophenyl, N-benzoyl-3-aminophenyl, and N-benzoyl-4-aminophenyl.

In other embodiments, $R^2$ is selected from among phenyl, 2-methylphenyl, 2-fluorophenyl, 3-fluorophenyl, 4-fluorophenyl, 2-chlorophenyl, 3-chlorophenyl, 4-chlorophenyl, 3,4-dichlorophenyl, 3-methoxyphenyl, 4-methoxyphenyl, 3,5-dimethoxyphenyl, 3,4,5-trimethoxyphenyl, naphth-2-yl, cyclohexyl, 4-(trifluoromethoxy)-phenyl, benzo[2,1,3]oxadiazol-5-yl, 3-methylphenyl, 4-methylphenyl, 3-fluoro-4-methoxy-phenyl, 4-(difluoromethoxy)-phenyl, N-(t-butoxycarbonyl)piperidin-4-yl, piperidin-4-yl, and N-methylsulfonyl-3-aminophenyl.

In some embodiments, $R^3$ is hydrogen, halogen, substituted or unsubstituted $C_1$-$C_6$alkyl, substituted or unsubstituted $C_2$-$C_6$alkenyl, substituted or unsubstituted $C_1$-$C_6$heteroalkyl, substituted or unsubstituted phenyl, or —X$^6$—R$^6$; X$^6$ is a $C_1$-$C_6$alkylene, $C_1$-$C_6$fluoroalkylene, $C_2$-$C_6$alkenylene, or $C_2$-$C_6$heteroalkylene; $R^6$ is hydrogen, halogen, —CN, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl, phenyl, heteroaryl, or —X$^7$—R$^7$; X$^7$ is a bond, —O—, —S—, —S(=O)—, —S(=O)$_2$—, —NR$^a$—, —C(=O)—, —C(=O)O—, —OC(=O)—, —NHC(=O)—, —C(=O)NR$^a$—, —S(=O)$_2$NR$^a$—, —NHS(=O)$_2$—, —OC(=O)NR$^a$—, —NHC(=O)O—, —OC(=O)O—, —NHC(=O)NR$^a$—; $R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl; $R^a$ is selected from among hydrogen, $C_1$-$C_6$alkyl, $C_2$-$C_6$alkenyl, hydroxy, $C_1$-$C_6$alkoxy, $C_1$-$C_6$fluoroalkoxy, $C_1$-$C_6$heteroalkyl; or $R^a$ and $R^7$ together with the N atom to which they are attached form a 5-, 6-, or 7-membered heterocycloalkyl.

In some embodiments, $R^3$ is hydrogen, halogen, substituted or unsubstituted $C_1$-$C_6$alkyl, or —X$^6$—R$^6$.

In some embodiments, X$^6$ is $C_1$-$C_6$alkylene; $R^6$ is hydrogen, halogen, —CN, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl containing 0-2 N atoms, phenyl, heteroaryl containing 0-2 N atoms, or —X$^7$—R$^7$; X$^7$ is a bond, —O—, —S—, —S(=O)—, —S(=O)$_2$—, —NR$^a$—, —C(=O)—, —C(=O)O—, —OC(=O)—, —NHC(=O)—, —C(=O)NR$^a$—, —S(=O)$_2$NR$^a$—, —NHS(=O)$_2$—; $R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl; $R^a$ is selected from among hydrogen, $C_1$-$C_6$alkyl, $C_2$-$C_6$alkenyl, hydroxy, $C_1$-$C_6$alkoxy, $C_1$-$C_6$fluoroalkoxy, $C_1$-$C_6$heteroalkyl; or $R^a$ and $R^7$ together with the N atom to which they are attached form a 5-, 6-, or 7-membered heterocycloalkyl.

In some embodiments, $R^6$ is —X$^7$—R$^7$.

In some embodiments, X$^7$ is a bond, —O—, —S—, —S(=O)—, —S(=O)$_2$—, —NR$^a$—, or —C(=O)—.

In some embodiments, $R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, phenyl, phenylC$_1$-$C_4$alkyl, heteroaryl, heteroarylC$_1$-$C_4$alkyl; $R^a$ is selected from among hydrogen, $C_1$-$C_6$alkyl, hydroxy, $C_1$-$C_6$alkoxy, $C_1$-$C_6$fluoroalkoxy, $C_1$-$C_6$heteroalkyl; or $R^a$ and $R^7$ together with the N atom to which they are attached form a 5-, or 6-membered heterocycloalkyl.

In some embodiments, X$^7$ is a bond, —O—, or —NR$^a$—. In some embodiments, X$^7$ is a bond, or —NR$^a$—.

In some embodiments, $R^a$ is selected from among hydrogen, $C_1$-$C_6$alkyl, hydroxy, $C_1$-$C_6$alkoxy, $C_1$-$C_6$heteroalkyl. In other embodiments, $R^a$ is selected from among hydrogen, $C_1$-$C_6$alkyl, and $C_1$-$C_6$heteroalkyl.

In some embodiments, $R^7$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, phenyl, phenylC$_1$-$C_4$alkyl, heteroaryl, heteroarylC$_1$-$C_4$alkyl; $R^a$ is selected from among hydrogen, $C_1$-$C_6$alkyl, hydroxy, $C_1$-$C_6$alkoxy, $C_1$-$C_6$heteroalkyl; or $R^a$ and $R^7$ together with the N atom to which they are attached form a 5-, or 6-membered heterocycloalkyl.

In some embodiments, $R^3$ is selected from among hydrogen, methyl, ethyl, propyl, benzyl, dimethylaminomethyl, N-morpholinomethyl, N-pyrrolidinomethyl, N-piperidinomethyl, and N-benzylaminomethyl. In some embodiments, $R^3$ is selected from among hydrogen, methyl, ethyl, propyl, benzyl, dimethylaminomethyl, N-morpholinomethyl, N-pyrrolidinomethyl, and N-benzylaminomethyl.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In one embodiment, provided herein is a 1,3-disubstituted-1H-indole-5-carboxylic acid hydroxyamide compound, wherein the substituent at the 1-position is $R^4$ and the substituent at the 3-position is $—X^5—R^5$, wherein:

$R^4$ is hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_1$-$C_6$fluoroalkoxy, substituted or unsubstituted $C_1$-$C_6$heteroalkyl, substituted or unsubstituted phenyl, or $—X—R^8$;

$X^8$ is a $C_2$-$C_6$alkylene, $C_2$-$C_6$fluoroalkylene, $C_2$-$C_6$alkenylene, or $C_2$-$C_6$heteroalkylene;

$R^8$ is hydrogen, halogen, $—CN$, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl, phenyl, heteroaryl, or $—X^9—R^9$;

$X^9$ is a bond, $—O—$, $—S—$, $—S(=O)—$, $—S(=O)_2—$, $—NR^a—$, $—C(=O)—$, $—C(=O)O—$, $—OC(=O)—$, $—NHC(=O)—$, $—C(=O)NR^a—$, $—S(=O)_2NR^a—$, $—NHS(=O)_2—$, $—OC(=O)NR^a—$, $—NHC(=O)O—$, $—OC(=O)O—$, $—NHC(=O)NR^a—$;

$R^9$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl, $R^a$ is selected from among hydrogen, $C_1$-$C_6$alkyl, $C_2$-$C_6$alkenyl, hydroxy, $C_1$-$C_6$alkoxy, $C_1$-$C_6$fluoroalkoxy, $C_1$-$C_6$heteroalkyl; or $R^a$ and $R^9$ together with the N atom to which they are attached form a 5-, 6-, or 7-membered heterocycloalkyl;

$X^5$ is a bond, or a substituted or unsubstituted group selected from among $C_1$-$C_6$alkylene, $C_2$-$C_6$alkenylene, $C_2$-$C_6$ alkynylene, $C_1$-$C_6$fluoroalkylene, $C_2$-$C_6$fluoroalkenylene, $C_1$-$C_6$haloalkylene, $C_2$-$C_6$haloalkenylene, $C_1$-$C_6$heteroalkylene, $—C(=O)—$, and $—C(=O)—C_1$-$C_6$alkylene;

$R^5$ is a substituted or unsubstituted group selected from among aryl, heteroaryl, $C_3$-$C_8$cycloalkyl, and heterocycloalkyl;

where if $R^5$ is substituted, then each substituent on $R^5$ is selected from among hydrogen, halogen, $—CN$, $—NO_2$, $—S(=O)_2NH_2$, $—CO_2H$, $—CO_2R^{10}$, $—C(=O)R^{11}$, $—S—R^{11}$, $—S(=O)—R^{11}$, $—S(=O)_2—R^{11}$, $—NR^{10}C(=O)—R^{11}$, $—C(=O)N(R^{10})_2$, $—S(=O)_2N(R^{10})_2$, $—NR^{10}S(=O)_2—R^{11}$, $—OC(=O)N(R^{10})_2$, $—NR^{10}C(=O)O—R^{11}$, $—OC(=O)O—R^{11}$, $—NHC(=O)NH—R^{11}$, $—OC(=O)—R^{11}$; $—N(R^{10})_2$, substituted or unsubstituted $C_1$-$C_6$alkyl, $C_1$-$C_6$fluoroalkyl, substituted or unsubstituted $C_2$-$C_6$alkenyl, substituted or unsubstituted $C_2$-$C_6$alkynyl, substituted or unsubstituted $C_1$-$C_6$alkoxy, $C_1$-$C_6$ fluoroalkoxy, substituted or unsubstituted $C_1$-$C_6$heteroalkyl, substituted or unsubstituted $C_3$-$C_8$cycloalkyl, substituted or unsubstituted heterocycloalkyl, substituted or unsubstituted aryl, and substituted or unsubstituted heteroaryl;

$R^{10}$ is hydrogen, or a substituted or unsubstituted group selected from among $C_1$-$C_6$alkyl, $C_1$-$C_6$fluoroalkyl, $C_1$-$C_6$heteroalkyl, $C_3$-$C_8$cycloalkyl, $C_2$-$C_8$heterocycloalkyl, aryl, and heteroaryl;

$R^{11}$ is a substituted or unsubstituted group selected from among $C_1$-$C_6$alkyl, $C_1$-$C_6$fluoroalkyl, $C_3$-$C_8$cycloalkyl, $C_2$-$C_8$heterocycloalkyl, aryl, and heteroaryl;

or an active metabolite, pharmaceutically acceptable solvate, pharmaceutically acceptable salt, pharmaceutically acceptable N-oxide, or pharmaceutically acceptable prodrug thereof.

For any and all of the embodiments, substituents can be selected from among from a subset of the listed alternatives. For example, in some embodiments, $R^4$ is hydrogen, substituted or unsubstituted $C_1$-$C_6$alkyl, substituted or unsubstituted $C_2$-$C_6$alkenyl, substituted or unsubstituted $C_1$-$C_6$alkoxy, substituted or unsubstituted $C_1$-$C_6$heteroalkyl, substituted or unsubstituted phenyl, or $—X—R^8$; $X^8$ is a $C_2$-$C_6$alkylene, $C_2$-$C_6$fluoroalkylene, $C_2$-$C_6$alkenylene, or $C_2$-$C_6$heteroalkylene; $R^8$ is hydrogen, halogen, $—CN$, hydroxy, amino, $C_1$-$C_6$alkylamino, di($C_1$-$C_6$alkyl)amino, $C_1$-$C_6$alkoxy, $C_3$-$C_8$cycloalkyl, $C_2$-$C_8$heterocycloalkyl, phenyl, heteroaryl, or $—X^9—R^9$; $X^9$ is a bond, $—O—$, $—S—$, $—NR^a—$, $C(=O)—$; $R^9$ is hydrogen, $C_1$-$C_6$alkyl, $C_2$-$C_6$alkenyl, $C_1$-$C_6$heteroalkyl, $C_1$-$C_6$haloalkyl, $C_3$-$C_8$cycloalkyl, cycloalkylalkyl, $C_2$-$C_8$heterocycloalkyl, heterocycloalkylalkyl, aryl, arylalkyl, heteroaryl, heteroarylalkyl; $R^a$ is selected from among hydrogen, $C_1$-$C_6$alkyl, $C_2$-$C_6$alkenyl, hydroxy, $C_1$-$C_6$alkoxy, and $C_1$-$C_6$heteroalkyl; or $R^a$ and $R^9$ together with the N atom to which they are attached form a 5-, or 6-membered heterocycloalkyl.

In other embodiments, $R^4$ is hydrogen, substituted or unsubstituted $C_1$-$C_6$alkyl, substituted or unsubstituted $C_1$-$C_6$heteroalkyl, substituted or unsubstituted phenyl, or $—X—R^8$; $X^8$ is a $C_2$-$C_6$alkylene; $R^8$ is hydrogen, halogen, $—CN$, hydroxy, amino, $C_1$-$C_6$alkylamino, di($C_1$-$C_6$alkyl) amino, $C_1$-$C_6$alkoxy, $C_3$-$C_8$cycloalkyl, $C_2$-$C_8$heterocycloalkyl, phenyl, heteroaryl, or $—X^9—R^9$; $X^9$ is a bond, $—O—$, $—S—$, $—NR^a—$, $—C(=O)—$; $R^9$ is hydrogen, $C_1$-$C_6$alkyl, $C_1$-$C_6$heteroalkyl, $C_1$-$C_6$haloalkyl, $C_2$-$C_8$heterocycloalkyl, heterocycloalkylalkyl, phenyl, phenylalkyl, heteroaryl, heteroarylalkyl; $R^a$ is selected from among hydrogen, $C_1$-$C_6$alkyl, hydroxy, $C_1$-$C_6$alkoxy; or $R^a$ and $R^9$ together with the N atom to which they are attached form a 5-, or 6-membered heterocycloalkyl.

In some embodiments, $R^4$ is selected from among hydrogen, methyl, ethyl, propyl, isopropyl, phenyl, and benzyl.

In some embodiments, $X^5$ is a bond, or a substituted or unsubstituted group selected from among $C_1$-$C_6$alkylene, $C_2$-$C_6$alkenylene, $C_1$-$C_6$fluoroalkylene, and $C_1$-$C_6$heteroalkylene. In other embodiments, $X^5$ is a bond, or a substituted or unsubstituted $C_1$-$C_6$alkylene. In some embodiments, $X^5$ is $—CH_2—$, $—CH_2CH_2—$, $—CH(CH_3)—$, $—(CH_2)_3—$, or $—CH_2CH=CH—$. In some embodiments, $X^5$ is $—CH_2—$.

In some embodiments, $R^5$ is a substituted or unsubstituted group selected from among phenyl, naphthyl, (heteroaryl containing 0-2 N atoms, 0-1 O atoms, 0-1 S atoms), $C_3$-$C_8$cycloalkyl, and heterocycloalkyl containing 0-2 N atoms.

In some embodiments, if $R^5$ is substituted, then each substituent on $R^5$ is selected from among hydrogen, halogen, $—CN$, $—NO_2$, $—S(=O)_2NH_2$, $—CO_2H$, $—CO_2R^{10}$, —C(=O)R$^{11}$, —S—R$^{11}$, —S(=O)—R$^{11}$, —S(=O)$_2$—R$^{11}$, —NR$^{10}$C(=O)—R$^{11}$, —C(=O)N(R$^{10}$)$_2$, —S(=O)$_2$N(R$^{10}$)$_2$, —NR$^{10}$S(=)$_2$—R$^{11}$, —OC(=O)—R$^{11}$; —N(R$^{10}$)$_2$, substituted or unsubstituted C$_1$-C$_6$alkyl, C$_1$-C$_6$fluoroalkyl, substituted or unsubstituted C$_2$-C$_6$alkenyl, substituted or unsubstituted C$_1$-C$_6$alkoxy, C$_1$-C$_6$ fluoroalkoxy, substituted or unsubstituted C$_1$-C$_6$heteroalkyl, substituted or unsubstituted heterocycloalkyl, substituted or unsubstituted phenyl, and substituted or unsubstituted heteroaryl; R$^{10}$ is hydrogen, or a substituted or unsubstituted group selected from among C$_1$-C$_6$alkyl, C$_1$-C$_6$fluoroalkyl, C$_1$-C$_6$heteroalkyl, phenyl, and heteroaryl; R$^{11}$ is a substituted or unsubstituted group selected from among C$_1$-C$_6$alkyl, C$_1$-C$_6$fluoroalkyl, phenyl, and heteroaryl.

In some embodiments, R$^5$ is a substituted or unsubstituted group selected from among phenyl, naphthyl, (monocyclic heteroaryl containing 0-2 N atoms, 0-1 O atoms, 0-1 S atoms), and C$_2$-C$_8$heterocycloalkyl containing 0-2 N atoms.

In some embodiments, R$^5$ is selected from among phenyl, 2-methylphenyl, 3-methylphenyl, 4-methylphenyl, 3,4-dimethylphenyl, 2-fluorophenyl, 3-fluorophenyl, 4-fluorophenyl, 3,4-difluorophenyl, 2-chlorophenyl, 3-chlorophenyl, 4-chlorophenyl, 3,4-dichlorophenyl, 3-methoxyphenyl, 3-methoxyphenyl, 4-methoxyphenyl, 3,5-dimethoxyphenyl, 3,4,5-trimethoxyphenyl, naphth-2-yl, cyclopentyl, cyclohexyl, cycloheptyl, 2-(trifluoromethyl)-phenyl, 3-(trifluoromethyl)-phenyl, 4-(trifluoromethyl)-phenyl, 2-(trifluoromethoxy)-phenyl, 3-(trifluoromethoxy)-phenyl, 4-(trifluoromethoxy)-phenyl, benzo[2,1,3]oxadiazol-5-yl, 3-fluoro-4-methoxyphenyl, 2-(difluoromethoxy)-phenyl, 3-(difluoromethoxy)-phenyl, 4-(difluoromethoxy)-phenyl, N-(t-butoxycarbonyl)piperidin-4-yl, piperidin-4-yl, N-methylsulfonyl-2-aminophenyl, N-methylsulfonyl-3-aminophenyl, N-methylsulfonyl-4-aminophenyl, N-phenylsulfonyl-2-aminophenyl, N-phenylsulfonyl-3-aminophenyl, N-phenylsulfonyl-4-aminophenyl, 2-nitrophenyl, 3-nitrophenyl, 4-nitrophenyl, 2-aminophenyl, 3-aminophenyl, 4-aminophenyl, 2-dimethylaminophenyl, 3-dimethylaminophenyl, 4-dimethylaminophenyl, N-acetyl-2-aminophenyl, N-acetyl-3-aminophenyl, N-acetyl-4-aminophenyl, 2-(phenylcarbonylamino)-phenyl, 3-(phenylcarbonylamino)-phenyl, and 4-(phenylcarbonylamino)-phenyl. In some embodiments, R$^5$ is selected from among phenyl, 4-nitrophenyl, 4-aminophenyl, 4-(phenylcarbonylamino)-phenyl, 4-fluorophenyl, and 4-(t-butoxycarbonyl)piperazin-1-yl.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In another aspect, provided herein is a compound having a structure selected from among Formula (Ia) and (IIa):

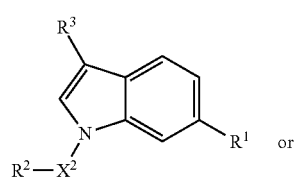

Ia

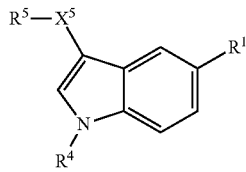

IIa wherein:
R$^1$ is —C(O)NHOH;
X$^2$ is a bond, alkylene, or alkenylene, where the alkylene or alkenylene is optionally substituted with one, two, three, four, or five halo;
R$^2$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;
R$^3$ is hydrogen, alkyl, substituted alkyl, alkenyl, substituted alkenyl, hydroxy, alkoxy, or haloalkoxy;
R$^4$ is hydrogen, alkyl, substituted alkyl, alkenyl, substituted alkenyl, hydroxy, alkoxy, haloalkoxy, or optionally substituted phenyl;
X$^5$ is a bond, alkylene, or alkenylene where the alkylene or alkenylene is optionally substituted with halo; and
R$^5$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or
an active metabolite, pharmaceutically acceptable solvate, pharmaceutically acceptable salt, pharmaceutically acceptable N-oxide, or pharmaceutically acceptable prodrug thereof.

In another embodiment, provided herein is a compound having a structure selected from among Formula Ib or IIb:

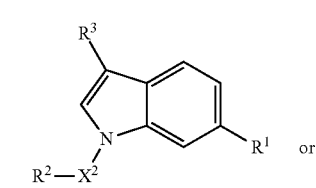

Ib

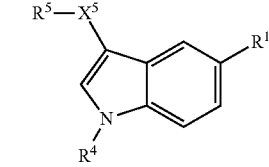

IIb wherein:
R$^1$ is —C(O)NHOH;
X$^2$ is a bond, alkylene, or alkenylene where the alkylene or alkenylene is optionally substituted with one, two, three, four, or five halo;

R² is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro;

R³ is hydrogen, alkenyl, substituted alkenyl, hydroxy, alkoxy, haloalkoxy, or —X⁶—R⁶ where X⁶ is alkylene or alkenylene and X⁶ is additionally optionally substituted with one, two, three, four, of five halo; and R⁶ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NR$^a$R$^b$ (where R$^a$ and R$^b$ are independently hydrogen, alkyl, substituted alkyl, alkenyl, alkynyl, substituted alkynyl, hydroxy, alkoxy, or alkenyloxy);

R⁴ is hydrogen, alkyl, substituted alkyl, alkenyl, substituted alkenyl, hydroxy, alkoxy, haloalkoxy, or optionally substituted phenyl; and X⁵ is a bond; and R⁵ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the phenyl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; provided that R⁵ is not optionally substituted pyrrole or optionally substituted 2,5-dioxo-pyrrole; or X⁵ is alkylene or alkenylene where the alkylene or alkenylene is optionally substituted with halo; and R⁵ is aryl, cycloalkyl, heteroaryl, or heterocycloalkyl where the cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the aryl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or an active metabolite, pharmaceutically acceptable solvate, pharmaceutically acceptable salt, pharmaceutically acceptable N-oxide, or pharmaceutically acceptable prodrug thereof.

In one embodiment, provided herein is a compound of Formula (Ia).

In another embodiment, provided herein is a compound of Formula (Ib).

In yet another embodiment, provided herein is a compound of Formula (IIa).

In a further embodiment, provided herein is a compound of Formula (IIb).

For any and all of the embodiments, substituents can be selected from among from a subset of the listed alternatives. For example, in some embodiments, X² is a bond, alkylene, or alkenylene where the alkylene or alkenylene is optionally substituted with one, two, three, four, or five halogens. In another embodiment, X² is alkylene or alkenylene. In other embodiments, X² is —CH₂—, —CH₂CH₂—, —CH(CH₃)—, —(CH₂)₃—, or —CH₂CH=CH—. In some embodiments, X² is —CH₂—.

In some embodiments, R² is aryl, cycloalkyl, heteroaryl, or heterocycloalkyl where the aryl, cycloalkyl, heteroaryl, and heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro. In other embodiments, R² is aryl, cycloalkyl, heteroaryl, or heterocycloalkyl, where the aryl, cycloalkyl, heteroaryl, and heterocycloalkyl are optionally substituted with one, two, or three substituents selected from among alkyl, alkoxy, alkoxycarbonyl, halogen, and haloalkoxy. In some other embodiments, R² is aryl, cycloalkyl, heteroaryl, or heterocycloalkyl, where the aryl is optionally substituted with one, two, or three substituents selected from among alkyl, alkoxy, halo, and haloalkoxy, and the heterocycloalkyl is optionally substituted with alkoxycarbonyl. In further embodiments, R² is cyclohexyl, benzooxadiazolyl, naphth-2-yl, phenyl, or piperidinyl, where the phenyl is optionally substituted with one, two, or three substituents selected from among methyl, methoxy, chloro, fluoro, trifluoromethoxy, and difluoromethoxy, and the piperidinyl is optionally substituted with t-butoxycarbonyl. In yet other embodiments, R² is cyclohexyl, benzo[2,1,3]oxadiazol-5-yl, phenyl, naphth-2-yl, 2-methylphenyl, 3-methylphenyl, 4-methylphenyl, 3-methoxyphenyl, 4-methoxyphenyl, 3,5-dimethoxyphenyl, 3,4,5-trimethoxyphenyl, 2-chlorophenyl, 3-chlorophenyl, 4-chlorophenyl, 3,4-dichlorophenyl, 2-fluorophenyl, 3-fluorophenyl, 4-fluorophenyl, 4-(difluoromethoxy)-phenyl, 4-(trifluoromethoxy)-phenyl, 3-fluoro-4-methoxy-phenyl, piperidin-4-yl, or N-(t-butoxycarbonyl)piperidin-4-yl.

In some embodiments, R² is benzo[2,1,3]oxadiazol-5-yl, 4-methoxyphenyl, 4-chlorophenyl, 4-(difluoromethoxy)-phenyl, or 3-fluoro-4-methoxy-phenyl.

In some embodiments, $R^3$ is hydrogen, alkyl, substituted alkyl, alkenyl, substituted alkenyl, hydroxy, alkoxy, or haloalkoxy. In other embodiments, $R^3$ is hydrogen.

In some embodiments, $R^4$ is hydrogen, alkyl, substituted alkyl, alkenyl, substituted alkenyl, hydroxy, alkoxy, haloalkoxy, or optionally substituted phenyl. In yet other embodiments, $R^4$ is alkyl or optionally substituted phenyl. In some other embodiments, $R^4$ is methyl, ethyl, isopropyl, or phenyl. In some embodiments, $R^4$ is methyl, ethyl, or isopropyl.

In some embodiments, $X^5$ is a bond, alkylene, or alkenylene where the alkylene or alkenylene is optionally substituted with halo. In other embodiments, $X^5$ is alkylene. In yet other embodiments, $X^5$ is —$CH_2$—.

In some embodiments, $R^5$ is aryl, cycloalkyl, heteroaryl, or heterocycloalkyl where the aryl, cycloalkyl, heteroaryl, and heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro.

In yet other embodiments, $R^5$ is heterocycloalkyl optionally substituted with alkoxycarbonyl or $R^5$ is aryl optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro.

In some embodiments, $R^5$ is piperazinyl optionally substituted with t-butoxycarbonyl, or $R^5$ is phenyl optionally substituted with one, two, or three substituents selected from among acylamino, amino, halogen, and nitro. In some other embodiments, $R^5$ is 4-(t-butoxycarbonyl)piperazin-1-yl, phenyl, 4-aminophenyl, 4-(phenylcarbonylamino)-phenyl, 4-fluorophenyl, or 4-nitrophenyl. In yet other embodiments, $R^5$ is phenyl, 4-aminophenyl, 4-(phenylcarbonylamino)-phenyl, 4-fluorophenyl, or 4-nitrophenyl.

In some embodiments, $R^2$ is aryl, cycloalkyl, heteroaryl, or heterocycloalkyl, where the aryl is substituted with one, two, or three substituents selected from among acyloxy, alkyl, substituted alkyl, alkenyl, substituted alkenyl, alkylamino, dialkylamino, and haloalkoxy; where the cycloalkyl is optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro; and where the heteroaryl and the heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, and nitro. In other embodiments, $R^2$ is aryl, cycloalkyl, heteroaryl, or heterocycloalkyl where the aryl is substituted with one, two, or three substituents selected from among alkyl and haloalkoxy, and the heterocycloalkyl is optionally substituted with alkoxycarbonyl. In yet other embodiments, $R^2$ is cyclohexyl; benzooxadiazolyl; phenyl substituted with one, two, or three substituents selected from among methyl, trifluoromethoxy, or difluoromethoxy; or piperidinyl optionally substituted with t-butoxycarbonyl.

In some embodiments, $R^2$ is cyclohexyl, benzo[2,1,3]oxadiazol-5-yl, 2-methylphenyl, 3-methylphenyl, 4-methylphenyl, 4-(difluoromethoxy)-phenyl, 4-(trifluoromethoxy)-phenyl, N-(t-butoxycarbonyl)piperidin-4-yl, or piperidin-4-yl. In yet other embodiments, $R^2$ is benzo[2,1,3]oxadiazol-5-yl or 4-(difluoromethoxy)-phenyl.

In some embodiments, $R^3$ is hydrogen, alkenyl, substituted alkenyl, hydroxy, alkoxy, haloalkoxy, or —$X^6$—$R^6$, where $X^6$ is alkylene or alkenylene and $X^6$ is additionally optionally substituted with one, two, three, four, or five halogens; and $R^6$ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkylcarbonyloxy, alkyl-$S(O)_{0-2}$—, alkenyl-$S(O)_{0-2}$—, aminosulfonyl, alkylaminosulfonyl, dialkylaminosulfonyl, alkylsulfonyl-$NR^c$—(where $R^c$ is hydrogen, alkyl, substituted alkyl, alkenyl, substituted alkenyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —$C(O)NR^aR^b$ (where $R^a$ and $R^b$ are independently hydrogen, alkyl, substituted alkyl, alkenyl, alkynyl, substituted alkynyl, hydroxy, alkoxy, or alkenyloxy). In some embodiments, $R^3$ is hydrogen.

In some embodiments, $X^5$ is a bond; and $R^5$ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, or nitro; and the phenyl is substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro; provided that $R^5$ is not optionally substituted pyrrole or optionally substituted 2,5-dioxo-pyrrole; or $X^5$ is alkylene or alkenylene where the alkylene or alkenylene is optionally substituted with halogen; and $R^5$ is aryl, cycloalkyl, heteroaryl, or heterocycloalkyl where the cycloalkyl, heteroaryl, and heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro; and the aryl is substituted with one, two, or three susbtituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro.

In some embodiments, $X^5$ is alkylene or alkenylene; and $R^5$ is aryl substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro. In other embodiments, $R^5$ is phenyl substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro. In some other embodiments, $R^5$ is phenyl substituted with one, two, or three substituents selected from among optionally substituted arylcarbonylamino, amino, halo, and nitro. In yet other embodiments, $R^5$ is 4-(phenylcarbonylamino)-phenyl, 4-aminophenyl, 4-fluorophenyl, or 4-nitrophenyl.

In some embodiments, $R^3$ is hydrogen; $X^2$ is alkylene or alkenylene; and $R^2$ is aryl, cycloalkyl, or heteroaryl, where the aryl, cycloalkyl, and heteroaryl are optionally substituted with one, two, or three substituents selected from among alkyl, alkoxy, alkoxycarbonyl, halogen, and haloalkoxy. In other embodiments, $R^3$ is hydrogen; $X^2$ is alkylene or alkenylene; and $R^2$ is naphthyl, phenyl, cycloalkyl, heteroaryl, or heterocycloalkyl optionally substituted with methyl, methoxy, t-butoxycarbonyl, chloro, fluoro, trifluoromethoxy, or difluoromethoxy. In some other embodiments, $R^3$ is hydrogen; $X^2$ is alkylene or alkenylene; and $R^2$ is phenyl where the phenyl is optionally substituted with one, two, or three substituents selected from among methyl, methoxy, chloro, fluoro, trifluoromethoxy, and difluoromethoxy; or $R^2$ is benzooxadiazolyl.

In some embodiments, $R^4$ is hydrogen or alkyl; $X^5$ is alkylene or alkenylene; and $R^5$ is aryl optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro; or $R^5$ is heterocycloalkyl optionally substituted with alkoxycarbonyl. In other embodiments, $R^4$ is alkyl; $X^5$ is alkylene; and $R^5$ is phenyl optionally substituted with one, two, or three substituents selected from among acylamino, amino, halogen, and nitro.

In some embodiments, $R^3$ is hydrogen; $X^2$ is alkylene or alkenylene; and $R^2$ is cycloalkyl, aryl, heteroaryl, or heterocycloalkyl, where the cycloalkyl is optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro; where the aryl is substituted with one, two, or three substituents selected from among acyloxy, alkyl, substituted alkyl, alkenyl, substituted alkenyl, alkylamino, dialkylamino, and haloalkoxy; where the heteroaryl and heterocycloalkyl are optionally substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, and nitro.

In some embodiments, $R^3$ is hydrogen; $X^2$ is alkylene or alkenylene; and $R^2$ is cycloalkyl; phenyl substituted with one, two, or three alkyl or haloalkoxy; benzooxadiazolyl; or piperdinyl optionally substituted with alkoxycarbonyl. In some other embodiments, $R^3$ is hydrogen; $X^2$ is alkylene or alkenylene; and $R^2$ is benzooxadiazolyl or phenyl where the phenyl is substituted with one, two, or three substituents selected from among methyl, chloro, fluoro, trifluoromethoxy, or difluoromethoxy.

In some embodiments, $R^4$ is hydrogen or alkyl; $X^5$ is a bond and $R^5$ is heterocycloalkyl optionally substituted with alkoxycarbonyl; or $X^5$ is alkylene or alkenylene and $R^5$ is aryl substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halogen, haloalkoxy, and nitro.

In yet other embodiments, $R^4$ is hydrogen or alkyl; $X^5$ is alkylene; and $R^5$ is phenyl substituted with one, two, or three substituents selected from among acyl, acylamino, acyloxy, alkyl, substituted alkyl, alkenyl, substituted alkenyl, alkoxy, alkoxycarbonyl, amino, alkylamino, dialkylamino, carboxy, cyano, halogen, haloalkoxy, and nitro. In yet other embodiments, $R^4$ is hydrogen or alkyl; $X^5$ is alkylene; and $R^5$ is phenyl substituted with one, two, or three substituents selected from among optionally substituted arylcarbonylamino, amino, halogen, and nitro.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Further embodiments of compounds described herein (e.g. 1,3-disubstituted-1H-indole-6-carboxylic acid hydroxyamide compounds, 1,3-disubstituted-1H-indole-5-carboxylic acid hydroxyamide compounds, compounds of Formula (I), Formula (Ia), Formula (Ib), Formula (IIa), Formula (IIb)) include, but are not limited to, compounds in Tables 1 and 2.

TABLE 1

1,3-substituted-1H-indole-6-carboxylic acid hydroxyamides.

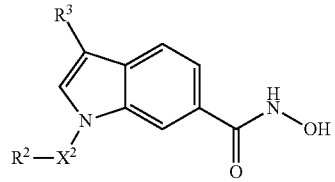

| Compound No. | $R^2$ | $R^3$ | $X^2$ |
|---|---|---|---|
| 1. | 3,4-dichlorophenyl | H | —CH$_2$— |
| 2. | 2-methylphenyl | H | —CH$_2$— |
| 3. | 3,4,5-trimethoxyphenyl | H | —CH$_2$— |
| 4. | 3-fluorophenyl | H | —CH$_2$— |
| 5. | 3-methylphenyl | H | —CH$_2$— |
| 6. | phenyl | H | —CH$_2$— |
| 7. | 3,5-dimethoxyphenyl | H | —CH$_2$— |
| 8. | phenyl | H | —CH(CH$_3$)— |
| 9. | 4-fluorophenyl | H | —CH$_2$— |
| 10. | 2-fluorophenyl | H | —CH$_2$— |
| 11. | 2-chlorophenyl | H | —CH$_2$— |
| 12. | 3-methoxyphenyl | H | —CH$_2$— |
| 13. | naphth-2-yl | H | —CH$_2$— |
| 14. | phenyl | H | —(CH$_2$)$_3$— |
| 15. | cyclohexyl | H | —CH$_2$— |
| 16. | phenyl | H | —CH=CHCH$_2$— |
| 17. | 4-(trifluoromethoxy)phenyl | H | —CH$_2$— |
| 18. | 4-chlorophenyl | H | —CH$_2$— |
| 19. | benzo[2,1,3]oxadiazol-5-yl | H | —CH$_2$— |
| 20. | 4-methylphenyl | H | —CH$_2$— |
| 21. | 3-fluoro-4-methoxyphenyl | H | —CH$_2$— |
| 22. | 4-(difluoromethoxy)phenyl | H | —CH$_2$— |

TABLE 1-continued 1,3-substituted-1H-indole-6-carboxylic acid hydroxyamides.

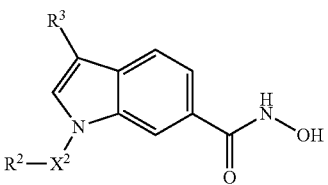

| Compound No. | R² | R³ | X² |
|---|---|---|---|
| 23. | 4-methoxyphenyl | H | —CH₂— |
| 24. | phenyl | H | —CH₂CH₂— |
| 25. | 3-chlorophenyl | H | —CH₂— |
| 26. | N-(t-butoxycarbonyl)piperidin-4-yl | H | —CH₂— |
| 27. | piperidin-4-yl | H | —CH₂— |
| 28. | N-methylsulfonyl-3-aminophenyl | H | —CH₂— |
| 29. | 4-methoxyphenyl | dimethylaminomethyl | —CH₂— |
| 30. | 4-methoxyphenyl | N-morpholinomethyl | —CH₂— |
| 31. | 4-methoxyphenyl | N-pyrrolidinomethyl | —CH₂— |
| 32. | 4-methoxyphenyl | N-benzylaminomethyl | —CH₂— |
| 33. | 4-methoxyphenyl | ethyl | —CH₂— |

Compounds in Table 1 are named:
1-(3,4-dichloro-phenylmethyl)-1H-indole-6-carboxylic acid hydroxyamide (Compound 1);
1-(2-methyl-phenylmethyl)-1H-indole-6-carboxylic acid hydroxyamide (Compound 2);
1-(3,4,5-trimethoxy-phenylmethyl)-1H-indole-6-carboxylic acid hydroxyamide (Compound 3);
1-(3-fluoro-phenylmethyl)-1H-indole-6-carboxylic acid hydroxyamide (Compound 4);
1-(3-methyl-phenylmethyl)-1H-indole-6-carboxylic acid hydroxyamide (Compound 5);
1-(benzyl)-1H-indole-6-carboxylic acid hydroxyamide (Compound 6);
1-(3,5-dimethoxy-phenylmethyl)-1H-indole-6-carboxylic acid hydroxyamide (Compound 7);
1-(1-methyl-1-phenylmethyl)-1H-indole-6-carboxylic acid hydroxyamide (Compound 8);
1-(4-fluoro-phenylmethyl)-1H-indole-6-carboxylic acid hydroxyamide (Compound 9);
1-(2-fluoro-phenylmethyl)-1H-indole-6-carboxylic acid hydroxyamide (Compound 10);
1-(2-chloro-phenylmethyl)-1H-indole-6-carboxylic acid hydroxyamide (Compound 11);
1-(3-methoxy-phenylmethyl)-1H-indole-6-carboxylic acid hydroxyamide (Compound 12);
1-(naphth-2-ylmethyl)-1H-indole-6-carboxylic acid hydroxyamide (Compound 13);
1-(3-phenylpropyl)-1H-indole-6-carboxylic acid hydroxyamide (Compound 14);
1-(cyclohexylmethyl)-1H-indole-6-carboxylic acid hydroxyamide (Compound 15);
1-[1-(phenyl)-propen-3-yl]-1H-indole-6-carboxylic acid hydroxyamide (Compound 16);
1-[4-(trifluoromethoxy)-phenylmethyl]-1H-indole-6-carboxylic acid hydroxyamide (Compound 17);
1-(4-chloro-phenylmethyl)-1H-indole-6-carboxylic acid hydroxyamide (Compound 18);
1-(benzo[2,1,3]oxadiazol-5-ylmethyl)-1H-indole-6-carboxylic acid hydroxyamide (Compound 19);
1-(4-methyl-phenylmethyl)-1H-indole-6-carboxylic acid hydroxyamide (Compound 20);
1-(3-fluoro-4-methoxy-phenylmethyl)-1H-indole-6-carboxylic acid hydroxyamide (Compound 21);
1-[4-(difluoromethoxy)-phenylmethyl]-1H-indole-6-carboxylic acid hydroxyamide (Compound 22);
1-(4-methoxy-phenylmethyl)-1H-indole-6-carboxylic acid hydroxyamide (Compound 23);
1-(phenethyl)-1H-indole-6-carboxylic acid hydroxyamide (Compound 24);
1-(3-chloro-phenylmethyl)-1H-indole-6-carboxylic acid hydroxyamide (Compound 25);
1-[N-(t-butoxycarbonyl)piperidin-4-ylmethyl]-1H-indole-6-carboxylic acid hydroxyamide (Compound 26);
1-(piperidin-4-ylmethyl)-1H-indole-6-carboxylic acid hydroxyamide (Compound 27);
1-(N-methylsulfonyl-3-aminobenzyl)-1H-indole-6-carboxylic acid hydroxyamide (Compound 28);
3-(Dimethylaminomethyl)-1-(4-methoxybenzyl)-1H-indole-6-carboxylic acid hydroxyamide (Compound 29);
3-(N-Morpholinomethyl)-1-(4-methoxybenzyl)-1H-indole-6-carboxylic acid hydroxyamide (Compound 30);
3-(N-Pyrrolidinomethyl)-1-(4-methoxybenzyl)-1H-indole-6-carboxylic acid hydroxyamide (Compound 31);
3-(N-Benzylaminomethyl)-1-(4-methoxybenzyl)-1H-indole-6-carboxylic acid hydroxyamide (Compound 32); and
3-(Ethyl)-1-(4-methoxybenzyl)-1H-indole-6-carboxylic acid hydroxyamide (Compound 33).

TABLE 2

1,3-substituted-1H-indole-5-carboxylic acid hydroxyamides

| Compound No. | R⁴ | X⁵ | R⁵ |
|---|---|---|---|
| 34. | methyl | —CH₂— | 4-nitrophenyl |
| 35. | ethyl | —CH₂— | phenyl |
| 36. | methyl | —CH₂— | 4-(phenylcarbonylamino)-phenyl |
| 37. | isopropyl | —CH₂— | phenyl |
| 38. | methyl | —CH₂— | 4-aminophenyl |
| 39. | methyl | —CH₂— | 4-fluorophenyl |
| 40. | phenyl | —CH₂— | phenyl |
| 41. | methyl | —CH₂— | 4-(t-butoxycarbonyl)piperazin-1-yl |

Compounds in Table 2. are named:
1-methyl-3-(4-nitro-phenylmethyl)-1H-indole-5-carboxylic acid hydroxyamide (Compound 34);
1-ethyl-3-(phenylmethyl)-1H-indole-5-carboxylic acid hydroxyamide (Compound 35);
1-methyl-3-[4-(phenylcarbonylamino)-phenylmethyl]-1H-indole-5-carboxylic acid hydroxyamide (Compound 36);
1-isopropyl-3-(phenylmethyl)-1H-indole-5-carboxylic acid hydroxyamide (Compound 37);
1-methyl-3-(4-amino-phenylmethyl)-1H-indole-5-carboxylic acid hydroxyamide (Compound 38);
1-methyl-3-(4-fluoro-phenylmethyl)-1H-indole-5-carboxylic acid hydroxyamide (Compound 39);
1-phenyl-3-(phenylmethyl)-1H-indole-5-carboxylic acid hydroxyamide (Compound 40); and 1-methyl-3-[4-(t-butoxycarbonyl)piperazin-1-ylmethyl]-1H-indole-5-carboxylic acid hydroxyamide (Compound 41).

Throughout the specification, groups and substituents thereof can be chosen by one skilled in the field to provide stable moieties and compounds.

Further Forms of Compounds

Compounds described herein may possess one or more stereocenters and each center may exist in the R or S configuration. The compounds presented herein include all diastereomeric, enantiomeric, and epimeric forms as well as the appropriate mixtures thereof. Separation of steroisomers may be performed by chromatography. Alternatively, individual stereoisomers may be obtained by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds described herein, dissociable complexes are also possible (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chiral chromatography, or by separation/resolution techniques based upon differences in solubility. The optically pure enantiomer(s) is/are then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981, herein incorporated by reference in its entirety. Stereoisomers may also be obtained by stereoselective synthesis.

In some situations, compounds may exist as tautomers. All tautomers are included within the formulas described herein.

The methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Indole compounds described herein in unoxidized form can be prepared from the corresponding N-oxides indole compounds by treating with a reducing agent, such as, but not limited to, sulfur, sulfur dioxide, triphenyl phosphine, lithium borohydride, sodium borohydride, phosphorus trichloride, phosphorus tribromide, or the like in a suitable inert organic solvent, such as, but not limited to, acetonitrile, ethanol, aqueous dioxane, or the like at 0 to 80° C.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) *Medicinal Chemistry A Biochemical Approach*, Oxford University Press, New York, pages 388-392; Silverman (1992), *The Organic Chemistry of Drug Design and Drug Action*, Academic Press, Inc., San Diego, pages 352-401, Saulnier et al., (1994), *Bioorganic and Medicinal Chemistry Letters*, Vol. 4, p. 1985; Rooseboom et al., *Pharmacological Reviews*, 56:53-102, 2004; Miller et al., *J. Med. Chem*. Vol. 46, no. 24, 5097-5116, 2003; Aesop Cho, "Recent Advances in Oral Prodrug Discovery", *Annual Reports in Medicinal Chemistry*, Vol. 41, 395-407, 2006).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein in their entirety.

Sites on the aromatic ring portion of compounds described herein can be susceptible to various metabolic reactions, therefore incorporation of appropriate substituents on the aromatic ring structures, such as, by way of example only, halogens can reduce, minimize or eliminate this metabolic pathway.

The compounds described herein may be labeled isotopically (e.g. with a radioisotope) or by other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^3H$ and $^{14}C$ are incorporated, are useful in drug and/or substrate tissue distribution assays. Further, substitution with isotopes such as deuterium, i.e., $^2H$, can afford certain therapeutic advantages resulting from greater metabolic stability, for example increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, nitric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion. In some cases, compounds described herein may form coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen by one skilled in the field to provide stable moieties and compounds.

Synthesis of Compounds

The synthesis of compounds described herein may be accomplished using means described in the chemical literature, using the methods described herein, or by a combination thereof. In addition, solvents, temperatures and other reaction conditions presented herein may vary according to those of skill in the art.

The starting materials and reagents used for the synthesis of the compounds described herein may be synthesized or can be obtained from commercial sources, such as, but not limited to, Aldrich Chemical Co. (Milwaukee, Wis.), Sigma Chemical Co. (St. Louis, Mo.), or Bachem (Torrance, Calif.).

The compounds described herein, and other related compounds having different substituents can be synthesized using techniques and materials described herein as well as those that are known to those of skill in the art, such as described, for example, in Fieser and Fieser's Reagents for Organic Synthesis, Volumes 1-17 (John Wiley and Sons, 1991);

Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

Indole compounds described herein may be synthesized starting from indole compounds that are available from commercial sources or they can be prepared using procedures known in the art or outlined herein.

Using the reaction conditions described herein, 1,3-substituted-1H-indole-5-carboxylic acid hydroxyamides and 1,3-substituted-1H-indole-6-carboxylic acid hydroxyamides as disclosed herein are obtained in good yields and purity. The compounds prepared by the methods disclosed herein are purified by conventional means known in the art, such as, for example, filtration, recrystallization, chromatography, distillation, and combinations thereof.

Schemes presented herein are merely illustrative of some methods by which the compounds described herein can be synthesized, and various modifications to these schemes can be made and will be suggested to one skilled in the art having referred to this disclosure.

Formation of Covalent Linkages by Reaction of an Electrophile with a Nucleophile The compounds described herein can be modified using various electrophiles and/or nucleophiles to form new functional groups or substituents. Table 3 entitled "Examples of Covalent Linkages and Precursors Thereof" lists selected non-limiting examples of covalent linkages and precursor functional groups which yield the covalent linkages. Table 3 may be used as guidance toward the variety of electrophiles and nucleophiles combinations available that provide covalent linkages. Precursor functional groups are shown as electrophilic groups and nucleophilic groups.

TABLE 3

Examples of Covalent Linkages and Precursors Thereof

| Covalent Linkage Product | Electrophile | Nucleophile |
| --- | --- | --- |
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |

TABLE 3-continued

Examples of Covalent Linkages and Precursors Thereof

| Covalent Linkage Product | Electrophile | Nucleophile |
| --- | --- | --- |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd⁰-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

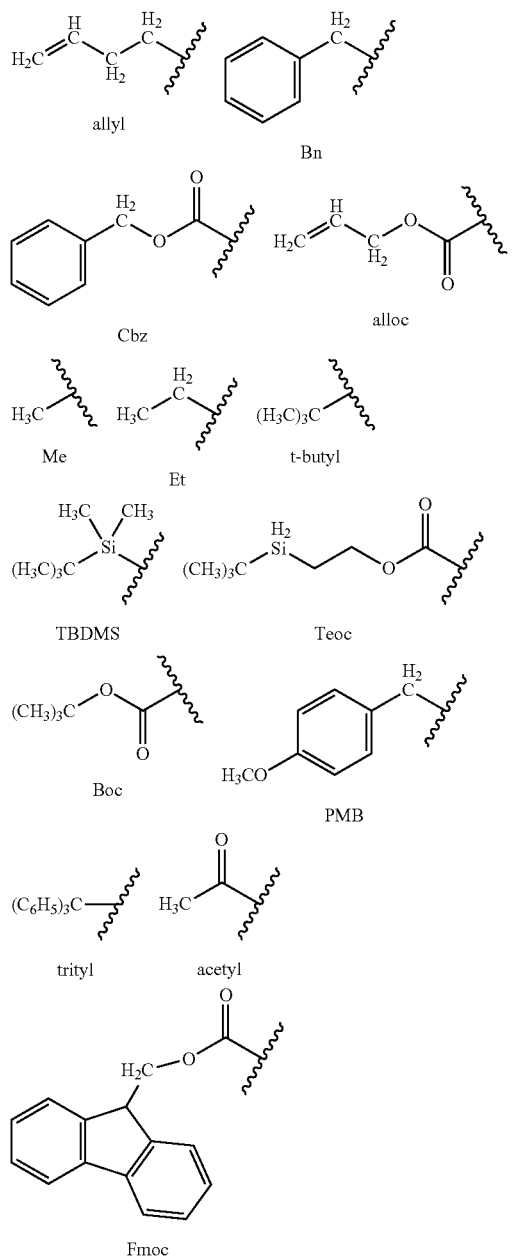

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference in their entirety.

General Synthesis

Indole compounds described herein may be prepared from commercially available materials or they may be prepared by methods known in the art.

In one embodiment, compounds of structure 1 and structure 2 are used as starting materials for the synthesis of compounds described herein.

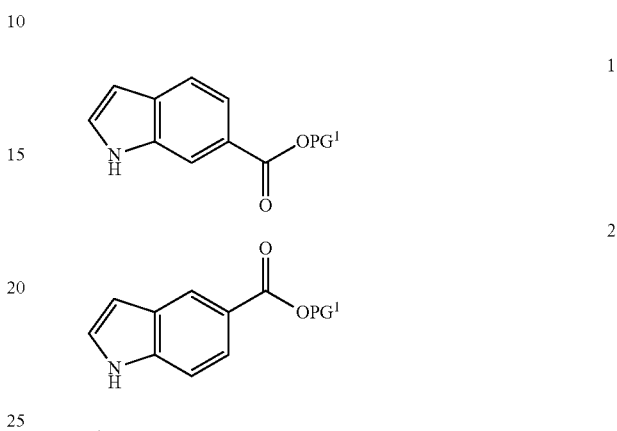

PG¹ represents carboxylic acid protecting groups. In one embodiment, PG¹ represents a substituted or unsubstituted alkyl group, such as, but not limited to, methyl, ethyl, propyl, benzyl, and p-methoxybenzyl.

Indoles of general structure 1 and structure 2 may also be prepared by methods known in the art. Indole containing compounds described herein can be prepared using standard literature procedures such as those found in Katritzky, "Handbook of Heterocyclic Chemistry" Pergamon Press, Oxford, 1986; Pindur et al, *J. Heterocyclic Chem.*, vol 25, 1, 1987, and Robinson "The Fisher Indole Synthesis", John Wiley & Sons, Chichester, N.Y., 1982, each of which is herein incorporated by reference in their entirety.

Additional non-limiting examples of synthetic strategies toward the synthesis of indole compounds described herein, include modifications to various syntheses of indoles, including, but not limited to: Batcho-Leimgruber Indole Synthesis, Reissert Indole Synthesis, Hegedus Indole Synthesis, Fukuyama Indole Synthesis, Sugasawa Indole Synthesis, Bischler Indole Synthesis, Gassman Indole Synthesis, Fischer Indole Synthesis, Japp-Klingemann Indole Synthesis, Buchwald Indole Synthesis, Larock Indole Synthesis, Bartoli Indole Synthesis, Castro Indole Synthesis, Hemetsberger Indole Synthesis, Mori-Ban Indole Synthesis, Madelung Indole Synthesis, Nenitzescu Indole Synthesis, and other unnamed reactions.

In one embodiment, the functionalization of the 1-position and/or 3-position of indoles of structure 1 and structure 2 may be acheived by using any of the indole forming reactions mentioned above with appropriate starting materials.

In another embodiment, the 1-position of indoles described herein may be functionalized as outlined in Scheme 1.

Scheme 1.

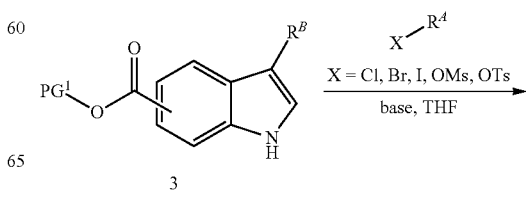

-continued

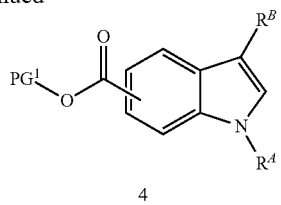

4

Indoles of general structure 4 (where $R^B$ is H, $R^3$, or $-X^5-R$; $R^A$ is $R^4$ or $-X^2-R^2$) are obtained from the N-alkylation of indoles of structure 3 with, for example, an alkyl halide (or benzyl halide, or tosylate (OTs) or mesylate (OMs), or carboxylic acid halide) in a solvent such as tetrahydrofuran (THF) or dimethylformamide (DMF) in the presence of a base, such as, for example, NaH or potassium carbonate or sodium carbonate. In other embodiments, N-arylation of indoles can be acheived using a metal mediated cross coupling of N—H indoles of general structure 3 with aryl halides or triflates ($R^A$ is aryl, heteroaryl; Old et al. *Org. Lett.*, 2 (10), 1403-1406, 2000.).

In addition, when $R^B$ is a bromo or iodine, standard cross coupling reactions allow the introduction of a variety of functional groups using procedures well known to those skilled in the art of organic synthesis. Indoles of structure 3, where $R^B$ is a halide can be prepared using standard bromination conditions or iodination conditions. Metal mediated coupling reactions include, but are not limited to Suzuki reactions, Sonogashira couplings, Heck reactions, Stille cross couplings, Negishi couplings, Kumada couplings, Ullmann reactions, Buchwald-Hartwig reactions, and variants thereof (Metal-Catalyzed Cross-Coupling Reactions, Armin de Meijere (Editor), Francois Diederich (Editor), John Wiley & Sons; 2nd edition, 2004).

Other non-limiting approaches to the functionalization of indoles at the 1-position and/or 3-position are shown in scheme 2.

Scheme 2.

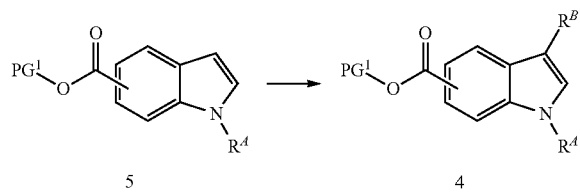

-continued

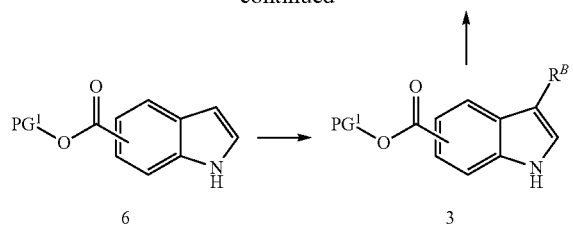

Functionalization at the 3-position of 3-H-indoles of structure 5 ($R^A$ is $R^4$ or $-X^2-R^2$) can be achieved using a variety of reactions and procedures to allow the introduction of a wide range of substituents. By way of example only, acylation using an acid chloride (or anhydride) in the presence of a Lewis acid such as $AlCl_3$, allows for the introduction of acyl groups at the 3-position of indoles (Murakami et al. *Heterocycles*, v14, 1939-1941, 1980 and references cited therein.). Selective reduction of the carbonyl at the 3-position of the indole provides compounds of structure 4 (where $R^B$ is $R^3$, or $-X^5-R^5$, which is a substituted or unsubstituted alkyl; $R^A$ is $R^4$ or $-X^2-R^2$).

The reaction of electron deficient olefins with 3-H indoles of structure 5 ($R^A$ is $R^4$ or $-X^2-R^2$) or structure 6 in the presence of a Lewis acid (such as, for example, Yb $(OTf)_3.3H_2O$) allows the installation of alkyl substituents at the 3-position of the indole compounds to provide indoles of the general structure 4 or 3 (where $R^B$ is $R^3$, or $-X^5-R^5$, which is a substituted alkyl group; see Harrington and Kerr, *Synlett*, 1047-1048, 1996). Alternatively, indoles of structure 6 can be reacted with benzyl derivatives in warm DMF to yield indoles of structure 3 where $R^B$ is $R^3$, or $-X^5-R^5$, which is a substituted benzyl group (Jacobs et al, *J. Med. Chem.*, v36, 394-409, 1993).

In other embodiments, indoles of general structure 5 or 6 can be reacted with methyl ketones in the presence of a base and copper catalyst in order to provide indoles of general structure 3 or 4, where $R^B$ is a substituted alkyl.

In other embodiments, compounds of general structure 5 can be reacted with alkyl halides in the presence of a lewis acid, such as, silver oxide, to provide compounds of general structure 4.

As shown in Scheme 3, 3-formyl indoles of general structure 7 can be condensed with a variety of amines in the presence of a hydride source to provide substituted 3-aminoalkyls of general structure 8.

Scheme 3.

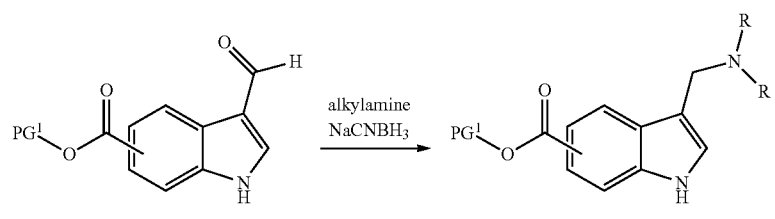

1. $NaBH_4$
2. Alkyl halide, base

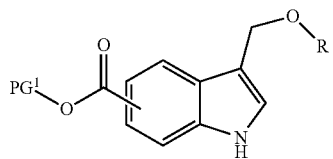

9

In other embodiments, 3-formyl indoles of general structure 7 can be reduced to the alcohol by treatment with a mild hydride source, such as, but not limited to, sodium borohydride. The alcohol can be coupled with a variety of electrophiles, such as, but not limited to, alkyl halides, carboxylic acid halides, to provide compounds of structure 9. 3-Formyl indoles of structure 7 may be prepared using the Vilsmeir reaction or are commercially available.

Conversion of the indoles of general structure 4 (where $R^B$ is $R^3$ or $-X^5-R^5$; $R^A$ is $R^4$ or $-X^2-R^2$) to the corresponding 1,3-substituted-1H-indole-5-carboxylic acid hydroxyamides or 1,3-substituted-1H-indole-6-carboxylic acid hydroxyamides is shown in Scheme 4.

Scheme 4.

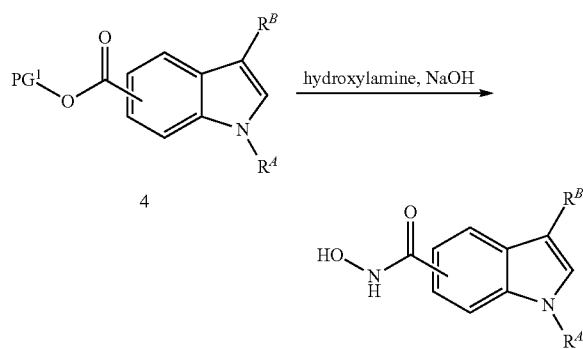

Indoles of structure 4 are treated with sodium hydroxide and an aqueous solution of hydroxylamine to provide the corresponding 1,3-substituted-1H-indole-5-carboxylic acid hydroxyamides or 1,3-substituted-1H-indole-6-carboxylic acid hydroxyamides. In embodiments where $PG^1$ is H in structure 4, the carboxylic acid can be reacted with hydroxylamine hydrochloride salt using a coupling agent such as, but not limited to, 2-(7-Aza-1H-benzotriazole-1-yl)-1,1,3,3-tetramethyluronium hexafluorophosphate (HATU), dicyclohexyl carbodiimide (DCC), and the like, in the presence of a base such as, but not limited to, N,N-diisopropylethylamine, triethylamine, and the like, in a solvent such as, but not limited to, DMF, THF, and the like. In another embodiment, where $PG^1$ is H in structure 4, the carboxylic acid can be reacted with thionyl chloride or oxalyl chloride to provide the acid chloride, which is treated with hydroxylamine to furnish the indole hydroxamic acid compounds.

In one embodiment, indole-6-hydroxamic acids described herein may be synthesized by a process that includes:

(a) reacting an intermediate of Formula 1:

Formula 1

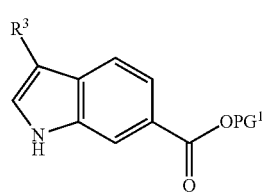

where $PG^1$ is a carboxy-protecting group, such as, but not limited to, methyl, ethyl, propyl, benzyl, p-methoxybenzyl, and the like;

with a compound having a formula $R^2-X^2-Y$, where Y is a halide, to yield an intermediate of Formula 6:

Formula 6

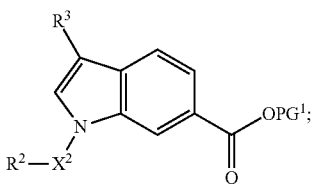

(b) optionally reducing the intermediate of Formula 6 where $R^2$ is phenyl substituted with nitro to yield an intermediate of formula 10:

Formula 10

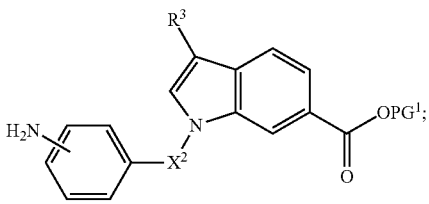

(c) optionally reacting the intermediate of Formula 6 where $R^5$ is phenyl substituted with amino or alkylamino or reacting the intermediate of Formula 10 with ROH where R is acyl or alkylsulfonyl, as defined herein, to yield an intermediate of Formula 11:

Formula 11

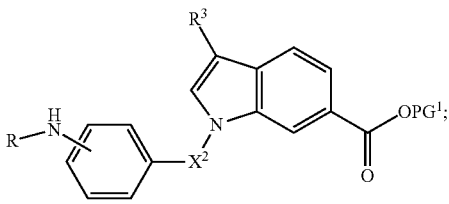

(d) optionally reacting the intermediate of Formula 6 where $R^5$ is phenyl substituted with carboxy with $NH_2$(alkyl) or NH(alkyl)$_2$ to yield an intermediate of Formula 12:

Formula 12

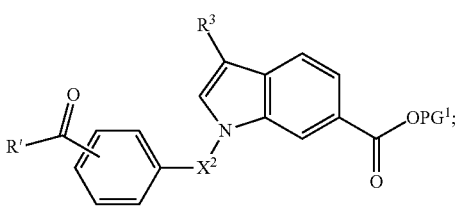

where R' is alkylamino or dialkylamino;

(e) deprotecting the intermediate of Formula 6, the intermediate of Formula 10, the intermediate of Formula 11, and the intermediate of Formula 12 to yield a corresponding carboxylic acid;

(c) reacting the carboxylic acid from Step (e) with hydroxylamine to yield a indole-hydroxamic acid compound described herein; and (e) optionally separating individual isomers.

In another embodiment, provided herein is a method of making indole 5-hydroxamic acids, which includes:

(a) reacting an intermediate of Formula 2:

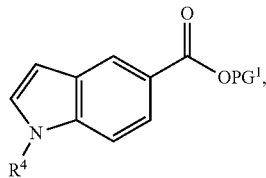

Formula 2 where $PG^1$ is a carboxy-protecting group,
with an intermediate of formula $R^5$—$X^5$—Y where Y is a halide to yield an intermediate of Formula 4:

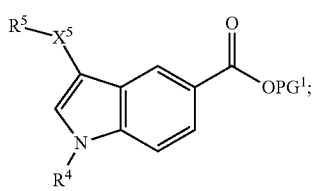

Formula 4

(b) optionally reducing the intermediate of Formula 4 where $R^5$ is phenyl substituted with nitro to yield an intermediate of Formula 7:

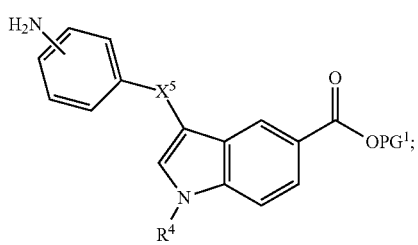

Formula 7

(c) optionally reacting the intermediate of formula 4 where $R^5$ is phenyl substituted with amino or alkylamino or reacting the intermediate of Formula 7 with ROH where R is acyl, as defined herein, to yield an intermediate of Formula 8:

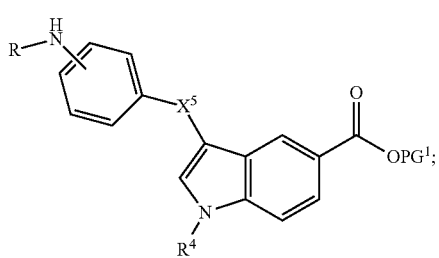

Formula 8

(d) optionally reacting the intermediate of formula 4 where $R^5$ is phenyl substituted with carboxy with $NH_2$(alkyl) or $NH(alkyl)_2$ to yield an intermediate of Formula 9:

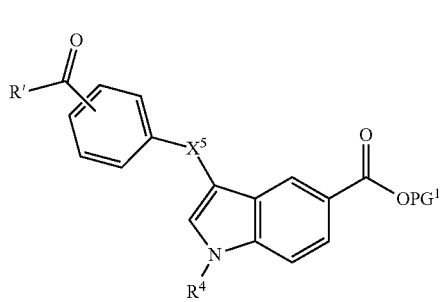

Formula 9 where R' is alkylamino or dialkylamino;

(e) deprotecting the intermediate of formula 4, the intermediate of Formula 7, the intermediate of Formula 8, and the intermediate of Formula 9 to yield a corresponding carboxylic acid;

(f) reacting the carboxylic acid from Step (e) with hydroxylamine to yield a indole 5-hydroxamic acid described herein; and (g) optionally separating individual isomers.

Throughout the specification, groups and substituents thereof can be chosen by one skilled in the field to provide stable moieties and compounds.

CERTAIN TERMINOLOGY

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. In addition, nucleic acid and amino acid sequences for HDAC8 are known in the art as disclosed in, e.g., U.S. Pat. No. 6,875, 598. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substitutents).

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, t-butyl, pentyl, iso-pentyl, neo-pentyl, and hexyl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Alkyl groups can be substituted or unsubstituted. Depending on the structure, an alkyl group can be a monoradical or a diradical (i.e., an alkylene group).

An "alkoxy" group refers to a (alkyl)O— group, where alkyl is as defined herein. Examples of alkoxy groups include, but are not limited to, methoxy, ethoxy, propoxy, isopropoxy, buytloxy, cyclopropyloxy, cyclopentyloxy, cyclohexyloxy, and the like.

"Hydroxyalkyl" refers to an alkyl group substituted with hydroxy group(s).

"Hydroxyalkoxy" refers to an alkoxy substituted with hydroxy group(s).

"Alkoxyalkyl" refers to alkyl group substituted with alkoxy group(s).

"Alkoxyalkyloxy" refers to an alkoxy group as defined herein substituted with alkoxy group as defined herein.

"Alkoxycarbonyl" refers to a —C(=O)O-(alkyl) group, where alkyl as defined herein. Non-limiting examples of alkoxycarbonyl groups include, e.g., methoxycarbonyl, ethoxycarbonyl, and the like.

"Alkoxycarbonylamino" refers to a —NR(C=O)—O-(alkyl), where alkyl is as defined herein and R is H, alkyl, heteroalkyl, haloalkyl, and the like.

The term "alkenyl" refers to a type of alkyl group in which the first two atoms of the alkyl group form a double bond that is not part of an aromatic group. That is, an alkenyl group begins with the atoms —C(R)=$CR_2$, wherein R refers to the remaining portions of the alkenyl group, which may be the same or different. Non-limiting examples of an alkenyl group include —CH=$CH_2$, —C($CH_3$)=$CH_2$, —CH=$CHCH_3$ and —C($CH_3$)=$CHCH_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

"Alkenylcarbonyl" refers to a —C(O)-(alkenyl) group, where alkenyl is as defined herein.

"Alkenylcarbonyloxy" refers to a —OC(O)-(alkenyl) group, where alkenyl is as defined herein.

"Alkenyloxy" refers to a —O-(alkenyl) group, where alkenyl is as defined herein.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡$CCH_3$, —C≡$CCH_2CH_3$ and —C≡$CCH_2CH_2CH_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —$NH_2$ group, or an N-oxide derivative.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

"Aminoalkyl" refers to an alkyl group as is defined herein that is substituted with an amino group.

"Aminoalkoxy" refers to an alkoxy group substituted with an amino group.

"Aminocarbonyl" refers to a —$CONH_2$ group.

"Aminosulfonyl" means an —S(O)$_2$$NH_2$ radical.

The term "alkylaminoalkyl" refers to an alkyl group, as is defined herein, substituted with an alkylamine as is defined herein. "Dialkylaminoalkyl" refers to an alkyl group that is substituted with a dialkylamino group.

"Alkylaminoalkyloxy" refers to a alkoxy substituted with an alkylamine.

"Alkylaminocarbonyl" means a —C(O)R radical where R is alkylamino as defined herein.

"Alkylaminocarbonylamino" refers to —NHC(=O)-(alkylamino).

"Alkylaminocarbonyloxy" refers to —OC(=O)-(alkylamino).

"Alkylaminosulfonyl" refers to —S(=O)$_2$NHR radical where R is alkyl, as defined herein.

"Alkylcarbonyl" means a —C(=O)R radical where R is alkyl as defined herein.

"Alkylcarbonylamino" means a —NR'C(=O)-(alkyl), where R' is hydrogen, alkyl, haloalkyl, heteroalkyl.

"Alkylcarbonyloxy" means a —OC(=O)R radical where R is alkyl as defined herein.

"Dialkylaminoalkyloxy" refers to a alkoxy substituted with a dialkylamino.

"Dialkylaminocarbonyl" refers to —C(=O)R, where R is dialkylamino.

"Dialkylaminocarbonylamino" refers to —NR'—C(=O)-(dialkylamino), where R' is hydrogen, alkyl, heteroalkyl, haloalkyl, and dialkylaminocarbonyl as defined herein.

"Dialkylaminocarbonyloxy" means an —O(C=O)-(dialkylamino), dialkylaminocarbonyl as defined herein.

"Dialkylaminosulfonyl" refers to —S(O)$_2$NR$_2$, where R is alkyl as defined herein.

An "amide" is a chemical moiety with formula —C(O)NHR or —NHC(O)R, where R is selected from the group consisting of alkyl, cycloalkyl, aryl, heteroaryl (bonded through a ring carbon) and heteroalicyclic (bonded through a ring carbon). An amide may be an amino acid or a peptide molecule attached to a compound of Formula (A), thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "ester" refers to a chemical moiety with formula —C(=O)OR, where R is selected from the group consisting of alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, phenyl, pyridine, piperidine, morpholine, piperazine, pyridazine, pyrimidine, pyrazine, pyran and thiopyran are 6-membered rings; and cyclopentyl, pyrrolidine, imidazole, oxazole, thiazole, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e a heteroatom). Heterocycle includes heteroaryl and heterocycloalkyl. Carbocycles and heterocycles can be optionally substituted.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Aralkyl" or "arylalkyl" refers to an alkyl group as is defined herein substituted with an aryl group as is defined herein.

"Phenylalkyl" refers to an alkyl substituted with a phenyl.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring. Cycloalkyl groups include groups having from 3 to 10 ring atoms. Illustrative examples of cycloalkyl groups include, but are not limited to, the following moities:

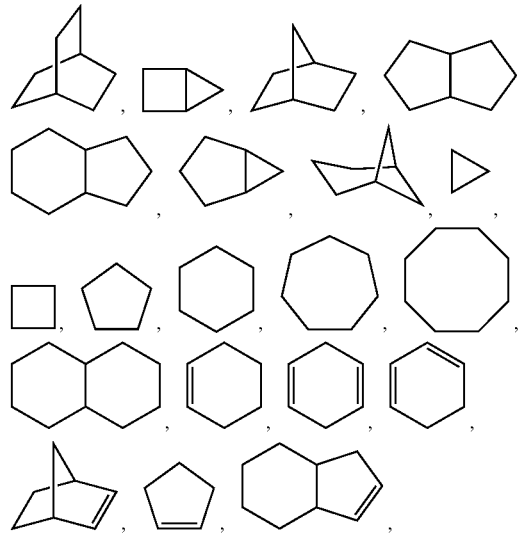

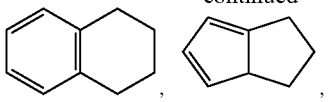

and the like. Monocyclic cycloalkyls include, but are not limited to, cyclopropyl, cyclobutyl, cyclopentyl, cyclohexyl, cycloheptyl, and cyclooctyl.

"Cycloalkylalkyl" refers to an alkyl, as is defined herein, substituted with a cycloalkyl, as is defined herein.

"Cycloalkylcarbonyl" refers to —C(=O)-cycloalkyl.

The term "heterocycle" refers to heteroaromatic and heteroalicyclic groups containing one to four ring heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For example, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Polycyclic heteroaryl groups may be fused or non-fused. Illustrative examples of heteroaryl groups include the following moieties:

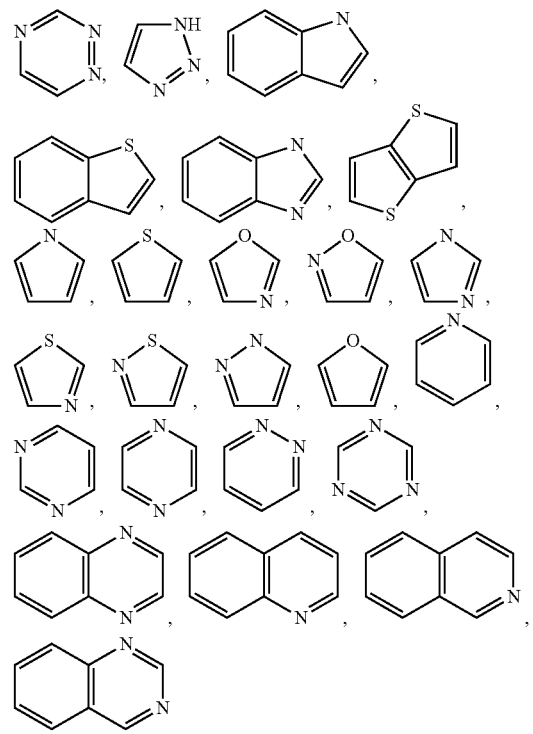

and the like.

In some embodiments, substituted or unsubstituted heteroaryl groups may be selected from among pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, 4-azaindolyl, 5-azaindolyl, 6-azaindolyl, 7-azaindolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothienyl, benzothiazolyl, benzoxazolyl, quinazolinyl, quinoxalinyl, imidazo[1,2-a]pyridinyl, thiophenopyridinyl, and furopyridinyl. In other embodiments, substituted or unsubstituted heteroaryl groups may be selected from among pyridinyl, pyrimidinyl, pyrazinyl, quinolinyl, isoquinolinyl, indolyl, benzimidazolyl, benzofuranyl, cinnolinyl, indazolyl, indolizinyl, phthalazinyl, pyridazinyl, isoindolyl, pteridinyl, purinyl, oxadiazolyl, thiadiazolyl, furazanyl, benzofurazanyl, benzothienyl, benzothiazolyl, benzoxazolyl, quinazolinyl, quinoxalinyl, naphthyridinyl, imidazo[1,2-a]pyridinyl, thiophenopyridinyl, and furopyridinyl. In yet other embodiments, substituted or unsubstituted heteroaryl groups may be selected from among pyridinyl, pyrimidinyl, pyrazinyl, quinolinyl, isoquinolinyl, pyridazinyl, quinazolinyl, quinoxalinyl. In still other embodiments, substituted or unsubstituted heteroaryl groups may be selected from among pyridinyl, and quinolinyl.

"Heteroaralkyl" or "heteroarylalkyl" refers to an alkyl, as is defined herein, substituted with a heteroaryl as is defined herein.

A "heteroalicyclic" group or "heterocycloalkyl" group refers to a cycloalkyl group, wherein at least one skeletal ring atom is a heteroatom selected from nitrogen, oxygen and sulfur.

The radicals may be fused with an aryl or heteroaryl. Illustrative examples of heterocycloalkyl groups, also referred to as non-aromatic heterocycles, include:

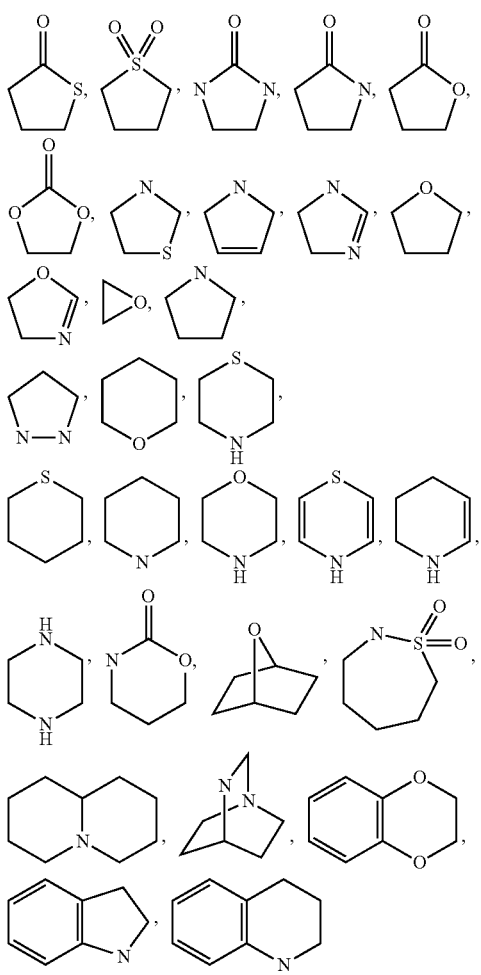

and the like. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e skeletal atoms of the heterocycloalkyl ring).

In some embodiments, substituted or unsubstituted heterocycloalkyl groups may be selected from among quinolizinyl, dioxinyl, piperidinyl, morpholinyl, thiomorpholinyl, thiazinyl, tetrahydropyridinyl, piperazinyl, oxazinanonyl, dihydropyrrolyl, dihydroimidazolyl, tetrahydrofuranyl, tetrahydropyranyl, dihydrooxazolyl, oxiranyl, pyrrolidinyl, pyrazolidinyl, dihydrothienyl, imidazolidinonyl, pyrrolidinonyl, dihydrofuranonyl, dioxolanonyl, thiazolidinyl, piperidinonyl, indolinyl, indanyl, tetrahydronaphthalenyl, tetrahydroquinolinyl, tetrahydroisoquinolinyl, and tetrahydrothienyl. In other embodiments, substituted or unsubstituted heterocycloalkyl groups may be selected from among piperidinyl, morpholinyl, piperazinyl, dihydropyrrolyl, dihydroimidazolyl, tetrahydrofuranyl, dihydrooxazolyl, pyrrolidinyl, pyrazolidinyl, dihydrothienyl, imidazolidinonyl, pyrrolidinonyl, piperidinonyl, indolinyl, indanyl, tetrahydronaphthalenyl, tetrahydroquinolinyl, tetrahydroisoquinolinyl, and tetrahydrothienyl. In yet other embodiments, substituted or unsubstituted heterocycloalkyl groups may be selected from among piperidinyl, morpholinyl, piperazinyl, tetrahydrofuranyl, pyrrolidinyl, pyrrolidinonyl, piperidinonyl, indolinyl, indanyl, tetrahydronaphthalenyl, tetrahydroquinolinyl, and tetrahydrothienyl.

"Heterocycloalkylalkyl" refers to an alkyl, as defined herein, substituted with a heterocycloalkyl, as defined herein.

As used herein, "1,3-substituted-1H-indole-6-carboxylic acid hydroxyamide" or "1,3-substituted-1H-indole-6-hydroxamic acid" refers to:

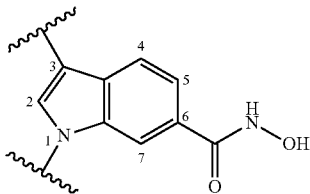 [SMILES: *c1cn(*)c2cc(C(=O)NO)ccc12]

As used herein, "1,3-substituted-1H-indole-5-carboxylic acid hydroxyamide" or "1,3-substituted-1H-indole-5-hydroxamic acid" refers to:

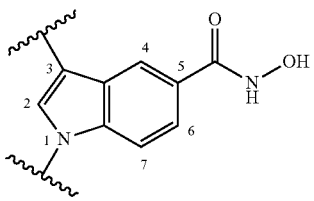 [SMILES: *c1cn(*)c2ccc(C(=O)NO)cc12]

The term "hydroxamate", "hydroxamic acid", "N-hydroxycarboxamide" or "carboxylic acid hydroxyamide" refers to:

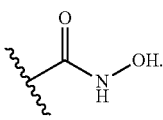

The term "halo" or, alternatively, "halogen" means fluoro, chloro, bromo and iodo.

The terms "haloalkyl," "haloalkenyl," "haloalkynyl" and "haloalkoxy" include alkyl, alkenyl, alkynyl and alkoxy structures that are substituted with one or more halogens. The halogens may the same or they may be different. The terms "fluoroalkyl" and "fluoroalkoxy" include haloalkyl and haloalkoxy groups, respectively, in which the halo is fluorine. Non-limiting examples of haloalkyls include —$CH_2Cl$, —$CF_3$, —$CHF_2$, —$CH_2CF_3$, —$CF_2CF_3$, —$CF(CH_3)_3$, and the like. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of haloalkoxy groups include —$OCF_3$, —$OCHF_2$, —$OCH_2F$, —$OCH_2CF_3$, —$OCF_2CF_3$, —$OCF_2CF_2CF_3$, —$OCF(CH_3)_3$, and the like.

The terms "heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$. Excluding the number of heteroatoms, a "heteroalkyl" may have from 1 to 6 carbon atoms, a "heteroalkenyl" may have from 2 to 6 carbons atoms, and a "heteroalkynyl" may have from 2 to 6 carbon atoms. Examples of heteroalkyls include but are not limited to, CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH$_2$—CH═N—OCH$_3$, —CH$_2$—NH—OCH$_3$ and —CH$_2$—O—Si(CH$_3$)$_3$.

The term "bond" or "single bond" refers to a chemical bond between two atoms, or two moieties when the atoms joined by the bond are considered to be part of larger substructure.

The term "moiety" refers to a specific segment or functional group of a molecule.

Chemical moieties are often recognized chemical entities embedded in or appended to a molecule.

A "cyano" group refers to a —CN group.

"Cyanoalkyl" refers to an alkyl, as is defined herein, substituted with a cyano.

"Cyanoalkylaminocarbonyl" refers to a —C(═O)NR'(cyanoalkyl) group, where R' is hydrogen, alkyl, heteroalkyl, haloalkyl, as is defined herein, cyanoalkyl is as defined herein.

An "isocyanato" group refers to a —NCO group.

A "thiocyanato" group refers to a —CNS group.

An "isothiocyanato" group refers to a —NCS group.

"Mercaptyl" or "sulfanyl" refers to a —S— moiety.

"Alkylthio" means an —SR radical where R is alkyl as defined herein.

"Acyloxy" refers to a RC(═O)O— group.

"Acyl" refers to a RC(═O)— group.

"Acylamino" refers to a RC(═O)N(R')-group, where R' is hydrogen, hydroxy, alkyl, or alkoxy. In some embodiments, R' is H or R.

"Acyloxy" refers to RC(═O)O— group.

"Sulfinyl" refers to a —S(═O)— moiety.

"Alkylsulfinyl" means an —S(O)R radical where R is alkyl as defined herein.

"Sulfonyl" refers to a —S(═O)$_2$— moiety.

"Alkylsulfonyl" means a —SO$_2$R radical where R is alkyl as defined herein.

"Alkylsulfonylamino" means a —N(R')SO$_2$R group, where R' is hydrogen, alkyl, heteroalkyl, haloalkyl, as is defined herein, and R is alkyl as is defined herein.

"Phenylsulfonyl" refers to means a —S(═O)$_2$-phenyl moiety.

"Phenylsulfonylamino" refers to a —NR'SO$_2$-(phenyl) group, where R' is hydrogen, alkyl, heteroalkyl, haloalkyl, as is defined herein.

"Heteroarylaminocarbonyl" refers to a —C(═O)NR'(heteroaryl) group, where R' is hydrogen, alkyl, heteroalkyl, haloalkyl, as is defined herein, and heteroaryl is as defined herein.

"Arylaminocarbonyl" refers to a —C(═O)NR' (aryl) group, where R' is hydrogen, alkyl, heteroalkyl, haloalkyl, as is defined herein, and aryl is as defined herein.

"Arylcarbonylamino" refers to —NR'C(═O)-(aryl) group, where R' is hydrogen, alkyl, heteroalkyl, haloalkyl, as is defined herein, and aryl is as defined herein.

"Carboxy" refers to a —C(═O)OH group.

As used herein, the substituent "R" appearing by itself and without a number designation refers to a substituent selected from among from alkyl, haloalkyl, heteroalkyl, alkenyl, cycloalkyl, cycloalkylalkyl, aryl, arylalkyl, heteroaryl (bonded through a ring carbon), heteroarylalkyl, heterocycloalkyl, and heterocycloalkylalkyl.

The term "optionally substituted" or "substituted" means that the referenced group may be substituted with one or more additional group(s) individually and independently selected from alkyl, cycloalkyl, aryl, heteroaryl, heterocycloalkyl, hydroxy, alkoxy, aryloxy, alkylthio, arylthio, alkylsulfoxide, arylsulfoxide, alkylsulfone, arylsulfone, cyano, halo, acyl, acyloxy, isocyanato, thiocyanato, isothiocyanato, nitro, haloalkyl, fluoroalkyl, and amino, including mono- and di-substituted amino groups (e.g. —NH$_2$, —NHR, —N(R)$_2$), and the protected derivatives thereof. By way of example, an optional substituents may be $L^S R^S$, wherein each $L^S$ is independently selected from a bond, —O—, —C(═O)—, —S—, —S(═O)—, —S(═O)$_2$—, —NH—, —NHC(O)—, —C(O)NH—, S(═O)$_2$NH—, —NHS(═O)$_2$, —OC(O)NH—, —NHC(O)O—, —(C$_1$-C$_6$alkyl)-, or —(C$_2$-C$_6$alkenyl)-; and each $R^S$ is independently selected from among H, (C$_1$-C$_6$alkyl), (C$_3$-C$_8$cycloalkyl), aryl, heteroaryl, heteocycloalkyl, and C$_1$-C$_6$heteroalkyl. The protecting groups that may form the protective derivatives of the above substituents are known to those of skill in the art and may be found in references such as Greene and Wuts, above.

The compounds presented herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

The methods and formulations described herein include the use of N-oxides, crystalline forms (also known as polymorphs), or pharmaceutically acceptable salts of compounds having the structure of Formula (A), as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

The terms "kit" and "article of manufacture" are used as synonyms.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

A "selective HDAC8 inhibitor," as used herein, refers to a compound that has an $IC_{50}$ for inhibition of HDAC8 deacetylase activity that is at least 5 fold to more than 500 fold lower than the $IC_{50}$ for inhibition of deacetylase activity of another HDAC. In some embodiments, the selective HDAC8 inhibitor has an $IC_{50}$ for inhibition of HDAC8 deacetylase activity that is about 5, 10, 50, 100, 150, 200, 250, 300, 350, 400, 450 or more than 500 fold lower than the $IC_{50}$ for inhibition of deacetylase activity of another HDAC. In one embodiment, the selective HDAC8 inhibitor has an $IC_{50}$ for inhibition of HDAC8 deacetylase activity that is at least 10 fold lower than the $IC_{50}$ for inhibition of deacetylase activity of at least one of HDAC1, HDAC2, HDAC3, HDAC6, HDAC10, and HDAC11; in another embodiment at least two of HDAC1, HDAC2, HDAC3, HDAC6, HDAC10, and HDAC11; in another embodiment all of HDAC1, HDAC2, HDAC3, HDAC6, HDAC10, and HDAC11. In another embodiment, the selective HDAC8 inhibitor has an $IC_{50}$ for HDAC8 deacetylase activity that is at least 20 fold lower than the $IC_{50}$ for inhibition of deacetylase activity of at least one of HDAC1, HDAC2, HDAC3, HDAC6, HDAC10, and HDAC11; in another embodiment at least two of HDAC1, HDAC2, HDAC3, HDAC6, HDAC10, and HDAC11; in another embodiment all of HDAC1, HDAC2, HDAC3, HDAC6, HDAC10, and HDAC11.

As used herein, the term "target protein" refers to a protein or a portion of a protein capable of being bound by a selective binding compound. In certain embodiments, a target protein is HDAC8.

As used herein, the term "selective binding compound" refers to a compound that selectively binds to any portion of one or more target proteins.

As used herein, the term "selectively binds" refers to the ability of a selective binding compound to bind to a target protein, such as, for example, HDAC8, with greater affinity than it binds to a non-target protein. In certain embodiments, specific binding refers to binding to a target with an affinity that is at least 10, 50, 100, 250, 500, 1000 or more times greater than the affinity for a non-target.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a target. For example, a modulator can cause an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target. In certain embodiments, a modulator is an activator, which increases the magnitude of at least one activity of a target. In certain embodiments the presence of a modulator results in an activity that does not occur in the absence of the modulator.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "inhibits", "inhibiting", or "inhibitor" of HDAC, as used herein, refer to inhibition of histone deacetylase activity.

The term "acceptable" with respect to a formulation, composition or ingredient, as used herein, means having no persistent detrimental effect on the general health of the subject being treated.

By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutical combination" as used herein, means a product that results from the mixing or combining of more than one active ingredient and includes both fixed and non-fixed combinations of the active ingredients. The term "fixed combination" means that the active ingredients, e.g. an idole compound described herein, and a co-agent, are both administered to a patient simultaneously in the form of a single entity or dosage. The term "non-fixed combination" means that the active ingredients, e.g. an indole compound described herein, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of an indole compound described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising an indole compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "co-administration" or the like, as used herein, are meant to encompass administration of the selected therapeutic agents to a single patient, and are intended to include treatment regimens in which the agents are administered by the same or different route of administration or at the same or different time.

The term "carrier," as used herein, refers to relatively non-toxic chemical compounds or agents that facilitate the incorporation of a compound into cells or tissues.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The term "enzymatically cleavable linker," as used herein refers to unstable or degradable linkages which may be degraded by one or more enzymes.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

Examples of Pharmaceutical Compositions and Methods of Administration

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

Provided herein are pharmaceutical compositions that include an indole compound described herein, and a pharmaceutically acceptable diluent(s), excipient(s), or carrier(s). In addition, the compounds described herein can be administered as pharmaceutical compositions in which compounds described herein are mixed with other active ingredients, as in combination therapy. In some embodiments, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

A pharmaceutical composition, as used herein, refers to a mixture of an indole compound described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Alternately, one may administer the compounds and/or compositions in a local rather than systemic manner, for example, via injection of the compound directly into an organ, often in a depot preparation or sustained release formulation. Such long acting formulations may be administered by implantation (for example subcutaneously or intramuscularly) or by intramuscular injection. Furthermore, one may administer the drug in a targeted drug delivery system, for example, in a liposome coated with organ-specific antibody. The liposomes will be targeted to and taken up selectively by the organ. In addition, the drug may be provided in the form of a rapid release formulation, in the form of an extended release formulation, or in the form of an intermediate release formulation.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one indole compound described herein, as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

"Bioavailability" refers to the percentage of the weight of indole compounds disclosed herein, that is delivered into the general circulation of the animal or human being studied. The total exposure (AUC(0-∞)) of a drug when administered intravenously is usually defined as 100% bioavailable (F %). "Oral bioavailability" refers to the extent to which indole compounds disclosed herein, are absorbed into the general circulation when the pharmaceutical composition is taken orally as compared to intravenous injection.

"Blood plasma concentration" refers to the concentration of indole compounds disclosed herein, in the plasma component of blood of a subject. It is understood that the plasma concentration of indole compounds described herein may vary significantly between subjects, due to variability with respect to metabolism and/or possible interactions with other therapeutic agents. In accordance with one embodiment disclosed herein, the blood plasma concentration of the indole compounds disclosed herein may vary from subject to subject. Likewise, values such as maximum plasma concentration (Cmax) or time to reach maximum plasma concentration (Tmax), or total area under the plasma concentration time curve (AUC(0-∞)) may vary from subject to subject. Due to this variability, the amount necessary to constitute "a therapeutically effective amount" of a compound may vary from subject to subject.

"Carrier materials" include any commonly used excipients in pharmaceutics and should be selected on the basis of compatibility with compounds disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticiczers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art.

Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, µg, or ng of therapeutic agent per ml, dl, or l of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

The compositions described herein can be formulated for administration to a subject via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include an indole compound described herein, can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of an indole compound described herein, with one or more pharmaceutical excipients to form a bulk blend composition. When referring to these bulk blend compositions as homogeneous, it is meant that the particles of the indole compound described herein, are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., "The Theory and Practice of Industrial Pharmacy" (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include an indole compound described herein, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the indole compound described herein from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms of the pharmaceutical compositions described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the indole compound described herein from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the indole compound described herein and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with indole compounds described herein, which sufficiently isolate the compound from other non-compatible excipients. Materials compatible with indole compounds described herein are those that delay the release of the indole compounds in vivo.

Exemplary microencapsulation materials useful for delaying the release of the formulations including indole compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated indole compounds described herein may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of indole compounds described herein are microencapsulated prior to being formulated into one of the above forms. In still another embodiment, some or most of the particles are coated prior to being further formulated by using standard coating procedures, such as those described in Remington's Pharmaceutical Sciences, 20th Edition (2000).

In other embodiments, the solid dosage formulations of the indole compounds described herein are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with an indole compound described herein may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include an indole compound described herein, are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518.

The pharmaceutical solid oral dosage forms including formulations described herein, which include an indole compound described herein, can be further formulated to provide a controlled release of the indole compound. Controlled release refers to the release of the indole compound described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating for the methods and compositions described herein to achieve delivery to the lower gastrointestinal tract. In some embodiments such polymers are anionic carboxylic polymers. In other embodiments, the polymers and compatible mixtures thereof, and some of their properties, include, but are not limited to:

Shellac, also called purified lac. This coating dissolves in media of pH >7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH >6. Aquateric (FMC) is an aqueous based system and is a spray dried CAP psuedolatex with particles <1 µm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP). PVAP dissolves in pH >5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include an indole compound described herein, are delivered using a pulsatile dosage form. A pulsatile dosage form is capable of providing one or more immediate release pulses at predetermined time points after a controlled lag time or at specific sites. Pulsatile dosage forms including the formulations described herein, may be administered using a variety of pulsatile formulations known in the art. For example, such formulations include, but are not limited to, those described in U.S. Pat. Nos. 5,011,692, 5,017,381, 5,229,135, and 5,840,329. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284. In one embodiment, the controlled release dosage form is pulsatile release solid oral dosage form including at least two groups of particles, (i.e. multiparticulate) each containing the formulation described herein. The first group of particles provides a substantially immediate dose of the indole compound described herein upon ingestion by a mammal. The first group of particles can be either uncoated or include a coating and/or sealant. The second group of particles includes coated particles, which includes from about 2% to about 75%, preferably from about 2.5% to about 70%, and more preferably from about 40% to about 70%, by weight of the total dose of the indole compound described herein in said formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the formulation that includes an indole compound described herein.

Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., Pharmaceutical Dosage Forms, 2 Ed., Vol. 1, pp. 209-214 (1990); Singh et al., Encyclopedia of Pharmaceutical Technology, 2nd Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983.

In some embodiments, pharmaceutical formulations are provided that include particles of the indole compounds described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the indole compound described herein, the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension® can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion.

In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal formulations are known in the art and are described in, for example, U.S. Pat. Nos. 4,476,116, 5,116, 817 and 6,391,452. Formulations that include an indole compound described herein, which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the indole compounds described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal formulations that include indole compounds described herein may be administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the indole compound is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the indole compound described herein, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiments, the transdermal formulations described herein include at least three components: (1) a formulation of an indole compound described herein; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the indole compounds described herein. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Formulations that include an indole compound described herein, suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Examples of Methods of Dosing and Treatment Regimens

The compounds described herein can be used in the preparation of medicaments for the inhibition of HDAC8, or for the treatment of diseases or conditions that would benefit, at least in part, from inhibition of HDAC8. In addition, a method for treating any of the diseases or conditions described herein in a subject in need of such treatment, involves administration of pharmaceutical compositions containing at least one indole compound described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, preferably 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein described herein are from about 0.01 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration include from about 1 to 50 mg active ingredient. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it can be expressed as the ratio between LD50 and ED50. Compounds exhibiting high therapeutic indices are preferred. The data obtained from cell culture assays and animal studies can be used in formulating a range of dosage for use in human. The dosage of such compounds lies preferably within a range of circulating concentrations that include the ED50 with minimal toxicity. The dosage may vary within this range depending upon the dosage form employed and the route of administration utilized.

Combination Treatments

The compounds and compositions described herein can also be used in combination with other well known therapeutic agents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

In certain instances, it may be appropriate to administer at least one compound described herein in combination with another therapeutic agent. By way of example only, if one of the side effects experienced by a patient upon receiving one of the compounds herein, such as an indole hydroxamic acid compound described herein, is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a HDAC8 selective compound described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, preferably about 1 month to about 5 years, and more preferably from about 1 month to about 3 years.

Anti-Cancer Agents

Combinations of selective HDAC8 inhibitors described herein with other anti-cancer or chemotherapeutic agents are described herein. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved.

HDAC inhibitors in combination with other anti-cancer agents have been explored. HDAC inhibitors have been reported to be additive or synergistic with a number of anti-cancer agents, including, but not limited to anthrocyclins, fludarabine, flavopiridol, imatinib, bortezomib, anti-angiogenesis agents and nuclear receptor ligands, such as, all-trans retinoic acid and tumor necrosis factor-related apoptosis-inducing ligand (Fuino L, et al. (2003). Mol Cancer Ther 2: 971-984; Johnstone R W, Licht J D. (2003). Cancer Cell 4: 13-18; Bhalla K N. (2005). J Clin Oncol 23: 3971-3993; Dokmanovic M, Marks P A. (2005). J Cell Biochem 96: 293-304; Minucci S, Pelicci P G. (2006). Nat Rev Cancer 6: 38-51; Yoo C B, Jones P A. (2006). Nat Rev Drug Discov 5: 37-50).

Anti-cancer agents and/or agents used in chemotherapy include, but are not limited to, the following: estrogen receptor modulators, androgen receptor modulators, retinoid receptor modulators, cytotoxic/cytostatic agents, antiproliferative agents, prenyl-protein transferase inhibitors, nitrogen mustards, nitroso ureas, angiogenesis inhibitors, inhibitors of cell proliferation and survival signaling pathway, apoptosis inducing agents, agents that interfere with cell cycle checkpoints, agents that interfere with receptor tyrosine kinases (RTKs), integrin blockers, NSAIDs, inhibitors of inherent multidrug resistance (MDR), anti-emetic agents, agents useful in the treatment of anemia, agents useful in the treatment of neutropenia, immunologic-enhancing drugs, biphosphonates, aromatase inhibitors, agents inducing terminal differencation of neoplastic cells, γ-secretase inhibitors, cancer vaccines, and any combination thereof.

Where the subject is suffering from a cancer (e.g., a T-cell lymphoma), a selective HDAC8 inhibitor can be used in any combination with one or more other anti-cancer agents. Examples of anti-cancer agents include, but are not limited to, any of the following: 5-aza-2'-deoxycytidine, all trans retinoic acid, doxorubicin, vincristine, etoposide, gemcitabine, imatinib (Gleevec®), 17-N-allylamino-17-demethoxygeldanamycin (17-AAG), flavopiridol, LY294002, bortezomib, trastuzumab, BAY 11-7082, PKC412, or PD184352.

Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Other anti-cancer agents that can be employed in combination with a selective HDAC8 inhibitor include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a selective HDAC8 inhibitor include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A;

placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a selective HDAC8 inhibitor include alkylating agents, antimetabolites, natural products, or hormones, nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a selective HDAC8 inhibitor include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a selective HDAC8 inhibitor include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with a selective HDAC8 inhibitor include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide, SPD-424).

In another embodiment, Dynepo gene activated erythropoietin (Anti-anemic; human erythropoietin) may be administered in combination with selective HDAC8 inhibitor compounds.

"Estrogen receptor modulators" refers to compounds that interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpr-opanoate, 4,4'-dihydroxybenzophenone-2,4-dinitrophenyl-hydrazone, and SH646. In some embodiments, estrogen receptor modulators are tamoxifen and raloxifene.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX$^{23}$-7553, trans-N-(4'-hydroxyphenyl)retinamide, and N-4-carboxyphenyl retinamide.

Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with a selective HDAC8 inhibitor include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX$^{100}$, (trans, trans, trans)-bis-mu-(hexane-1,6-diamine)-mu-[diamine-platinum(II)]bis[diamine-(chloro)platinum(II)]-tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)-benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)-ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)colchic(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)-amino] benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2-, 1-c]quinolin-7-one, and dimesna.

"Antiproliferative agents" include antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxy-cytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]-glycylamino]-L-glycero-B-L-manno-heptopyranosyl]-adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetra cyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)-quinolinone, (−)-6-[amino(4-chlorophenyl-1)(1-methyl-1H-imidazol-5-yl) methyl]-4-(3-chlorophenyl)-1-methyl-2(1H)-quinolinone, (+)-6-[amino(4-chlorophenyl) (1-methyl-1H-imidazol-5-yl) methyl]-4-(3-chlorophenyl)-1-methyl-2(1H)-quinolinone, 5(S)-n-butyl-1-(2,3-dimethyl-phenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)-methyl]-2-piperazinone, 5(S)-n-butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]-piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2'] bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4] dioxa-azacyclononadecine-9-carbonitrile, (±)-19,20-dihydro-19-oxo-5H-18,21-ethano-12,14-etheno-6,10-metheno-22H-benzo[d]imidazo[4,3-k][1,6,9,12]-oxatriaza-cyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacyclo-eicosine-9-carbonitrile, and (±)-19,20-dihydro-3-methyl-19-oxo-5H-18,21-ethano-12,14-etheno-6,10-metheno-22H-benzo[d]imidazo[4,3-k][1,6,9, 12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see J. Of Cancer, Vol. 35, No. 9, pp. 1394-1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232, 632. Examples of reverse transcriptase inhibitors include delaviridine, efavirenz, GS-840, HBY097, lamivudine, nevirapine, AZT, 3TC, ddC, and ddI. It has been reported (Nat. Med.; 8(3):225-32, 2002) that HIV protease inhibitors, such as indinavir or saquinavir, have potent anti-angiogenic activities and promote regression of Kaposi sarcoma.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR[1]) and Flk-1/KDR (VEGFR[20]), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib, valecoxib, and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin., Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et at, J. Lab. Clin. Med. 105: 141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]-methyl]-1H-1,2,3-triazole-4-carboxamide, CM 101, squalamine, combretastatin, RP14610, NX[31838], sulfated mannopentose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of PDK (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include, but not limited to, activators of TNF receptor family members (including the TRAIL receptors).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include, but not limited to, tyrosine kinase inhibitors such as inhibitors of c-Kit, Eph, PDGF, Flt3, Lck, Btk, and c-Met. Further agents include inhibitors of RTKs shown as described by Bume-Jensen and Hunter, 2001, *Nature* 411: 355-365. Examples of "tyrosine kinase inhibitors" include, but not limited to, N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]-quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, ST1571, CEP2563, 4-(3-chlorophenylamino)-5,6-dimethyl-7-H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, SU11248, STI571A, N-4-chlorophenyl-4-(4-pyridylmethyl)-1-phthalazinamine, and EMD121974.

HDAC inhibitors are also useful in combination with platelet fibrinogen receptor (GP Iib/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, 1999, *Platelets* 10: 285-292). Therefore, HDAC inhibitors can serve to inhibit metastasis, in combination with GP Iib/IIIa) antagonists. Examples of other fibrinogen receptor antagonists include abciximab, eptifibatide, sibrafiban, lamifiban, lotrafiban, cromofiban, and CT50352.

As used above, "integrin blockers" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$; $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Other agents used in cancer therapy include those disclosed in U.S. patent publication 2005/0227929, herein incorporated by reference.

Commercially available anti-cancer agents which may be used in combination with an HDAC8 selective agent disclosed herein include, but are not limited to: abarelix (Plenaxis®); aldesleukin (Prokine®); Aldesleukin (Proleukin®); Alemtuzumab (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacizumab (Avastin®); bexarotene (Targretin®); bleomycin (Blenoxane®); bortezomib (Velcade®); busulfan (Busulfex®); busulfan (Myleran®); calusterone (Methosarb®); capecitabine Xeloda®); carboplatin Paraplatin®); carmustine (BCNU, BiCNU); carmustine (Gliadel®); celecoxib (Celebrex®); cetuximab (Erbitux®); chlorambucil (Leukeran®); cisplatin (Platinol®); cladribine (Leustatin®); clofarabine (Clolar®); cyclophosphamide (Cytoxan®); cytarabine (Cytosar-U®); cytarabine liposomal (DepoCyt); dacarbazine (DTIC-Dome); dactinomycin (actinomycin D, Cosmegen®); Darbepoetin alfa (Aranesp®); dasatinib (Sprycel®); daunorubicin liposomal (DanuoXome); daunorubicin (daunomycin, Daunorubicin®); daunorubicin (daunomycin, Cerubidine®); decitabine (Dacogen®); denileukin (Ontak®); dexrazoxane (Zinecard®); docetaxel (Taxotere®); doxorubicin (Adriamycin®); doxorubicin liposomal (Doxil®); dromostanolone propionate; epirubicin (Ellence®); Epirubicin; Epoetin alfa (EPOGEN®); erlotinib (Tarceva®); estramustine (Emcyt®); etoposide phosphate (Etopophos®); etoposide (VP-16; Vepesid®); exemestane (AROMASIN®); fentanyl citrate (Fentora®); Filgrastim (Neupogen®); floxuridine (FUDR); fludarabine (Fludara®); fluorouracil (5-FU, Adrucil®); fulvestrant (Faslodex®); gefitinib (Iressa®); gemcitabine (Gemzar®); gemtuzumab ozogamicin (Mylotarg®); goserelin acetate (Zoladex®); histrelin acetate (Histrelin®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Leucovorin®); Leuprolide Acetate (Eligard®); levamisole (Ergamisol®); lomustine, CCNU CeeBU®); meclorethamine (nitrogen mustard, Mustargen®); megestrol acetate (Megace®); melphalan (Alkeran®); mercaptopurine (6-MP, Purinethol®); mesna (Mesnex®); methotrexate (Rheumatrex®, Trexall®); methoxsalen (Uvadex®); mitomycin C (Mutamycin®); mitomycin C (Mitozytrex®); mitotane (Lysodren®); mitoxantrone (Novantrone®); nandrolone phenpropionate (Durabolin-50); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pegademase (Adagen®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide (VM-26, Vumon®); testolactone (Teslac®); thalidomide (Thalomid®); thioguanine (6-TG, Thioguanine®); thiotepa (Thioplex®); topotecan (Hycamtin®); toremifene (Fareston®); Tositumomab (Bexxar®); Tositumomab/I-131 tositumomab (Bexxar®); trastuzumab (Herceptin®); tretinoin (ATRA, Vesanoid®); Uracil Mustard; valrubicin (Valstar®); vinblastine (Velban®); vincristine (Oncovin®);

vinorelbine (Navelbine®); vorinostat (Zolinza®); zoledronate (Zometa®); and zoledronic acid (Zometa®).

The HDAC8 selective compounds described herein may be used in combination with gene therapy for the treatment of cancer. For an overview of genetic strategies to treating cancer see Hall et al. (*Am J Hum Genet* 61:785-789, 1997) and Kufe et al. (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), Duc-4, NF-I, NF-2, RB, WT1, BRCA1, BRCA2, a uPA/uPAR antagonist ("Adenoviras-Mediated Delivery of a uPA/uPAR Antagonist Suppresses Angiogenesis-Dependent Tumor Growth and Dissemination in Mice," *Gene Therapy*, August 1998, 5(8): 1105-13), and interferon-γ (*J. Immunol.* 2000; 164:217-222).

The HDAC8 selective compounds described herein may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

The HDAC8 selective compounds described herein may be employed in conjunction with anti-emetic agents to treat nausea or emesis, including acute, delayed, late-phase, and anticipatory emesis, which may result from the use of a HDAC8 selective compound described herein, alone or with radiation therapy. For the prevention or treatment of emesis, a HDAC8 selective compound described herein may be used in conjunction with anti-emetic agents, such as, but not limited to: neurokinin-1 receptor antagonists, 5HT3 receptor antagonists (such as ondansetron, granisetron, tropisetron, Palonosetron, and zatisetron), $GABA_B$ receptor agonists (such as baclofen), corticosteroids (such as dexamethasone, prednisone, prednisolone, or others such as disclosed in U.S. Pat. Nos. 2,789,118; 2,990,401; 3,048,581; 3,126,375; 3,929,768; 3,996,359; 3,928,326 and 3,749,712), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In one embodiment, an anti-emesis agent selected from among a neurokinin-1 receptor antagonist, a 5HT3 receptor antagonist and a corticosteroid is administered as an adjuvant for the treatment or prevention of emesis that may result upon administration of the instant compounds.

The HDAC8 selective compounds described herein may also be administered with an agent useful in the treatment of anemia. Such an anemia treatment agent is, for example, a continuous eythropoiesis receptor activator (such as epoetin-α).

The HDAC8 selective compounds described herein may also be administered with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

The HDAC8 selective compounds described herein may also be administered with an immunologic-enhancing drug, such as levamisole, bacillus Calmette-Guerin, octreotide, isoprinosine and Zadaxin.

The HDAC8 selective compounds described herein may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel®), pamidronate (Aredia®), alendronate (Fosamax®), risedronate (Actonel®), zoledronate (Zometa®), ibandronate (Boniva®), incadronate or cimadronate, clodronate, EB-1053, minodronate, neridronate, piridronate and tiludronate including any and all pharmaceutically acceptable salts, derivatives, hydrates and mixtures thereof.

The HDAC8 selective compounds described herein may also be useful for treating breast cancer in combination with aromatase inhibitors. Examples of aromatase inhibitors include but are not limited to: anastrozole, letrozole and exemestane.

The HDAC8 selective compounds described herein may also be useful for treating or preventing cancer in combination with siRNA or RNAi therapeutics.

"DNA methyltransferase inhibitor" refers to compounds which inhibit the methylation of the DNA base cytosine at the C-5 position of that base by the DNA methyltransferase enzyme. Examples of such DNA methyltransferase inhibitor include compounds disclosed in U.S. Pat. Nos. 6,329,412 and 6,268,137. Specific DNA methyltransferase inhibitors include 5-azacytosine and Zebularine®.

Radiation Therapy

Radiotherapy, also called radiation therapy, is the treatment of cancer and other diseases with ionizing radiation. Ionizing radiation deposits energy that injures or destroys cells in an area being treated (a "target tissue") by damaging their genetic material, making it impossible for these cells to continue to grow. Although radiation damages both cancer cells and normal cells, the latter are better able to repair themselves and function properly. Radiotherapy can be used to treat localized solid tumors, such as cancers of the skin, tongue, larynx, brain, breast, prostate, colon, uterus and/or cervix. It can also be used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α, β, and γ radiation and ultra violet light. Radiotherapy with or without concurrent or sequential chemotherapy is an effective modality for head and neck, breast, skin, anogenital cancers, and certain nonmalignant diseases such as keloid, desmoid tumor, hemangioma, arteriovenous malformation, and histocytosis X.

Provided are methods of using at least one histone deacetylase inhibitor to reduce side effect caused by at least one other therapeutic treatment, such as radiation-induced normal tissue fibrosis or chemotherapy-induced tissue necrosis, and the methods provided herein also synergistically inhibit tumor cell growth with radiotherapy and other anti-cancer agents.

Growth Hormone Secretagogues

A selective inhibitor of HDAC8 can be used in combination with one or more growth hormone secretagogues including, but not limited to, arginine, L-3,4-dihydroxyphenylalanine (1-Dopa), glucagon, vasopressin, PACAP (pituitary adenylyl cyclase activating peptide), muscarinic receptor agonists and a synthetic hexapeptide, GHRP (growth hormone releasing peptide).

Agents for Treating Autoimmune Diseases, Inflammatory Diseases, or Allergy Diseases Where the subject is suffering from or at risk of suffering from an autoimmune disease, an inflammatory disease, or an allergy disease, a selective HDAC8 inhibitor compound can be administered in any combination with one or more of the following therapeutic agents: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, or anticholinergics.

In one embodiment, selective HDAC8 inhibitor compounds described herein, or compositions and medicaments that include the selective HDAC8 inhibitor compounds described herein, may be administered to a patient in combination with an anti-inflammatory agent including, but not limited to, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketolorac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, CS-502, JTE-522, L-745,337 and NS398).

Combinations with NSAIDs, which are selective COX-2 inhibitors, are contemplated herein. Such compounds include, but are not limited to those disclosed in U.S. Pat. No. 5,474,995; U.S. Pat. No. 5,861,419; U.S. Pat. No. 6,001,843; U.S. Pat. No. 6,020,343, U.S. Pat. No. 5,409,944; U.S. Pat. No. 5,436,265; U.S. Pat. No. 5,536,752; U.S. Pat. No. 5,550,142; U.S. Pat. No. 5,604,260; U.S. Pat. No. 5,698,584; U.S. Pat. No. 5,710,140; WO 94/15932; U.S. Pat. No. 5,344,991; U.S. Pat. No. 5,134,142; U.S. Pat. No. 5,380,738; U.S. Pat. No. 5,393,790; U.S. Pat. No. 5,466,823; U.S. Pat. No. 5,633,272; and U.S. Pat. No. 5,932,598; all of which are hereby incorporated by reference. Other examples of specific inhibitors of COX-2 include those disclosed in U.S. Pat. No. 6,313,138 the disclosure of which is incorporated herein by reference in its entirety.

Compounds that have been described as selective COX-2 inhibitors and are therefore useful in the methods or pharmaceutical compositions described herein include, but are not limited to, celecoxib, rofecoxib, lumiracoxib, etoricoxib, valdecoxib, and parecoxib, or a pharmaceutically acceptable salt thereof.

Corticosteroids, include, but are not limited to: betamethasone (Celestone®), prednisone (Deltasone®), alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

Other agents used as anti-imflammatories include those disclosed in U.S. patent publication 2005/0227929, herein incorporated by reference.

Some commercially available anti-inflammatories include, but are not limited to: Arthrotec® (diclofenac and misoprostol), Asacol®, Salofalk® (5-aminosalicyclic acid), Auralgan® (antipyrine and benzocaine), Azulfidine® (sulfasalazine), Daypro® (oxaprozin), Lodine®(etodolac), Ponstan® (mefenamic acid), Solumedrol® (methylprednisolone), Bayer®, Bufferin® (aspirin), Indocin® (indomethacin), Vioxx® (rofecoxib), Celebrex® (celecoxib), Bextra® (valdecoxib), Arcoxia® (etoricoxib), Prexige® (lumiracoxib), Advil®, Motrin® (ibuprofen), Voltaren®(diclofenac), Orudis®(ketoprofen), Mobic®(meloxicam), Relafen® (nabumetone), Aleve®, Naprosyn® (naproxen), Feldene® (piroxicam).

In one embodiment, HDAC8 selective inhibitors are administered in combination with leukotriene receptor antagonists including, but are not limited to, BAY u9773, Cuthbert et al EP 00791576 (published 27 Aug. 1997), DUO-LT (Tsuji et al, *Org. Biomol. Chem.,* 1, 3139-3141, 2003), zafirlukast (Accolate®), montelukast (Singulair®), prankulast (Onon®), and derivatives or analogs thereof.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of HDAC, or in which HDAC is a mediator or contributor to the symptoms or cause.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

These examples are provided for illustrative purposes only and not to limit the scope of the claims provided herein. The starting materials and reagents used for the synthesis of the compounds described herein may be synthesized or can be obtained from commercial sources, such as, but not limited to, Aldrich Chemical Co. (Milwaukee, Wis.), Sigma Chemical Co. (St. Louis, Mo.), or Bachem (Torrance, Calif.).

Synthesis of Compounds

Example 1

Synthesis of 1-methyl-1H-indole-5-carboxylic acid methyl ester

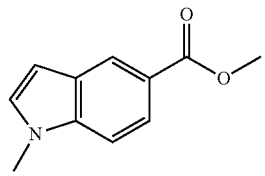

Step 1

A solution of 1H-indole-5-carboxylic acid (1.6 g, 10 mmol), sodium hydride (1.2 g, 30 mmol), iodomethane (6.2 mL, 100 mmol) and DMF (40 mL) was stirred and room temperature for 24 hr. The reaction mixture was then quenched with water (5 mL) and diluted with ether (150 mL) and ethyl acetate (50 mL). After washing with aq. $NH_4Cl$ (100 mL), water (100 mL) and then brine (100 mL), the organic layer was dried over $MgSO_4$, filtered and concentrated. The remaining material was subjected to flash chromatography (ethyl acetate/hexane 1:4) to provide 1-methyl-1H-indole-5-carboxylic acid methyl ester as a crystalline solid (1.77 g, 93% yield). $^1$H NMR (400 MHz, $CDCl_3$) δ 8.40 (s, 1H), 7.94 (d, 1H, J=9.0 Hz), 7.34 (d, 1H, J=9.0 Hz), 7.12 (d, 1H, J=2.9 Hz), 6.60 (d, 1H, J=2.9 Hz), 3.94 (s, 3H), 3.83 (s, 3H).

Example 2

Synthesis of 1-Cyclohexylmethyl-1H-indole-6-carboxylic acid hydroxyamide (Compound 15)

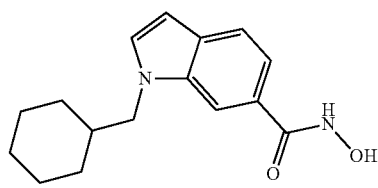 [SMILES: O=C(NO)c1ccc2ccn(CC3CCCCC3)c2c1]

Step 1

To a solution of commercially available 1H-indole-6-carboxylic acid methyl ester (0.35 g, 2.0 mmol) and cyclohexylmethyl bromide (0.31 mL, 2.2 mmol) in DMF (2 mL) was added sodium hydride (92 mg, 2.3 mmol). After stirring at room temperature for 3 hr, the solution was diluted with water (25 mL) and ethyl acetate (75 mL), the organic layer was washed again with dilute $NaHCO_3$ (25 mL) and then brine (25 mL). The organic layer was dried over $Na_2SO_4$, filtered and concentrated. The remaining residue was subjected to flash chromatography (ethyl acetate/hexane, 1:24) to provide 1-cyclohexylmethyl-1H-indole-6-carboxylic acid methyl ester as a white solid (0.40 g, 74% yield). $^1$H NMR (400 MHz, DMSO) δ 8.10 (s, 1H), 7.62 (m, 2H), 7.58 (d, 1H, J=3.1 Hz), 6.52 (d, 1H, J=3.1 Hz), 4.10 (d, 2H, J=7.4 Hz), 3.85 (s, 3H), 1.77 (m, 1H), 1.65-1.57 (m 3H), 1.46 (m, 2H), 1.19 (m, 3H), 0.98 (m, 2H).

Step 2

To a solution of sodium hydroxide (0.1 g, 2.5 mmol) and 50% aqueous hydroxyl amine (1 mL) was added 1-cyclohexylmethyl-1H-indole-6-carboxylic acid methyl ester (0.2 g, 0.7 mmol) dissolved in THF/MeOH (2 mL, 1:1). After stirring 3.5 hr at room temperature, the solution was diluted with water (4 mL) and the volatile solvents were removed in vacuo. The solution was then neutralized to pH=7-8 with 1N HCl. The resulting precipitate was isolated by filtration to provide 1-cyclohexylmethyl-1H-indole-6-carboxylic acid hydroxyamide as a white solid (0.16 g, 84% yield). $^1$H NMR (400 MHz, DMSO) δ 11.13 (s, 1H), 8.92 (s, 1H), 7.92 (s, 1H), 7.55 (d, 1H, J=8.0 Hz), 7.47-7.42 (m, 2H), 6.45 (d, 1H, J=3.1 Hz), 4.03 (d, 2H, J=7.4 Hz), 1.84 (m, 1H), 1.66-1.57 (m 3H), 1.47 (m, 2H), 1.12 (m, 3H), 0.98 (m, 2H).

Example 3

Synthesis of 1-(4-Difluoromethoxy-phenylmethyl)-1H-indole-6-carboxylic acid hydroxyamide (Compound 22)

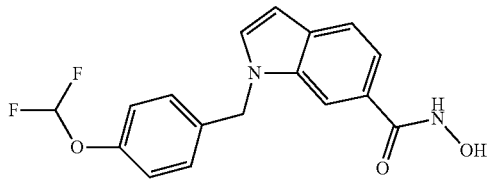 [SMILES: O=C(NO)c1ccc2ccn(Cc3ccc(OC(F)F)cc3)c2c1]

Step 1

To a solution of commercially available 1H-indole-6-carboxylic acid methyl ester (0.35 g, 2.0 mmol) and 4-difluoromethoxy-benzyl bromide (0.52 g, 2.2 mmol) in DMF (2 mL) was added sodium hydride (92 mg, 2.3 mmol). After stirring at room temperature for 3.5 hr, the solution was diluted with water (25 mL) and ethyl acetate (75 mL), the organic layer was washed again with dilute NaHCO$_3$ (25 mL) and then brine (25 mL). The organic layer was dried over Na$_2$SO$_4$, filtered and concentrated. The remaining residue was subjected to flash chromatography (ethyl acetate/hexane, 1:5) to provide 1-(4-difluoromethoxy-phenylmethyl)-1H-indole-6-carboxylic acid methyl ester as a colorless oil (0.14 g, 21% yield).

Step 2

To a solution of sodium hydroxide (0.1 g, 2.5 mmol) and 50% aqueous hydroxyl amine (1 mL) was added 1-(4-difluoromethoxy-phenylmethyl)-1H-indole-6-carboxylic acid methyl ester (0.14 g, 0.4 mmol) dissolved in THF/MeOH (2 mL, 1:1). After stirring 3 hr at room temperature, the solution was diluted with water (4 mL) and the volatile solvents were removed in vacuo. The solution was then neutralized to pH=7-8 with 1N HCl. The resulting precipitate was isolated by filtration to provide 1-(4-difluoromethoxy-phenylmethyl)-1H-indole-6-carboxylic acid hydroxyamide as a white powder (0.1 g, 75% yield). $^1$H NMR (400 MHz, DMSO) δ 11.13 (s, 1H), 8.92 (s, 1H), 7.96 (s, 1H), 7.67 (d, 1H, J=3.1 Hz), 7.59 (d, 1H, J=8.0 Hz), 7.45 (d, 1H, J=8.6 Hz), 7.27 (d, 2H, J=8.6 Hz), 7.17 (d, 1H, J=18 Hz), 7.13 (d, 2H, J=8.6 Hz), 6.55 (d, 1H, J=3.1 Hz), 5.47 (s, 2H).

Example 4

Synthesis of 1-(4-Methoxy-phenylmethyl)-1H-indole-6-carboxylic acid hydroxyamide (Compound 23)

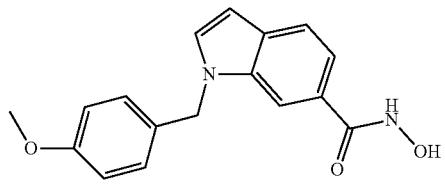 [SMILES: COc1ccc(Cn2ccc3ccc(C(=O)NO)cc32)cc1]

Step 1

To a solution of commercially available 1H-indole-6-carboxylic acid methyl ester (0.35 g, 2.0 mmol) and 4-methoxy-benzyl bromide (0.32 mL, 2.2 mmol) in DMF (2 mL) was added sodium hydride (92 mg, 2.3 mmol). After stirring at room temperature for 3.5 hr, the solution was diluted with water (25 mL) and ethyl acetate (75 mL), the organic layer was washed again with dilute NaHCO$_3$ (25 mL) and then brine (25 mL). The organic layer was dried over Na$_2$SO$_4$, filtered and concentrated. The remaining residue was subjected to flash chromatography (ethyl acetate/hexane, 1:5) to provide 1-(4-methoxy-phenylmethyl)-1H-indole-6-carboxylic acid methyl ester as a white solid (0.32 g, 54% yield). $^1$H NMR (400 MHz, DMSO) δ 8.10 (s, 1H), 7.73 (d, 1H, J=3.4 Hz), 7.64 (m, 2H), 7.14 (d, 2H, J=9.0 Hz), 6.88 (d, 2H, J=9.0 Hz), 6.58 (d, 1H, J=3.4 Hz), 5.45 (s, 2H), 3.83 (s, 3H), 3.70 (s, 3H).

Step 2

To a solution of sodium hydroxide (0.2 g, 5 mmol) and 50% aqueous hydroxyl amine (2 mL) was added 1-(4-methoxy-phenylmethyl)-1H-indole-6-carboxylic acid methyl ester (0.32 g, 1.0 mmol) dissolved in THF/MeOH (4 mL, 1:1). After stirring 1 hr at room temperature, the solution was diluted with water (4 mL) and the volatile solvents were removed in vacuo. The solution was then neutralized to pH=7-8 with 1N HCl. The resulting precipitate was isolated by filtration to provide 1-(4-methoxy-phenylmethyl)-1H-indole-6-carboxylic acid hydroxyamide as a white powder (0.25 g, 84% yield). $^1$H NMR (400 MHz, DMSO) δ 11.13 (s, 1H), 8.93 (s, 1H), 7.97 (s, 1H), 7.64 (d, 1H, J=3.2 Hz), 7.58 (d, 1H, J=8.9 Hz), 7.45 (d, 1H, J=8.3 Hz), 7.19 (d, 2H, J=8.3 Hz), 6.87 (d, 2H, J=8.3 Hz), 6.52 (d, 1H, J=3.2 Hz), 5.38 (s, 2H), 3.70 (s, 3H).

Example 5

Synthesis of 1-(N-methylsulfonyl-3-aminobenzyl)-1H-indole-6-carboxylic acid hydroxyamide (Compound 28)

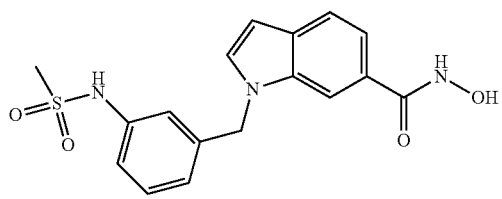 [SMILES: CS(=O)(=O)Nc1cccc(Cn2ccc3ccc(C(=O)NO)cc32)c1]

Step 1

To a solution of 1H-indole-6-carboxylic acid methyl ester (1.0 g, 5.7 mmol) and 3-nitrobenzyl bromide (1.48 g, 6.8 mmol) in DMF (15 mL) was added K$_2$CO$_3$ (1.6 g, 11.4 mmol). After stirring at room temperature for 16 hr, the solution was diluted with ethyl acetate (100 ml) and washed with water (3×50 ml). The organic layer was dried (MgSO$_4$), filtered and concentrated. The remaining residue was recrystallized with ethyl acetate/hexane to provide 1.34 g (76% yield) of 1-(3-nitrobenzyl)-1H-indole-6-carboxylic acid methyl ester as light orange crystals. $^1$H NMR (300 MHz, DMSO) δ 8.13 (m, 2H), 8.03 (s, 1H), 7.81 (d, 1H, J=3.0 Hz), 7.67-7.54 (m, 4H, J=9.0 Hz), 6.65 (d, 1H, J=3.0 Hz), 5.73 (s, 2H), 3.81 (s, 3H).

Step 2

To a solution of 1-(3-nitrobenzyl)-1H-indole-6-carboxylic acid methyl ester (1.3 g, 4.2 mmol) in MeOH (40 mL) and AcOH (3 ml) was added Zinc dust (1.9 g, 29 mmol). After stirring at room temperature for 3 hr, the solids were filtered and the filtrate was diluted with ethyl acetate (150 ml) and washed with sat. NaHCO$_3$ (200 ml). The organic layer was dried (MgSO$_4$), filtered and concentrated to collect 1.24 g (100% yield) of 1-(3-aminobenzyl)-1H-indole-6-carboxylic acid methyl ester. $^1$H NMR (300 MHz, DMSO) δ 8.02 (s, 1H), 7.64 (m, 3H), 6.92 (t, 1H, J=7.6 Hz), 6.58 (d, 1H, J=3.0 Hz), 6.40 (d, 1H, J=7.6 Hz), 6.27 (m, 2H), 5.36 (s, 2H), 5.07 (s, 2H), 3.81 (s, 3H).

Step 3

To a solution of 1-(3-aminobenzyl)-1H-indole-6-carboxylic acid methyl ester (0.35 g, 1.25 mmol) and methanesulfonyl chloride (0.11 ml, 1.37 mL) in THF (10 mL) was added TEA (1 mL). After stirring at 3.5 hr at room temperature, the mixture was diluted with ethyl acetate (100 mL) and washed with 1N HCl (150 mL). The organic layer was dried (MgSO$_4$), filtered and concentrated to collect a light yellow foam which was subjected to flash chromatography (50% ethyl acetate/hexane) to provide 0.41 g (92% yield) of 1-(3-methylsulfonamide-benzyl)-1H-indole-6-carboxylic acid methyl ester. $^1$H NMR (300 MHz, DMSO) δ 9.77 (s, 1H), 8.05 (s, 1H), 7.75 (m, 3H), 7.25 (t, 1H, J=7.6 Hz), 7.05 (m, 2H), 6.80 (d, 1H, J=7.6 Hz), 6.60 (m, 1H), 5.55 (s, 2H), 5.07 (s, 2H), 3.81 (s, 3H), 2.94 (s, 3H).

Step 4

To a solution of 1-(3-methylsulfonamide)-1H-indole-6-carboxylic acid methyl ester (0.41 g, 1.14 mmol) in MeOH (40 mL) and THF (5 mL) was added a premixed solution of sodium hydroxide (0.46 g, 11.4 mmol, dissolved in 2 mL of water) and 50% aqueous hydroxyl amine (1.1 ml). After stirring 3 hr at room temperature, the solution was diluted with water (50 ml) and the volatile solvents were removed in vacuo. The solution was then neutralized to pH=8-9 with 1N HCl. The resulting precipitate was isolated by filtration to provide 0.27 g (66% yield) of 1-(3-methylsulfonamide-benzyl)-1H-indole-6-carboxylic acid hydroxyamide. $^1$H NMR (300 MHz, DMSO) δ 8.90 (br s, 1H), 7.90 (s, 1H), 7.60 (m, 2H), 7.45 (m, 1H), 7.25 (t, 1H, J=7.6 Hz), 7.07 (m, 2H), 6.82 (d, 1H, J=7.6 Hz), 6.55 (m, 1H), 5.45 (s, 2H), 2.92 (s, 3H).

Example 6

Synthesis of 3-(Dimethylaminomethyl)-1-(4-methoxybenzyl)-1H-indole-6-carboxylic acid hydroxyamide (Compound 29)

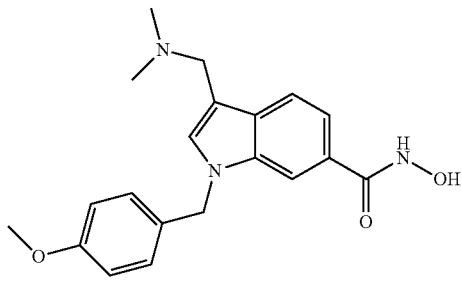 [SMILES: COc1ccc(Cn2cc(CN(C)C)c3ccc(C(=O)NO)cc32)cc1]

Step 1

To a solution of 3-formylindole-6-carboxylic acid methyl ester (2.05 g, 10.1 mmol) and 4-methoxybenzyl chloride (1.4 mL, 10.1 mmol) in DMF (20 mL) was added K$_2$CO$_3$ (4.2 g, 30.3 mmol). After stirring at room temperature for 16 hr, the solution was diluted with ethyl acetate (200 ml) and washed with water (4×100 ml). The organic layer was dried (MgSO$_4$), filtered and concentrated to collect 3.25 g (99% yield) of 3-formylindole-1-(4-methoxybenzyl)-6-carboxylic acid methyl ester as a tan solid.

Step 2

To a solution of 3-formylindole-1-(4-methoxybenzyl)-6-carboxylic acid methyl ester (0.43 g, 1.33 mmol) and dimethylamine (2.0M in THF, 2.0 mL, 4.0 mmol) in 1,2-dichloroethane (25 mL) was added sodium triacetoxyborohydride (0.56 g, 2.7 mmol). After stirring for 6.5 hr at room temperature, the solution was diluted with ethyl acetate (100 ml) and washed with dilute NaHCO$_3$ (100 mL). The organic layer was dried (MgSO$_4$), filtered and concentrated to collect 0.44 g (94% yield) of 3-(dimethylamino)methylindole-1-(4-methoxybenzyl)-6-carboxylic acid methyl ester as a tan oil. $^1$H NMR (300 MHz, DMSO) δ 8.05 (s, 1H), 7.72-7.60 (m, 3H), 7.12 (d, 2H, J=9.0 Hz), 6.85 (d, 2H, J=9.0 Hz), 5.40 (s, 2H), 3.83 (s, 3H), 3.68 (s, 3H), 3.53 (s, 2H), 2.13 (s, 6H).

Step 3

To a solution of 3-(dimethylamino)methylindole-1-(4-methoxybenzyl)-6-carboxylic acid methyl ester (0.44 g, 1.25 mmol) in MeOH (20 mL) was added a premixed solution of sodium hydroxide (0.5 g, 12.5 mmol, dissolved in 2 mL of water) and 50% aqueous hydroxyl amine (1.2 ml). After stirring 4 hr at room temperature, the solution was diluted with water (75 ml) and the volatile solvents were removed in vacuo. The solution was then neutralized to pH=8-9 with 1N HCl. The resulting precipitate was isolated by filtration to provide 0.156 g (35% yield) of 3-(dimethylamino)methylindole-1-(4-methoxybenzyl)-6-carboxylic acid hydroxyamide. $^1$H NMR (300 MHz, DMSO) δ 11.1 (br s, 1H), 8.9 (br s, 1H), 7.90 (s, 1H), 7.63-7.40 (m, 3H), 7.16 (d, 2H, J=9.0 Hz), 6.85 (d, 2H, J=9.0 Hz), 5.33 (s, 2H), 3.70 (s, 3H), 3.53 (s, 2H), 2.13 (s, 6H).

Example 7

Synthesis of 3-(N-Morpholinomethyl)-1-(4-methoxybenzyl)-1H-indole-6-carboxylic acid hydroxyamide (Compound 30)

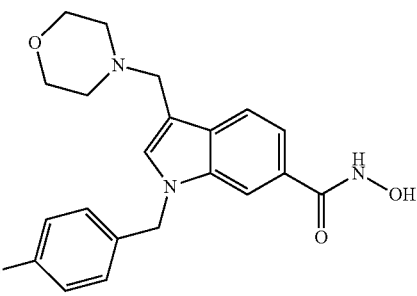

Step 1

To a solution of 3-formylindole-1-(4-methoxybenzyl)-6-carboxylic acid methyl ester (0.43 g, 1.33 mmol) and morpholine (0.35 mL, 4.0 mmol) in 1,2-dichloroethane (20 mL) was added sodium triacetoxyborohydride (0.56 g, 2.7 mmol). After stirring for 4 hr at room temperature, the solution was diluted with ethyl acetate (100 ml) and washed with dilute NaHCO$_3$ (100 mL). The organic layer was dried (MgSO$_4$), filtered and concentrated to collect 0.51 g (97% yield) of 3-(4-morpholino)methylindole-1-(4-methoxybenzyl)-6-carboxylic acid methyl ester. $^1$H NMR (300 MHz, DMSO) δ 8.05 (s, 1H), 7.73 (d, 1H, J=8.2 Hz), 7.62 (m, 2H), 7.12 (d, 2H, J=8.5 Hz), 6.86 (d, 2H, J=8.5 Hz), 5.40 (s, 2H), 3.82 (s, 3H), 3.68 (s, 3H), 3.62 (s, 2H), 3.54 (m, 4H), 2.36 (m, 4H).

Step 2

To a solution of 3-(4-morpholino)methylindole-1-(4-methoxybenzyl)-6-carboxylic acid methyl ester (0.59 g, 1.5 mmol) in MeOH (40 mL) was added a premixed solution of sodium hydroxide (0.6 g, 15 mmol, dissolved in 2 mL of water) and 50% aqueous hydroxyl amine (1.4 ml). After stirring 4 hr at room temperature, the solution was diluted with water (50 ml) and the volatile solvents were removed in vacuo. The solution was then neutralized to pH=8-9 with 1N HCl. The resulting precipitate was isolated by filtration to provide 0.477 g (80% yield) of 3-(4-morpholino)methylindole-1-(4-methoxybenzyl)-6-carboxylic acid hydroxyamide. $^1$H NMR (300 MHz, DMSO) δ 7.90 (s, 1H), 7.65 (d, 1H, J=8.2 Hz), 7.22 (s, 1H), 7.42 (d, 1H, J=8.2 Hz), 7.16 (d, 2H, J=8.9 Hz), 6.85 (d, 2H, J=8.9 Hz), 5.32 (s, 2H), 3.82 (s, 3H), 3.68 (s, 3H), 3.60 (s, 2H), 3.53 (m, 4H), 2.35 (m, 4H).

Example 8

Synthesis of 3-(N-Pyrrolidinomethyl)-1-(4-methoxybenzyl)-1H-indole-6-carboxylic acid hydroxyamide (Compound 31)

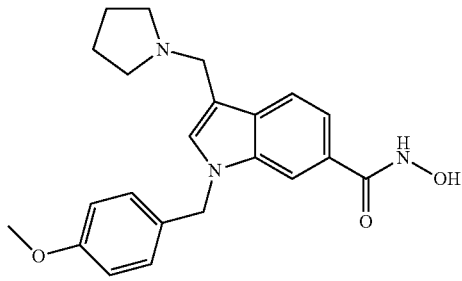 [SMILES: COc1ccc(Cn2cc(CN3CCCC3)c3ccc(C(=O)NO)cc32)cc1]

Step 1

To a solution of 3-formylindole-1-(4-methoxybenzyl)-6-carboxylic acid methyl ester (0.45 g, 1.39 mmol) and pyrrolidine (0.34 mL, 4.2 mmol) in 1,2-dichloroethane (20 mL) was added sodium triacetoxyborohydride (0.59 g, 2.8 mmol). After stirring for 5 hr at room temperature, the solution was diluted with ethyl acetate (150 ml) and washed with dilute NaHCO$_3$ (200 mL). The organic layer was dried (MgSO$_4$), filtered and concentrated to collect 0.54 g (100% yield) of 3-(1-pyrrolidino)methylindole-1-(4-methoxybenzyl)-6-carboxylic acid methyl ester.

Step 2

To a solution of 3-(1-pyrrolidino)methylindole-1-(4-methoxybenzyl)-6-carboxylic acid methyl ester (0.54 g, 1.43 mmol) in MeOH (50 mL) was added a premixed solution of sodium hydroxide (0.57 g, 14.3 mmol, dissolved in 2 mL of water) and 50% aqueous hydroxyl amine (1.3 ml). After stirring 4 hr at room temperature, the solution was diluted with water (50 ml) and the volatile solvents were removed in vacuo. The solution was then neutralized to pH=8-9 with 1N HCl. The resulting precipitate was isolated by filtration to provide 0.30 g (55% yield) of 3-(1-pyrrolidino)methylindole-1-(4-methoxybenzyl)-6-carboxylic acid hydroxyamide. $^1$H NMR (300 MHz, DMSO) δ 7.89 (s, 1H), 7.62 (d, 1H, J=8.2 Hz), 7.50 (s, 1H), 7.42 (d, 1H, J=8.2 Hz), 7.16 (d, 2H, J=8.6 Hz), 6.85 (d, 2H, J=8.6 Hz), 5.32 (s, 2H), 3.71 (s, 2H), 3.68 (s, 3H), 2.43 (m, 4H), 1.65 (m, 4H).

Example 9

Synthesis of 3-(N-Benzylaminomethyl)-1-(4-methoxybenzyl)-1H-indole-6-carboxylic acid hydroxyamide (Compound 32)

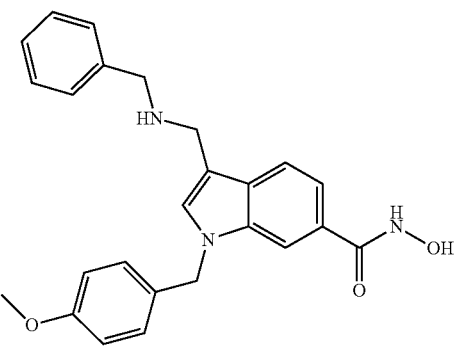 [SMILES: COc1ccc(Cn2cc(CNCc3ccccc3)c3ccc(C(=O)NO)cc32)cc1]

Step 1

To a solution of 3-formylindole-1-(4-methoxybenzyl)-6-carboxylic acid methyl ester (0.45 g, 1.39 mmol) and benzylamine (0.16 mL, 1.46 mmol) in MeOH (40 mL) was added Mg SO$_4$ (2 large spatula scoops) and AcOH (0.1 mL). The mixture was stirred at room temperature for 24 hr, then sodium borohydride (79 mg, 2.1 mmol) was added. 2 hr later, the mixture was diluted with ethyl acetate (150 mL) and washed with dilute NaHCO$_3$ (200 mL) The organic layer was dried (MgSO$_4$), filtered and concentrated and the resulting material was subjected to flash chromatography (50% ethyl acetate/hexane) to provide 0.25 g (43% yield) of 3-(N-benzylamino)methylindole-1-(4-methoxybenzyl)-6-carboxylic acid methyl ester. $^1$H NMR (300 MHz, DMSO) δ 8.07 (s, 1H), 7.72-7.58 (m, 3H), 7.35-7.20 (m, 5H), 7.17 (d, 2H, J=8.5 Hz), 6.86 (d, 2H, J=8.5 Hz), 5.40 (s, 2H), 3.82 (s, 5H), 3.72 (s, 2H), 3.68 (s, 3H).

Step 2

To a solution of 3-(N-benzylamino)methylindole-1-(4-methoxybenzyl)-6-carboxylic acid methyl ester (0.25 g, 0.60 mmol) in MeOH (25 mL) was added a premixed solution of sodium hydroxide (0.24 g, 6.0 mmol, dissolved in 2 mL of water) and 50% aqueous hydroxyl amine (0.6 ml). After stirring 16 hr at room temperature, the solution was diluted with water (50 ml) and the volatile solvents were removed in vacuo. The solution was then neutralized to pH=8-9 with 1N HCl. The resulting precipitate was isolated by filtration to provide 0.20 g (80% yield) of 3-(N-benzylamino)methylindole-1-(4-methoxybenzyl)-6-carboxylic acid hydroxyamide. $^1$H NMR (300 MHz, DMSO) δ 7.91 (s, 1H), 7.61 (m, 1H), 7.50 (s, 1H), 7.40 (m, 1H), 7.35-7.27 (m, 3H), 7.24-7.12 (m, 4H), 6.85 (d, 2H, J=8.5 Hz), 5.32 (s, 2H), 3.82 (s, 2H), 3.70 (s, 2H), 3.68 (s, 3H).

Example 10

Synthesis of 3-(Ethyl)-1-(4-methoxybenzyl)-1H-indole-6-carboxylic acid hydroxyamide (Compound 33)

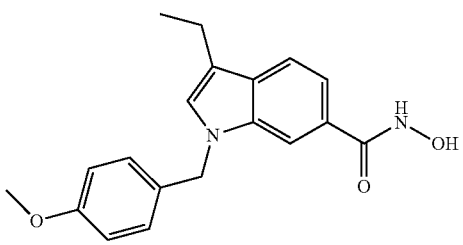 [SMILES: CCc1cn(Cc2ccc(OC)cc2)c2cc(C(=O)NO)ccc12]

Step 1

To a solution of acetyl chloride (0.23 mL, 3.3 mmole) and aluminum chloride (0.88 g, 6.6 mmol) in methylene chloride (30 mL) was added 1H-indole-6-carboxylic acid methyl ester (0.53 g, 3.0 mmol). After stirring 1 hr at room temperature water (300 mL) was added and then this was extracted with ethyl acetate (300 mL). The organic layer was dried (MgSO$_4$), filtered and concentrated to collect 0.65 g (99% yield) of 3-acetyl-1H-indole-6-carboxylic acid methyl ester a light yellow solid. $^1$H NMR (300 MHz, DMSO) δ 12.27 (s, 1H), 8.52 (s, 1H), 8.24 (d, 1H, J=8.2 Hz), 8.08 (d, 1H, J=1.0 Hz), 7.78 (dd, 1H, J=8.2, 1.0 Hz), 3.86 (s, 3H), 2.47 (s, 3H).

Step 2

To a solution of 3-acetyl-1H-indole-6-carboxylic acid methyl ester (0.65 g, 3.0 mmole) in THF (30 mL) was added BH$_3$-THF (1.0M, 9 mL, 9 mmol). The solution was heated to reflux and then more BH$_3$-THF (5 mL) was added. After allowing to cool and stirring for 2 hr at room temperature, the solvent was removed and the remaining material was diluted in ethyl acetate (100 mL) and washed with dilute NaHCO$_3$ (200 mL). The organic layer was dried (MgSO$_4$), filtered and concentrated. The remaining material was subjected to flash chromatography (25% ethyl acetate/hexanes) to collect 0.45 g (74% yield) of 3-ethyl-1H-indole-6-carboxylic acid methyl ester.

Step 3

To a solution of 3-ethyl-1H-indole-6-carboxylic acid methyl ester (0.45 g, 2.2 mmol) and 4-methoxybenzyl chloride (0.33 ml, 2.4 mmol) in DMF (10 mL) was added sodium hydride (60% wt, 64 mg, 2.6 mmol). After stirring 2 hr at room temperature, MeOH was added (2 mL) and then water (100 mL). The water was then extracted with ethyl acetate (3×50 mL). The organic layer was dried (MgSO$_4$), filtered and concentrated to collect an orange oil which was subjected to flash chromatography (15% ethyl acetate/hexane) to provide 1.0 g of 3-ethylindole-1-(4-methoxybenzyl)-6-carboxylic acid methyl ester. 4-methoxy benzyl chloride remains with the product.

Step 4

To a crude mixture of 3-ethylindole-1-(4-methoxybenzyl)-6-carboxylic acid methyl ester (1.0 g, 3.1 mmol) in MeOH (20 mL) was added NaOH (0.47 g, 12 mmol, dissolved in 5 ml of water). The solution was heated to 50° C. for 24 hr, then cooled to room temperature, diluted with water (300 ml), acidified with 1N HCl and then extracted into ethyl acetate (150 mL). The organic layer was dried (MgSO$_4$), filtered and concentrated and the resulting material was subjected to flash chromatography (50% ethyl acetate/hexane) to provide 0.47 g (49% yield) of 3-ethylindole-1-(4-methoxybenzyl)-6-carboxylic acid as an off-white solid. $^1$H NMR (300 MHz, DMSO) δ 8.01 (s, 1H), 7.58 (m, 2H), 7.47 (s, 1H), 7.13 (d, 2H, J=8.5 Hz), 6.85 (d, 2H, J=8.5 Hz), 5.35 (s, 2H), 3.68 (s, 3H), 2.71 (q, 2H, J=7.3 Hz), 1.25 (t, 3H, J=7.3 Hz).

Step 5

To a solution of 3-ethylindole-1-(4-methoxybenzyl)-6-carboxylic acid (0.46 g, 1.5 mmol) in THF (15 mL) and DMF (2 drops) was added oxalyl chloride (0.17 g, 1.9 mmol). After stirring at room temperature for 1.5 hr, the THF was removed and the resulting oil was dried under high vacuum. The oil was restirred in THF (10 mL) and then aqueous hydroxyl amine (50% wt/H$_2$O, 3 mL) was added. After stirring the solution for 30 min at room temperature, the solvent was removed and then water (100 mL) was added. NaOH (0.5 g) was added, then the pH was adjusted to ~8 (1N HCl) upon which a precipitate formed. The mixture was stirred 16 hr at room temperature, then extracted with ethyl acetate (200 mL). The organic layer was dried (MgSO$_4$), filtered and concentrated to collect 0.45 g (93% yield) of 3-ethylindole-1-(4-methoxybenzyl)-6-carboxylic acid hydroxyamide as a tan solid. $^1$H NMR (300 MHz, DMSO) δ 11.05 (br s, 1H), 8.87 (s, 1H), 7.90 (s, 1H), 7.53 (d, 1H, J=8.2 Hz), 7.40 (m, 2H), 7.16 (d, 2H, J=8.5 Hz), 6.85 (d, 2H, J=8.5 Hz), 5.29 (s, 2H), 3.68 (s, 3H), 2.70 (q, 2H, J=7.5 Hz), 1.24 (t, 3H, J=7.5 Hz).

Example 11

Synthesis of 3-(4-Benzoylamino-benzyl)-1-methyl-1H-indole-5-carboxylic acid hydroxyamide (Compound 36)

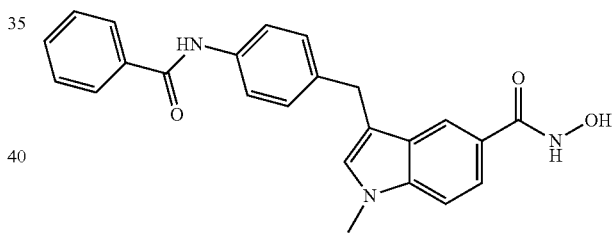

Step 1

A solution of 1-methyl-1H-indole-5-carboxylic acid methyl ester (0.38 g, 2.0 mmol), prepared using procedures as described in Example 1, Ag$_2$O (0.51 g, 2.2 mmol), 4-nitrobenzyl bromide (0.48 g, 2.2 mmol) and dioxane (6 mL) was heated to reflux for 25 hr, then more 4-nitrobenzyl bromide (0.48 g, 2.2 mmol) was added and the solution was heated at reflux an additional 4 days. After cooling to room temperature, the reaction mixture was diluted with ether (50 mL) and ethyl acetate (50 mL), washed with aq. NH$_4$Cl (50 mL) and then brine (50 mL). The organic layer was dried over MgSO$_4$, filtered and concentrated. The remaining residue was subjected to flash chromatography (ethyl acetate/hexane, 1:4) to provide of 1-methyl-3-(4-nitro-phenylmethyl)-1H-indole-5-carboxylic acid methyl ester (0.38 g, 58% yield). $^1$H NMR (400 MHz, CDCl$_3$) δ 8.26 (s, 1H), 8.16 (d, 2H, J=8.3 Hz), 7.98 (d, 1H, J=8.3 Hz), 7.45 (d, 2H, J=8.3 Hz), 7.35 (d, 1H, J=8.3 Hz), 6.90 (s, 1H), 4.25 (s, 2H), 3.94 (s, 3H), 3.82 (s, 3H).

Step 2

A mixture of 1-methyl-3-(4-nitro-phenylmethyl)-1H-indole-5-carboxylic acid methyl ester (0.23 g, 0.71 mmol), Pd (10% on carbon, 30 mg) and methanol (5 mL) was stirred under a hydrogen atmosphere (ballon) for 6 hr. The catalyst was removed by filtration and the solvents removed in vacuo to provide of 3-(4-amino-benzyl)-1-methyl-1H-indole-5-carboxylic acid methyl ester (0.19 g, 92% yield).

Step 3

A solution of 3-(4-amino-phenylmethyl)-1-methyl-1H-indole-5-carboxylic acid methyl ester (62 mg, 0.21 mmol), DIPEA (0.06 mL, 0.32 mmol), benzoyl chloride (0.03 mL, 0.23 mmol) and THF (5 mL) was stirred for 10 hr at room temperature. The solution was then diluted with ether (20 mL) and ethyl acetate (20 mL) and washed with aq. NaHCO$_3$ (50 mL). The organic layer was dried over MgSO$_4$, filtered and concentrated. The remaining residue was subjected to flash chromatography (ethyl acetate/hexane, 2:3) to provide 3-(4-benzoylamino-phenylmethyl)-1-methyl-1H-indole-5-carboxylic acid methyl ester (69 mg, 83% yield).

Step 4

A solution of 3-(4-benzoylamino-phenylmethyl)-1-methyl-1H-indole-5-carboxylic acid methyl ester (69 mg, 0.17 mmol), sodium hydroxide (21 mg, 0.52 mmol), methanol (3 mL), water (1 mL) and THF (3 mL) was heated to 60° C. for 24 hr. The reaction solution was then cooled to room temperature and concentrated in vacuo. The remaining residue was diluted with ethyl acetate (20 mL) and washed with 1N HCl (20 mL). The organic layer was dried over MgSO$_4$, filtered and concentrated to provide 3-(4-benzoylamino-phenylmethyl)-1-methyl-1H-indole-5-carboxylic acid (64 mg, 98% yield).

Step 5

A solution of 3-(4-benzoylamino-phenylmethyl)-1-methyl-1H-indole-5-carboxylic acid (64 mg, 0.16 mmol), DIPEA (0.14 mL, 0.8 mmol), HATU (68 mg, 0.18 mmol), hydroxyl amine hydrochloride (56 mg, 0.8 mmol) and DMF (4 mL) was stirred for 19 hr at room temperature. The reaction mixture was then subjected to HPLC purification to provide 3-(4-benzoylamino-phenylmethyl)-1-methyl-1H-indole-5-carboxylic acid hydroxyamide (22 mg, 34% yield). $^1$H NMR (400 MHz, DMSO) δ 11.06 (s, 1H), 10.18 (s, 1H), 7.99 (s, 1H), 7.93 (d, 2H, J=7.2 Hz), 7.67 (d, 2H, J=8.7 Hz), 7.57 (m, 2H), 7.53 (d, 2H, J=7.7 Hz), 7.43 (d, 1H, J=8.2 Hz), 7.27 (d, 2H, J=8.2 Hz), 7.19 (s, 1H), 4.03 (s, 2H), 3.76 (s, 3H).

Example 12

Synthesis of 3-(4-Fluoro-phenylmethyl)-1-methyl-1H-indole-5-carboxylic acid hydroxyamide (Compound 39)

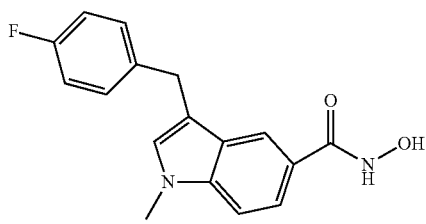 [SMILES: Cn1cc(Cc2ccc(F)cc2)c2cc(C(=O)NO)ccc21]

Step 1

A solution of 1-methyl-1H-indole-5-carboxylic acid methyl ester (0.17 g, 0.9 mmol), prepared using procedures as described in Example 1, Ag$_2$O (0.22 g, 0.95 mmol), 4-fluoro-benzyl bromide (0.18 g, 0.95 mmol) and dioxane (4 mL) were heated to reflux for 16 hr, then more 4-fluoro-benzyl bromide (90 mg, 0.5 mmol) was added and the solution was heated at reflux an additional 4 hr. After cooling to room temperature, the reaction mixture was diluted with ether (60 mL), washed with aq. NH$_4$Cl (50 mL) and then brine (50 mL). The organic layer was dried over MgSO$_4$, filtered and concentrated. The remaining residue was subjected to flash chromatography (ethyl acetate/hexane, 1:3) to provide 3-(4-fluoro-phenylmethyl)-1-methyl-1H-indole-5-carboxylic acid methyl ester (58 mg, 22% yield).

Step 2

To a solution of sodium hydroxide (64 mg, 1.6 mmol) and 50% aqueous hydroxyl amine (0.65 mL) was added 3-(4-fluoro-phenylmethyl)-1-methyl-1H-indole-5-carboxylic acid methyl ester (58 mg, 0.2 mmol) dissolved in THF/MeOH (1 mL, 1:1). After stirring 4 hr at room temperature, the solution was diluted with water (4 mL) and the volatile solvents were removed in vacuo. The solution was then neutralized to pH=7-8 with 1N HCl and then subjected to HPLC purification to provide 3-(4-fluoro-phenylmethyl)-1-methyl-1H-indole-5-carboxylic acid hydroxyamide (32 mg, 50% yield). $^1$H NMR (400 MHz, DMSO) δ 11.05 (s, 1H), 8.83 (br s, 1H), 7.97 (s, 1H), 7.57 (dd, 1H, J=1.7, 8.6 Hz), 7.41 (d, 1H, J=8.6 Hz) 7.30 (m, 2H), 7.18 (s, 1H), 7.08 (m, 2H), 4.03 (s, 2H), 3.74 (s, 3H).

Example 13

Synthesis of acetyl-Gly-Ala-(N-acetyl-Lys)-AMC tert-Boc (N-Acetyl-Lys)-AMC (445 mg, 1 mmol, purchased from Bachem) was dissolved in 4 M HCL in dioxane to provide H—(N-acetyl-Lys)-AMC as a white solid. To a solution of H—(N-acetyl-Lys)-AMC in DMF (5 mL) was added Ac-Gly-Ala-OH (188 mg, 1 mmol) using PyBOP (520 mg, 1 mmol), HOBt (135 mg, 1 mmol), and NMM (0.296 mL, 2 mmol). The reaction mixture was stirred for 1 h and monitored by MS/LC for the presence of H—(N-acetyl-Lys)-AMC. Additional amounts of PyBOP (260 mg, 0.5 mmol), HOBt (70 mg, 0.5 mmol), and NMM (0.146 mL, 1 mmol) was added and the stirring was continued for additional 4 h after which the product was isolated in quantitative yield.

Biological Examples

Example 14

HDAC8 Expression is Highest in Pancreatic Delta Cells of the Islets of Langerhans HDAC8 expression was assessed by immunocytochemistry in a normal human multi-tissue panel paraffin-embedded and formalin fixed prior to antibody staining. Detection of HDAC8 was replicated using two independently derived anti-HDAC8 antibodies, HDAC8-SC11405, (Santa Cruz Biotechnology catalog#SC-11405, rabbit polyclonal) and HDAC8-Celera, at an optimal concentration of 10 µg/ml. Primary antibody labeling was detected using a Vector anti-rabbit secondary (BA-1000), and a Vector ABC-AP kit (AK-5000) with a Vector Red substrate kit (SK-5100). As shown in FIG. 1, HDAC8 expression was found to be highest in pancreatic islets (islets of Langerhans) and in small intestine.

In a follow-up experiment, pancreatic tissue double-labeling immunocytochemistry was performed for HDAC8+insulin; HDAC8+glucagon; and HDAC8+somatostatin (FIG. 2). Significantly, HDAC8 expression was co-localized specifically with somatostatin, a polypeptide marker of pancreatic delta cells.

HDAC8 expression was also detected in plasma cells (FIG. 3).

Based on these data, it was concluded that under normal physiological conditions, HDAC8 expression is highest in pancreatic islet cells expressing somatostatin (i.e., delta cells), and may play a role in driving somatostatin expression

Example 15

HDAC8 is Expressed in Tumor Cell Lines, and its Knock-Down Results in Apoptosis HDAC8 expression was determined by immunoblotting and quantitative RT-PCR (Q-PCR) in a variety of tumor cell lines including the Ramos, Raji, DHL-4, Jurkat, HuT78, DB, K562, A549, HCT-116, MCF-7, OVCR-3, PC3, RKO, and U87 cell lines.

Figure 4:
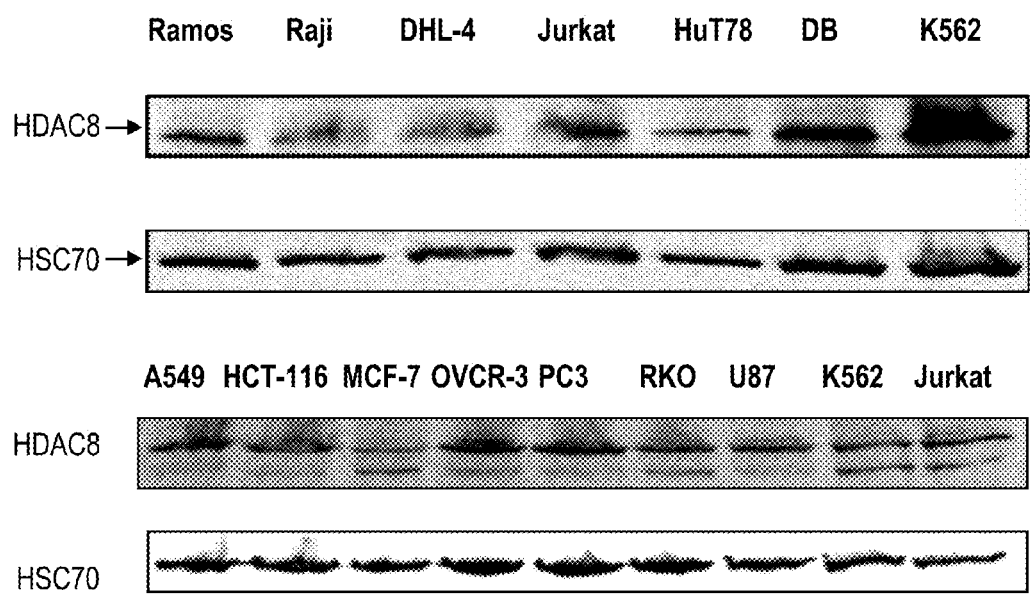
FIG. 4 is an illustrative immunoblot showing HDAC8 expression in a series of cell lines. For each cell line, Hsc 70 expression is also shown as a normalization control for apparent HDAC8 expression levels.

HDAC8 expression was detected by in all tumor cell lines (FIG. 4), in contrast to the highly restricted expression pattern observed in normal tissues.

Figure 5:
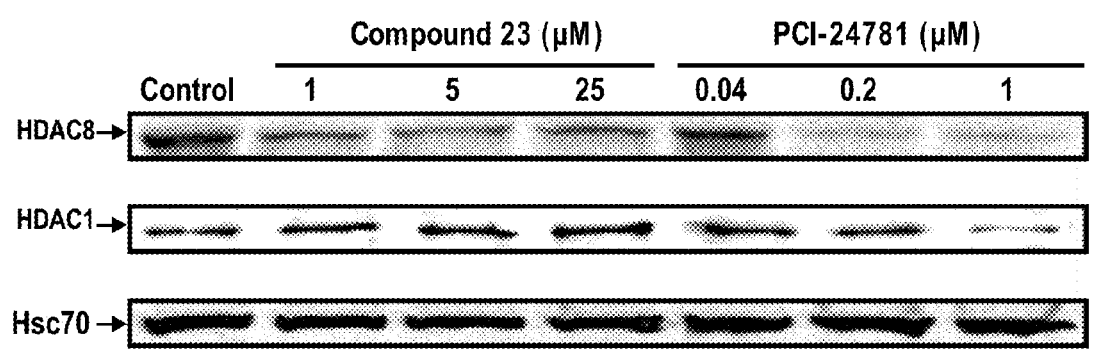
FIG. 5 illustrates that HDAC8 protein expression is modulated in a dose-dependent manner by both the HDAC8-selective inhibitor compound 23 and the pan-HDAC inhibitor PCI-24781.

As shown in FIG. 5. HDAC8 protein expression is modulated in a dose-dependent manner by both the HDAC8-selective inhibitors and the pan-HDAC inhibitor PCI-24781. Western blot of HDAC8 & HDAC1 after 24 hr treatment in Jurkat cells were obtained. HDAC1 levels are decreased by PCI-24781 but not by compound 23, whereas HDAC8 is affected by both treatments. Thus HDAC8 protein levels could be a pharmacodynamic marker for selective HDAC8 inhibitor compounds.

Figure 6:
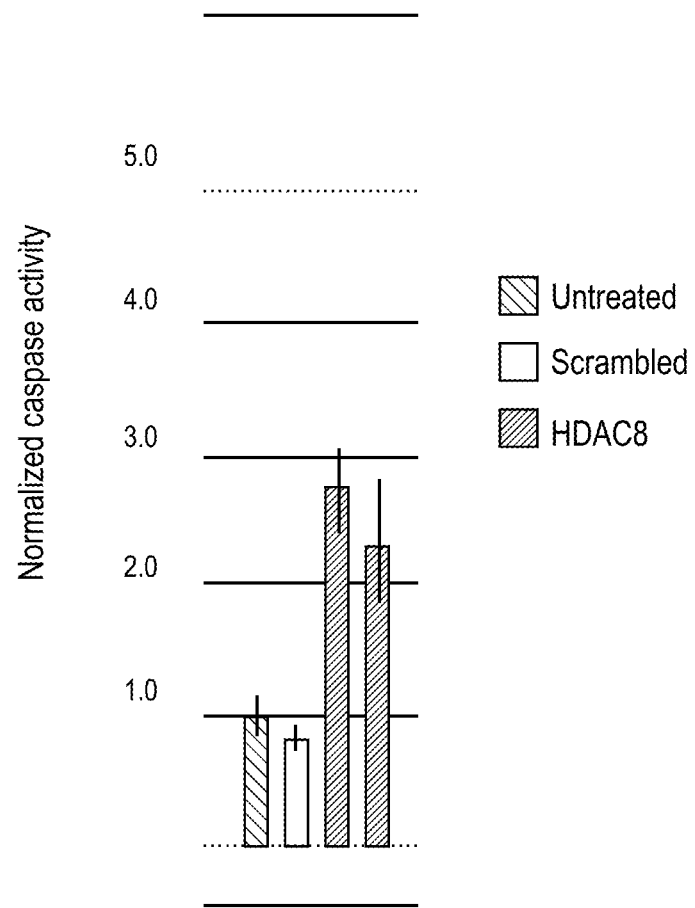
FIG. 6 is an illustrative bar graph showing the effect of RNAi knock-down of HDAC8 on apoptosis in HeLa cells. HDAC8 knockdown leads to apoptosis.
Figure 7:
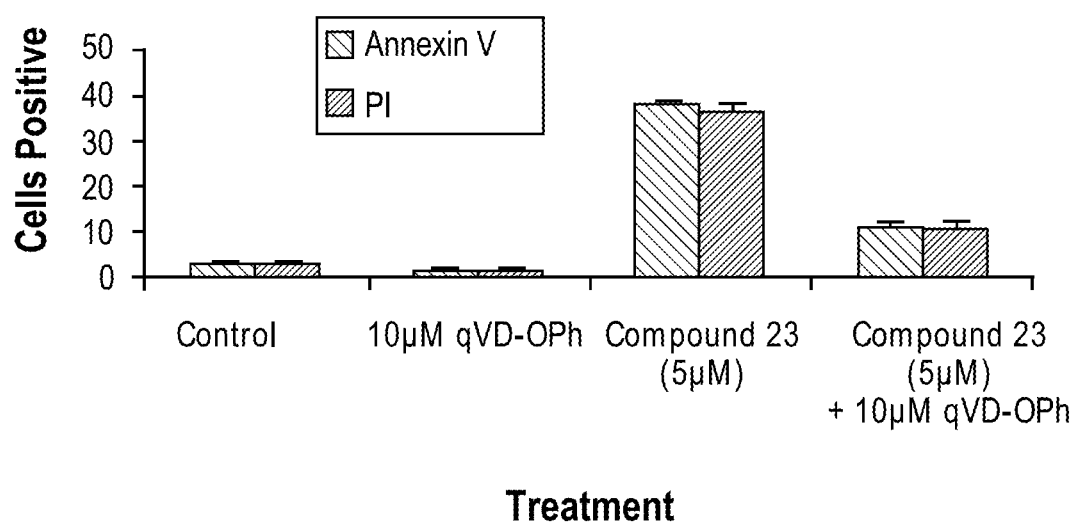
FIG. 7 illustrates that apoptosis induced by compound 23 is blocked by a pan-caspase inhibitor. Apoptosis was measured by annexin-V/propidium iodide flow cytometry. Apoptosis was induced by compound 23 and blocked by 10 uM qVD-OPh.
Figure 8A:
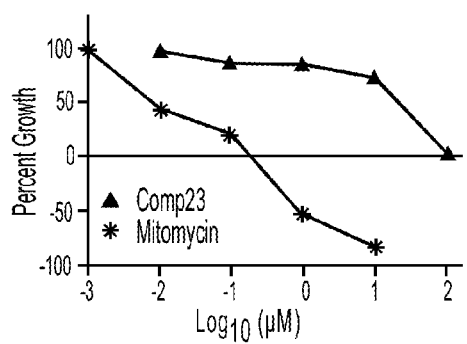
FIGS. 8A-D are illustrative panels of scatter plots showing the effect of the HDAC8-selective inhibitor compound, compound 23, on cell proliferation in four cell lines.
Figure 8B:
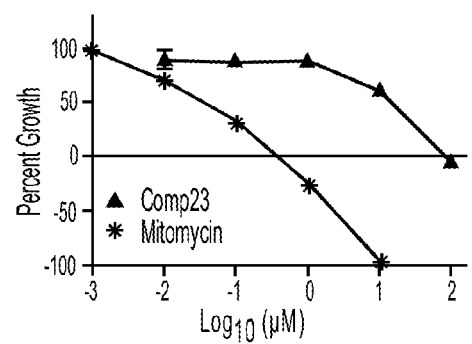
Figure 8C:
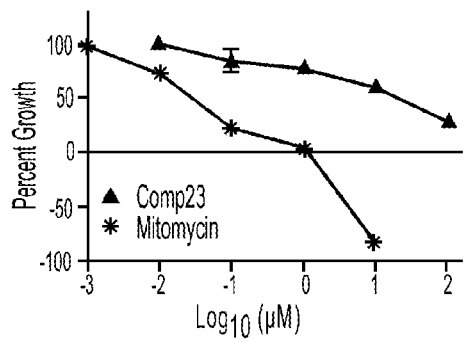
Figure 8D:
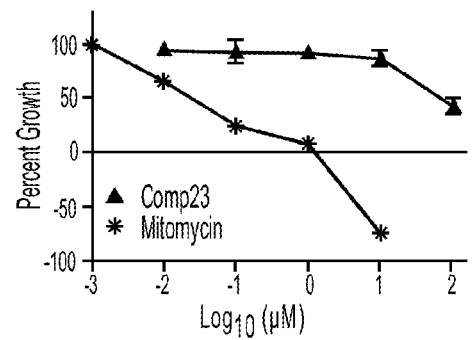

RNAi knockdown of HDAC8 in HeLa cells was shown to induce apoptosis as demonstrated by increased caspase activity (FIG. 6). As shown in FIG. 7, apoptosis (measured by annexin-V/propidium iodide flow cytometry) induced by 5 µM compound 23 is blocked by 10 µM qVD-OPh, which is a pan-caspase inhibitor.

Example 16

Inhibition of HDAC Activity In Vitro

Candidate selective HDAC8 inhibitor compounds, were assayed for their ability to inhibit, in vitro, HDAC8 deacetylase activity, as well as deacetylase activity of HDACs 1, 2, 3, 6, and 10. $IC_{50}$ values were determined as outlined in Schultz et. al., "Kinetics and Comparative Reactivity of Human Class I and Class IIb Histone Deacetylases" *Biochemistry*, 43 (34), 11083-11091, 2004. For comparison, broad spectrum HDAC inhibitors, CRA-024781 and suberoylanilide hydroxamic acid (SAHA), were also assayed in parallel. Inhibition constants were obtained using the program BatchKi (Kuzmic et al. *Anal. Biochem.* 2000, 286, 45-50).

The results are summarized in Table 4 below. Methods for determining HDAC activity in vivo or in vitro are known in the art, as disclosed in, e.g., Kim et al. (2006), *Methods Mol Biol.*, 325:273-283.

TABLE 4

Comparison of HDAC $IC_{50}$ values of pan-HDAC inhibitors vs HDAC8-selective inhibitors

| Compound No. | HDAC8 IC50 | HDAC-1/ HDAC-8 | HDAC-2/ HDAC-8 | HDAC-3/ HDAC-8 | HDAC-6/ HDAC-8 | HDAC-10/ HDAC-8 |
|---|---|---|---|---|---|---|
| CRA-024781 (broad spectrum) | E | C | C | C | C | C |
| SAHA (broad spectrum) | E | C | C | C | C | C |
| 1 | D | A | nd | nd | nd | nd |
| 2 | D | A | nd | nd | nd | nd |
| 3 | E | A | nd | nd | nd | nd |
| 4 | D | A | nd | nd | nd | nd |
| 5 | D | A | nd | nd | nd | nd |
| 6 | D | A | nd | nd | nd | nd |
| 7 | D | A | nd | nd | nd | nd |
| 8 | D | A | nd | nd | nd | nd |
| 9 | D | A | nd | nd | nd | nd |
| 10 | D | A | nd | nd | nd | nd |
| 11 | D | A | nd | nd | nd | nd |
| 12 | D | A | nd | nd | nd | nd |
| 13 | D | A | nd | nd | nd | nd |
| 14 | D | A | nd | nd | nd | nd |
| 15 | D | A | nd | nd | nd | nd |
| 16 | D | B | nd | nd | nd | nd |
| 17 | D | B | nd | nd | nd | nd |
| 18 | D | B | nd | nd | nd | nd |
| 19 | D | B | nd | nd | nd | nd |
| 20 | D | B | nd | nd | nd | nd |
| 21 | D | B | nd | nd | nd | nd |
| 22 | D | B | nd | nd | nd | nd |
| 23 | D | B | B | B | B | B |
| 34 | D | A | B | A | A | B |
| 35 | D | A | nd | nd | nd | nd |
| 36 | D | A | nd | nd | nd | nd |
| 37 | D | A | nd | nd | nd | nd |
| 38 | D | A | nd | nd | nd | nd |
| 39 | D | B | B | A | A | B |

Key: A >10 and <100; B >100; C <2; D <100 nM; E >100 nM.

The data presented above show that compounds described herein are selective inhibitors of HDAC8. Compounds described herein have HDAC8 $IC_{50}$ values that are less than 100 nM, and are at least 10 fold less than $IC_{50}$ values for other HDAC isoforms (HDAC1, HDAC2, HDAC3, HDAC6, HDAC10). In comparison, pan-HDAC inhibitors tested have HDAC8 $IC_{50}$ values that are greater than 100 nM do not show isoform selectivity (less than 2 fold selectivity observed). This would indicate that compounds described herein would possess less toxicity due to the selective inhibition of HDAC8.

Example 17

Compound 23, is Selectively Cytotoxic to T-Cell Derived Tumor Cell Lines

The ability of HDAC8-selective inhibitor compounds described herein, e.g. compound 23, to reduce tumor cell proliferation in vitro was determined for several cell lines and peripheral blood mononuclear cells (PBMCs).

Figure 9A:
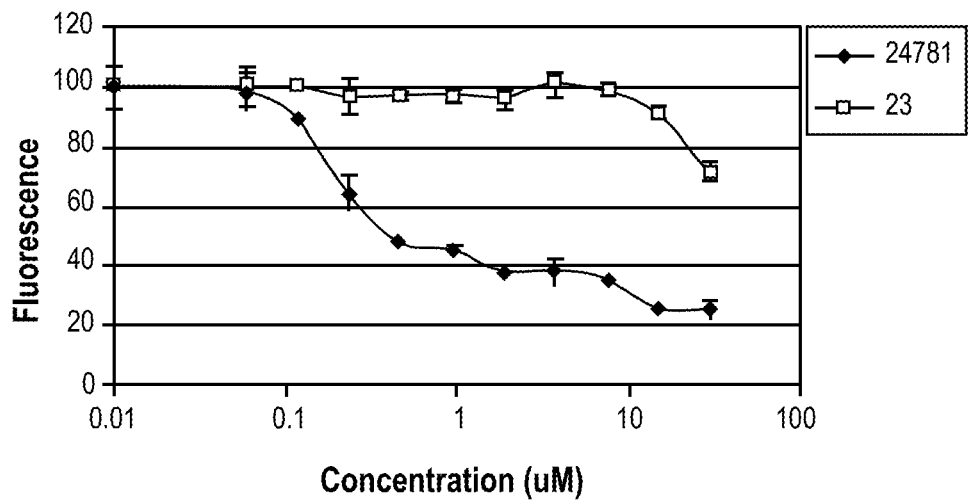
FIGS. 9A and B are illustrative panels of scatter plots showing the effect of the HDAC8-selective inhibitor compound, compound 23, on cell proliferation in the cell line HCT116 and in normal human peripheral blood mononuclear cells. Compound 23 does not inhibit growth of HCT116 or human PBMCs.
Figure 9B:
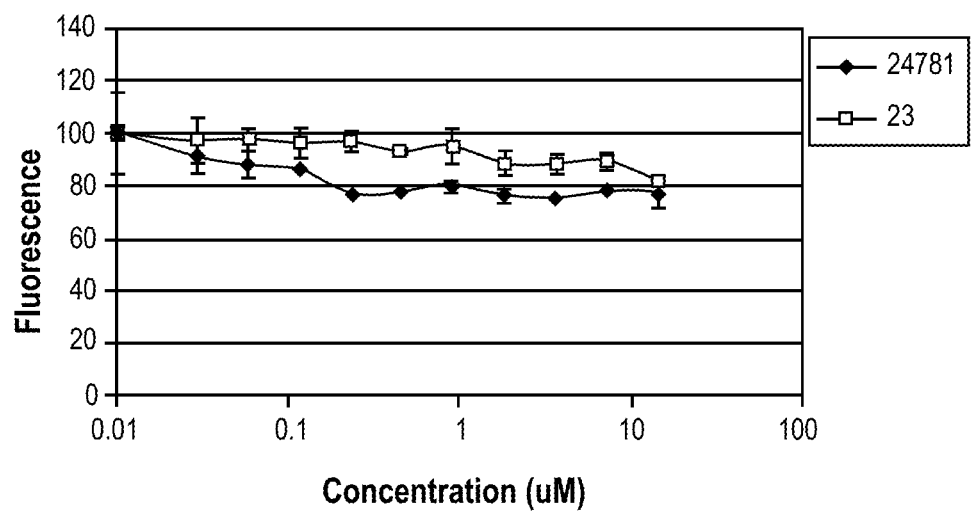
FIG. 9B: PBMCs, 24 hours, Alamar Blue assay.
Figure 10:
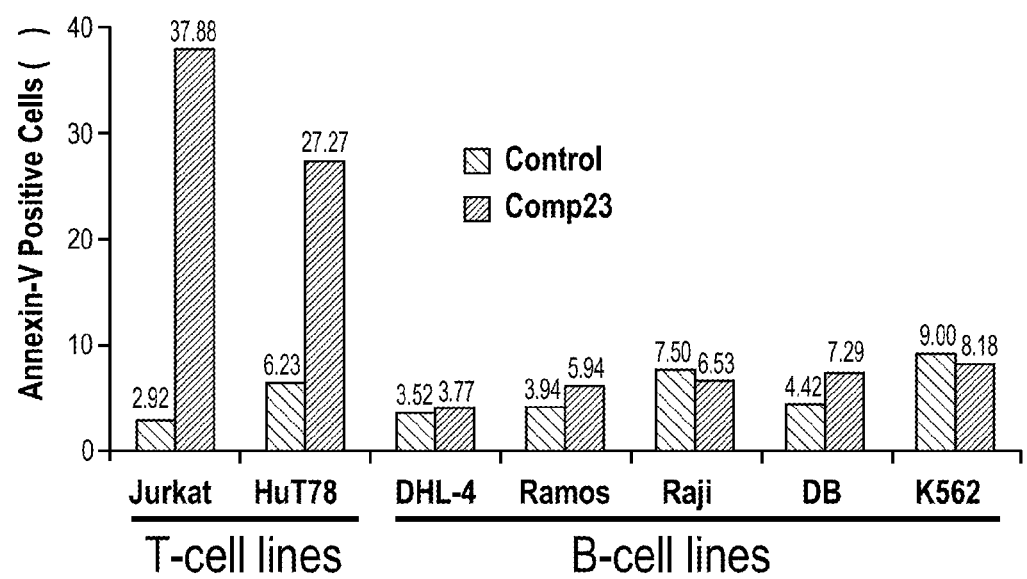
FIG. 10 is an illustrative scatter plot showing the effect of the HDAC8-selective inhibitor compound, compound 23, on cell proliferation in T-cell-derived and B-cell-derived cell lines. Compound 23 is cytotoxic to T-cell derived cells: Jurkat (GI50=3 uM) and HuT78 (GI50=4 uM). Compound 23 is not cytotoxic to B-cell derived cells: DB (GI50=20 uM) and K562 (GI50=20 uM); 8/8 solid tumor lines and human normal PBMCs (24 hours).
Figure 11:
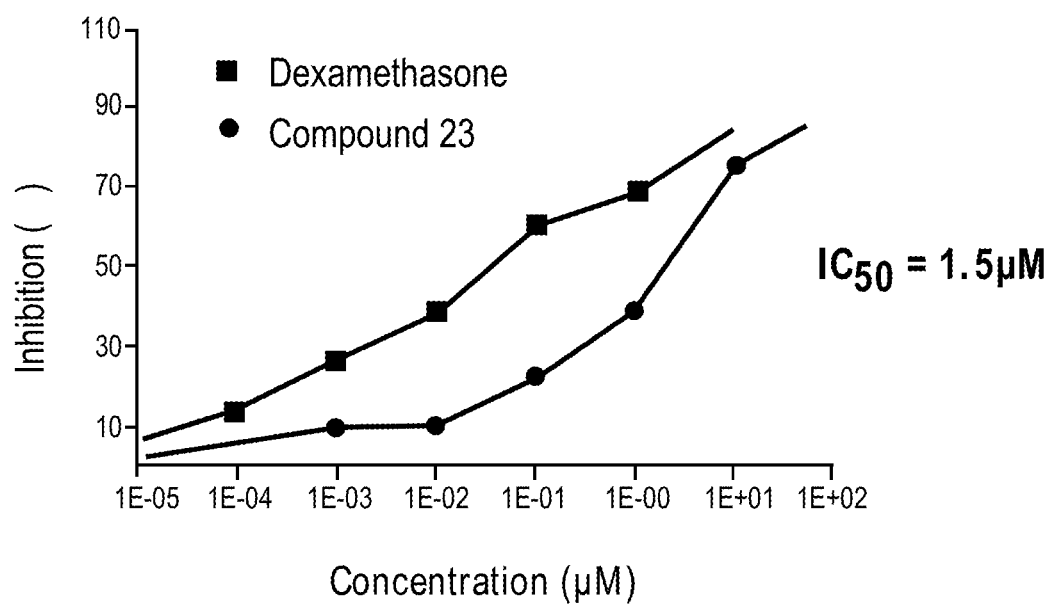
FIG. 11 shows inhibition of IL-1b secretion in human PBMCs resulting from HDAC8-selective inhibitor compound 23.
Figure 12:
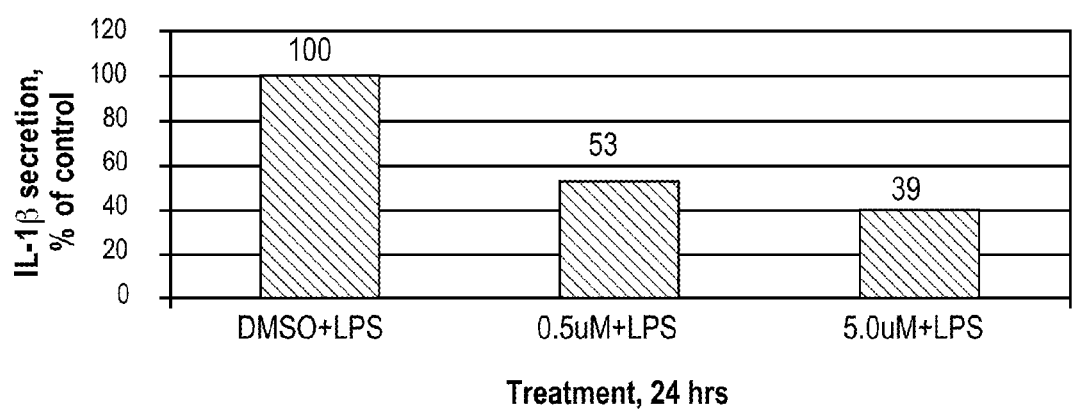
FIG. 12 shows reduction of IL-1b secretion in THP-1 monocyte cell line resulting from treatment with HDAC8-selective inhibitor compound 23 and LPS. Effects of LPS and compound 23 were normalized to DMSO and LPS control.
Figure 13:
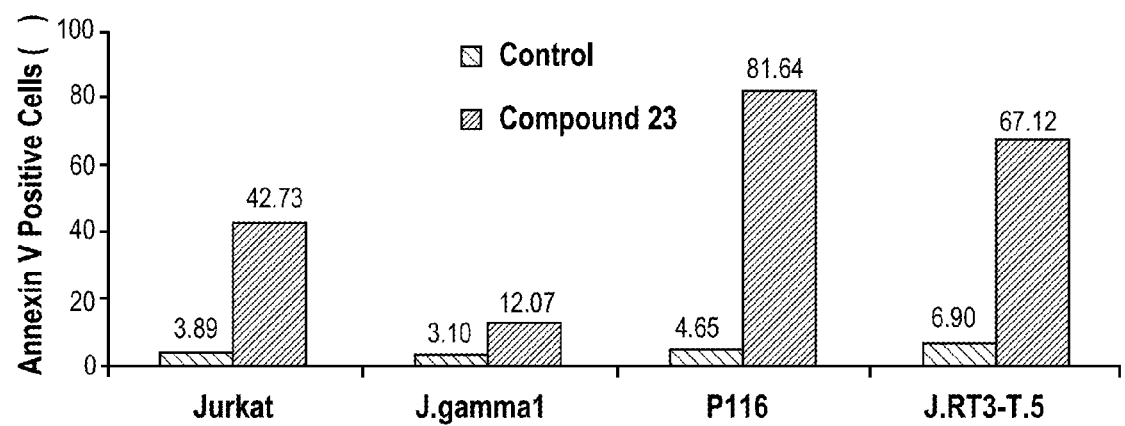
FIG. 13 shows that Phospholipase C-gamma 1-deficient Jurkat derivative J.gamma1 cells are resistant compound 23-induced apoptosis but TCR signaling mutants are not.

As shown in FIG. 8, compound 23, was relatively ineffective for inhibiting the growth of any of the H33HJ-JA1 (lymphoma), the OVCAR-3 (ovary), MIA-PaCa-2 (pancreas), or PANC-1 (pancreas) tumor cell lines, in comparison to the established anti-proliferative agent mitomycin. Likewise, Compound 23 failed to inhibit the growth of the HCT116 (human colon carcinoma) cell line or PBMCs (FIG. 9). In contrast, Compound 23 was cytotoxic to the Jurkat and HuT78 T-cell derived tumor cell lines, whereas the B-cell derived cell lines DB and K562 were not affected (FIG. 10). Based on these data, we conclude that the selective HDAC8 inhibitor compound effectively and specifically inhibits proliferation of T-cell tumor-cells.

siRNA protein knockdown experiments suggested that HDAC8 selective inhibitors would induce apoptosis or growth arrest in solid tumor cells. However, no cytotoxicity was observed in 8 tumor lines with the selective HDAC8 inhibitor compounds described herein (Table 5). The lack of concordance highlights the differences between protein knockdown by siRNA and selective active site enzyme inhibition with small molecules.

TABLE 5

Lack of cytotoxicity of compound 23 in solid tumor cells.

| Cell line | $GI_{50}$ (Alamar blue assay) | % apoptosis at 20 µM (Annexin V assay) |
|---|---|---|
| A549 (lung) | 19 µM | 0% |
| HCT116 (colon) | >20 µM | 3% |
| HeLa (cervix) | >20 µM | ND |
| U87 (glioma) | 17 µM | 0% |
| RKO (colon) | 14 µM | 0% |
| MCF-7 (breast) | >20 µM | 0% |
| PC3 (prostate) | >20 µM | 0% |
| Ovcar-3 (ovarian) | 6 µM | 15% |

$GI_{50}$ = concentration at which the growth of the tumor cells was inhibited by 50%.

The results of these experiments indicate that the selective HDAC8 inhibitors described herein would have better toxicity profiles and would be better tolerated than pan-HDAC inhibitors.

Example 18

Apoptosis in T-Cell Lines by Compound 23

As shown in FIG. 7. Phospholipase C-gamma 1-deficient Jurkat derivative J.gamma1 cells are resistant to compound 23-induced apoptosis but TCR signaling mutants are not Jurkat WT and derivative (see Table 6) cell lines were treated with 5 µM compound 23 for 2 days and Annexin-V positive cells measured by flow cytometry

TABLE 6

Effect of compound 23 on apoptosis in T-cell lines

| 3 Day dose T-Cell line | Compound 23 | | PCI-24781 | | Phenotype |
|---|---|---|---|---|---|
| | $GI_{50}$ (µM) | Apoptosis at 5 µM (%) | $GI_{50}$ (µM) | Apoptosis at 0.125 µM (%) | |
| Jurkat | 4.0 | 43 | 0.13 | 48 | Parent T-lymphocyte |
| J.γ1 | 4.0 | 12 | 0.14 | 18 | Phospholipase C-γ1 deficient |
| P116 | 10.2 | 82 | 0.19 | 76 | ZAP-70 deficient |
| J.RT3-T.5 | 5.1 | 67 | 0.14 | 32 | TCR-β chain deficient |

Figure 14:
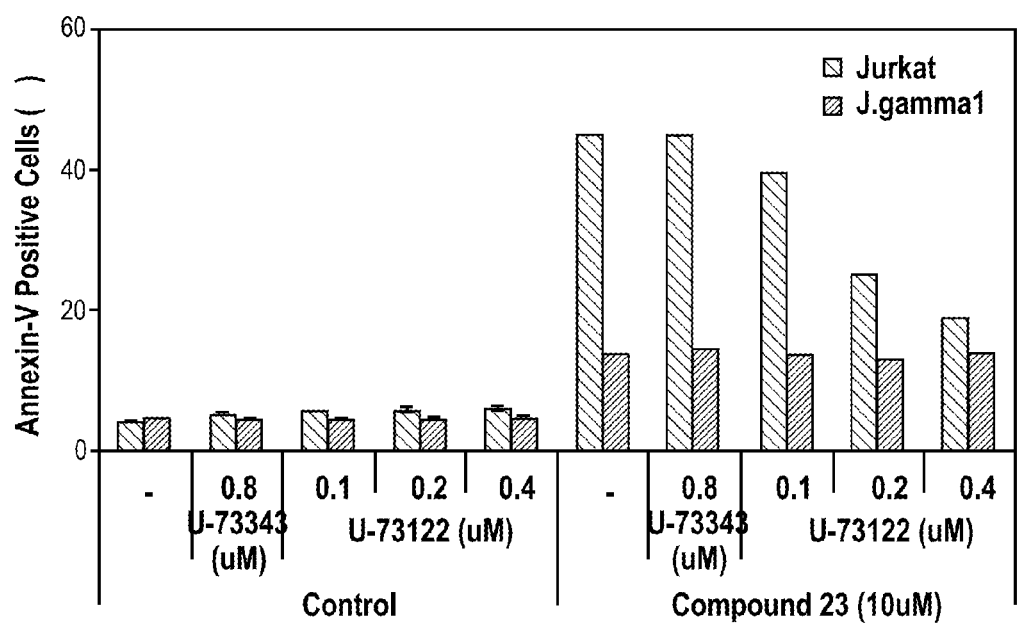
FIG. 14 shows that Phospholipase C inhibitor modulates selective HDAC8 inhibitor-induced apoptosis in Jurkat cells but does not affect PLCg1 deficient cells.

As shown in FIG. 14. Phospholipase C inhibitor modulates compound 23-induced apoptosis in Jurkat cells but does not affect PLCg1 deficient cells. Jurkat and J.gamma1 cells treated with PLC inhibitor U73122 and inactive analog U73343 with or without compound 23 and apoptosis measured after 2 days.

Figure 15:
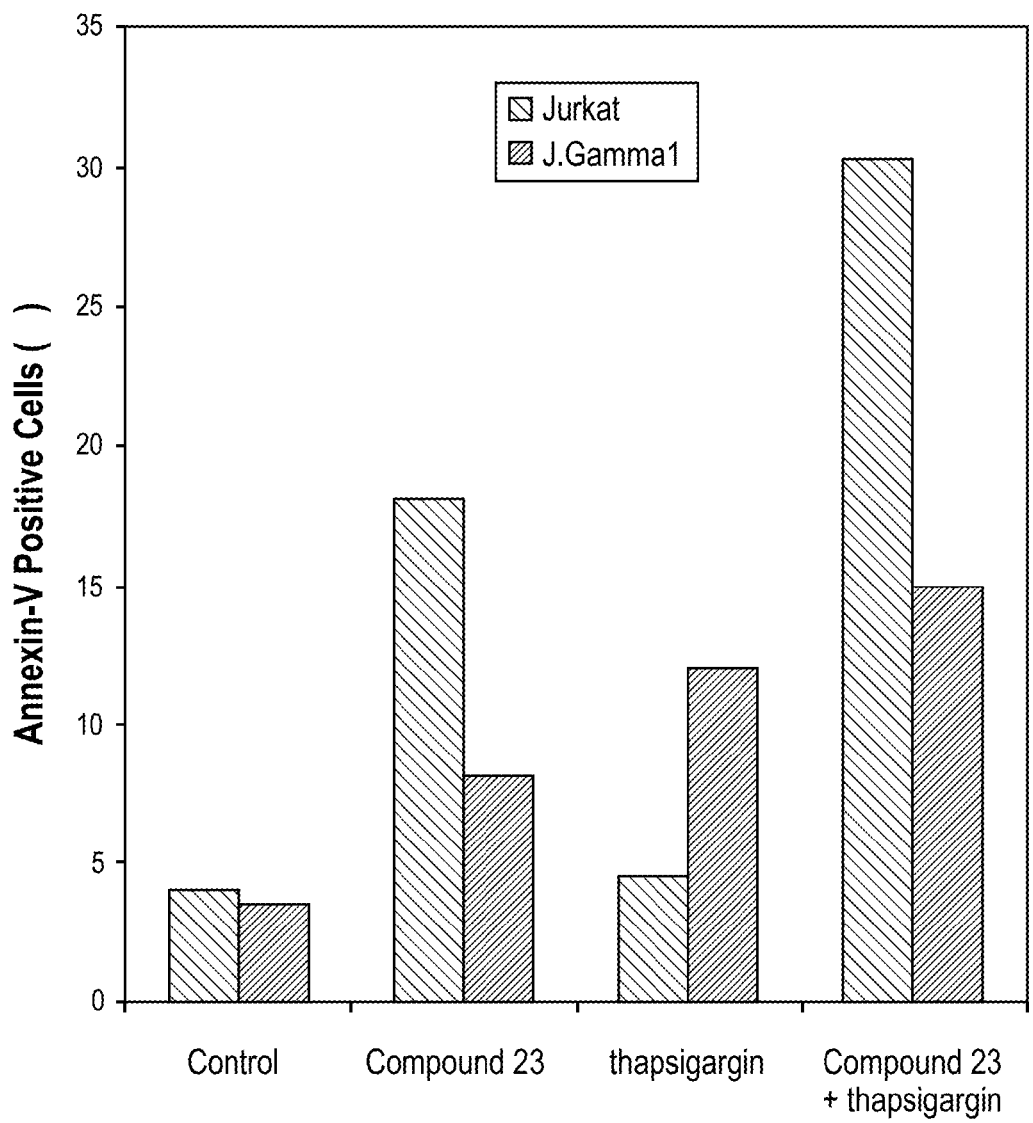
FIG. 15 shows that selective HDAC8 inhibitor-induced apoptosis is enhanced by Ca2+ effector thapsigargin in Jurkat cells but not in J.gamma1 cells

FIG. 15 show that compound 23 induced apoptosis is enhanced by Ca2+ effector thapsigargin in Jurkat cells but not in J.gamma1 cells. Jurkat and J-gamma1 cells were treated with compound 23, thapsigargin, BAPTA or the combinations. (compound 23=5 µM, thapsigargin=0.2 µM).

Figure 16:
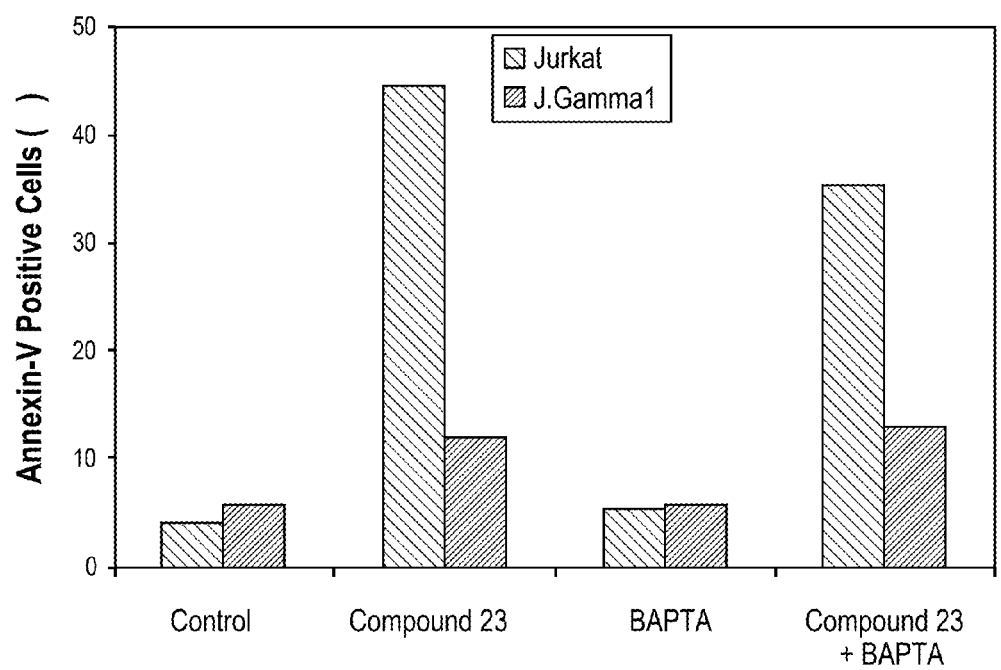
FIG. 16 shows that selective HDAC8 inhibitor-induced apoptosis is inhibited by Ca2+chelator BAPTA-AM in Jurkat cells but not in J.gamma1 cells.

FIG. 16 show that compound 23 induced apoptosis is inhibited by Ca2+chelator BAPTA-AM in Jurkat cells but not in J.gamma1 cells. Jurkat and J-gamma1 cells were treated with compound 23, BAPTA or the combinations. (compound 23=10 µM, BAPTA 0.5 µM).

Figure 17:
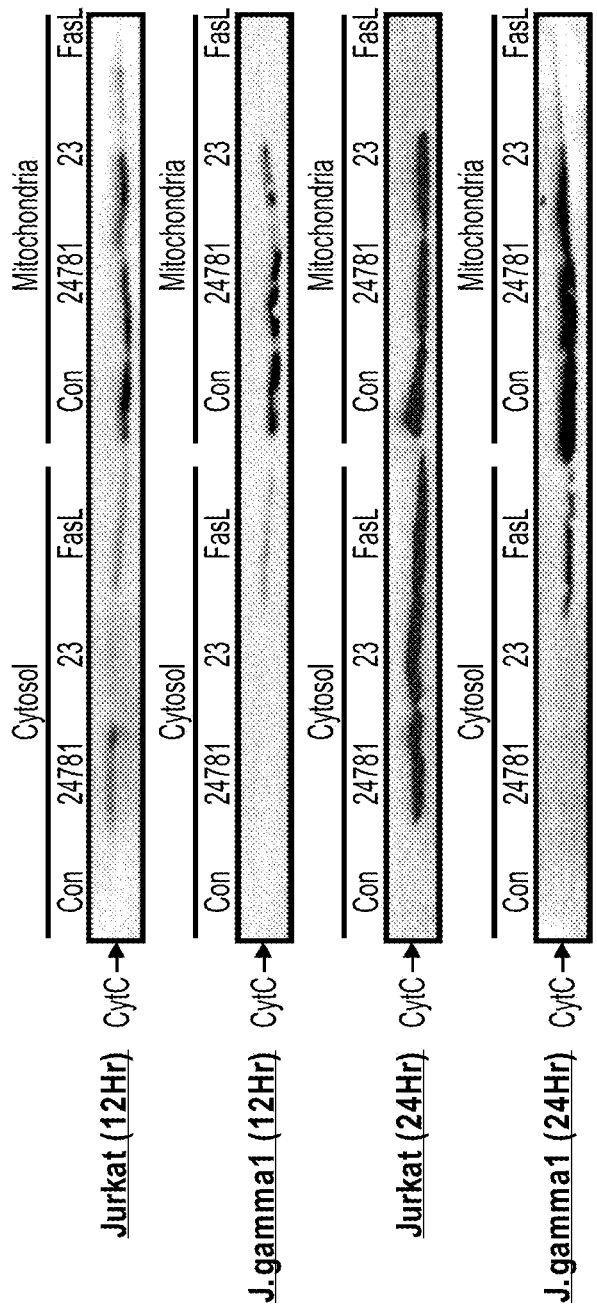
FIG. 17 shows that Cytochrome C translocation from mitochondria to cytosol following treatment with selective HDAC8 inhibitor compounds in Jurkat but not in J.gamma1 cells

As shown in FIG. 17. Cytochrome C translocation from mitochondria to cytosol following treatment with compound 23 in Jurkat but not in J.gamma1 cells. Jurkat and J-gamma1 cells were treated with compound 23, PCI 24781 or FasL for 12 or 24 hours, the mitochondrial and cytosolic (including ER) fractions separated using the Pierce Mitochondria Isolation kit and analyzed by Western blotting with anti-Cyt C (and anti-Cyt C oxidase, not shown).

Jurkat derivative J.gamma1 cell line (PLCg1 deficient) is resistant to apoptosis by compound 23 but T-cell receptor signaling mutants are not. PLCg1 appears to play a prominent role in selective HDAC8 inhibitor-induced apoptosis in Jurkat cells. Phospholipase inhibitor (but not inactive analog) blocks apoptosis by compound 23. Thapsigargin, a calcium release agent, enhances selective HDAC8 inhibitor-induced apoptosis in Jurkat cells while BAPTA, a calcium chelator, causes increased resistance. Cytochrome C release from mitochodria after treatment with compound 23 (likely due to Ca2+ influx) is blocked in J.gamma1 cells. Therefore Ca2+ release contributes at least partially to the apoptotic mechanism.

Example 19

Inhibition of IL-1b Secretion

Compounds described herein were examined for the ability to inhibit IL-1b secretion in human peripheral blood mononuclear cells (PMBCs) and THP-1 monocyte cells. (Experimental methods for measuring the effects of HDAC inhibitors on IL-1b secretion is discussed in Carta et al., *Blood*, 2006, vol. 108, no. 5, 1618-1626).

Test compound and/or vehicle is preincubated with human peripheral blood mononuclear leukocyte (PBML, 5×105/ml) cells in AIM-V medium pH 7.4 for 30 minutes at 37° C. Lipopolysaccharide (LPS, 25 ng/ml) is then added to stimulate the cells for another 16 hour incubation period in 5% $CO_2$. IL-1b cytokine levels in the conditioned medium are then quantitated using a sandwich ELISA kit. Compounds are screened at 10, 1, 0.1, 0.01 and 0.001 µM. These same concentrations are concurrently applied to a separate group of treated cells and evaluated for possible compound-induced cytotoxicity.

Compounds were also examined for effects on inhibition of IL-1b secretion in THP-1 monocyte cell lines. The results show that selective HDAC8 inhibitor compounds reduce IL-1b secretion. Thus, selective HDAC8 inhibitor compounds offer the opportunity for treatment of IL-1b mediated diseases or conditions with reduced toxicity (as compared to pan HDAC inhibitors).

Example 20

Pharmaceutical Compositions

Example 20a

Parenteral Composition

To prepare a parenteral pharmaceutical composition suitable for administration by injection, 100 mg of a water-soluble salt of a selective HDAC8 inhibitor compound described herein is dissolved in DMSO and then mixed with 10 mL of 0.9% sterile saline. The mixture is incorporated into a dosage unit form suitable for administration by injection.

In another embodiment, the following ingredients are mixed to form an injectable formulation.

| Ingredient | Amount |
| --- | --- |
| Selective HDAC8 inhibitor compound described herein | 1.2 g |
| sodium acetate buffer solution (0.4M) | 2.0 mL |
| HCl (1N) or NaOH (1M) | q.s. to suitable pH |
| water (distilled, sterile) | q.s. to 20 mL |

All of the above ingredients, except water, are combined and heated to 60-70° C. with stirring. A sufficient quantity of water at 60° C. is then added with vigorous stirring to emulsify the ingredients, and water then added q.s. to 100 g.

Example 20b

Oral Composition

To prepare a pharmaceutical composition for oral delivery, 100 mg of a selective HDAC8 inhibitor compound described herein is mixed with 750 mg of starch. The mixture is incorporated into an oral dosage unit for, such as a hard gelatin capsule, which is suitable for oral administration.

In another embodiment, the following ingredients are mixed intimately and pressed into single scored tablets.

| Ingredient | Quantity per tablet, mg |
| --- | --- |
| selective HDAC8 inhibitor compound described herein | 400 |
| Cornstarch | 50 |
| croscarmellose sodium | 25 |
| Lactose | 120 |
| magnesium stearate | 5 |

In yet another embodiment, the following ingredients are mixed intimately and loaded into a hard-shell gelatin capsule.

| Ingredient | Quantity per tablet, mg |
| --- | --- |
| selective HDAC8 inhibitor compound described herein | 200 |
| lactose, spray-dried | 148 |
| magnesium stearate | 2 |

In yet another embodiment, the following ingredients are mixed to form a suspension for oral administration.

| Ingredient | Amount |
| --- | --- |
| selective HDAC8 inhibitor compound described herein | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| Flavoring | 0.035 mL |
| Colorings | 0.5 mg |
| distilled water | q.s. to 100 mL |

Example 20c

Sublingual (Hard Lozenge) Composition

To prepare a pharmaceutical composition for buccal delivery, such as a hard lozenge, mix 100 mg of a selective HDAC8 inhibitor compound described herein with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 20d

Inhalation Composition

To prepare a pharmaceutical composition for inhalation delivery, 20 mg of a selective HDAC8 inhibitor compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

Example 20e

Rectal Gel Composition

To prepare a pharmaceutical composition for rectal delivery, 100 mg of a selective HDAC8 inhibitor compound described herein is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 20f

Suppository Formulation

A suppository of total weight 2.5 g is prepared by mixing a selective HDAC8 inhibitor compound described herein with Witepsol™ H-15 (triglycerides of saturated vegetable fatty acid; Riches-Nelson, Inc., New York), and has the following composition:

| Ingredient | Quantity per tablet, mg |
| --- | --- |
| selective HDAC8 inhibitor compound described herein | 500 |
| Witepsol ® H-15 | balance |

Example 20g

Topical Gel Composition

To prepare a pharmaceutical topical gel composition, 100 mg of a selective HDAC8 inhibitor compound described herein is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 20h

Ophthalmic Solution Composition

To prepare a pharmaceutical opthalmic solution composition, 100 mg of a selective HDAC8 inhibitor compound described herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

The examples and embodiments described herein are for illustrative purposes only and various modifications or changes suggested to persons skilled in the art are to be included within the spirit and purview of disclosure and scope of the appended claims. All publications, patents, and patent applications cited herein are hereby incorporated by reference for all purposes.

What is claimed is:

1. A compound of Formula Ia or IIa:

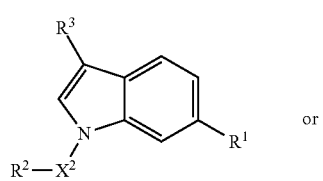

or

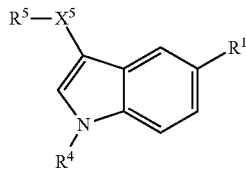

wherein:
$R^1$ is —C(O)NHOH;
$X^2$ is a bond, or alkylene; where the alkylene is optionally substituted with one, two, three, four, or five halo;
$R^2$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;
$R^3$ is hydrogen, alkyl, substituted alkyl, alkenyl, substituted alkenyl, hydroxy, alkoxy, or haloalkoxy;
$R^4$ is hydrogen, alkyl, substituted alkyl, alkenyl, substituted alkenyl, hydroxy, alkoxy, haloalkoxy, or optionally substituted phenyl;
$X^5$ is a bond, alkylene, or alkenylene where the alkylene or alkenylene is optionally substituted with halo; and
$R^5$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;
or a pharmaceutically acceptable salt thereof.

2. The compound, or a pharmaceutically acceptable salt thereof, of claim 1, wherein:
$X^2$ is a bond.

3. The compound, or a pharmaceutically acceptable salt thereof, of claim 1, wherein:
$X^2$ is alkylene.

4. The compound, or a pharmaceutically acceptable salt thereof, of claim 1, wherein:
$X^2$ is —$CH_2$—, —$CH_2CH_2$—, —$CH(CH_3)$—, or —$(CH_2)_3$—.

5. The compound, or a pharmaceutically acceptable salt thereof, of claim 1, wherein:
$X^2$ is —$CH_2$—.

6. The compound, or a pharmaceutically acceptable salt thereof, of claim 1, wherein:
$R^2$ is aryl where the aryl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro.

7. The compound, or a pharmaceutically acceptable salt thereof, of claim 1, wherein:
$R^2$ is cyclohexyl, benzo[2,1,3]oxadiazol-5-yl, phenyl, naphth-2-yl, 2-methylphenyl, 3-methylphenyl, 4-methylphenyl, 3-methoxyphenyl, 4-methoxyphenyl, 3,5-dimethoxyphenyl, 3,4,5-trimethoxyphenyl, 2-chlorophenyl, 3-chlorophenyl, 4-chlorophenyl, 3,4-dichlorophenyl, 2-fluorophenyl, 3-fluorophenyl, 4-fluorophenyl, 4-(difluoromethoxy)-phenyl, 4-(trifluoromethoxy)-phenyl, 3-fluoro-4-methoxy-phenyl, piperidin-4-yl, or N-(t-butoxycarbonyl)piperidin-4-yl.

8. The compound, or a pharmaceutically acceptable salt thereof, of claim 1, wherein:
$R^3$ is hydrogen, alkyl, or substituted alkyl.

9. The compound, or a pharmaceutically acceptable salt thereof, of claim 1, wherein:
$R^3$ is hydrogen.

10. The compound, or a pharmaceutically acceptable salt thereof, of claim 1, wherein:
$R^4$ is alkyl or optionally substituted phenyl.

11. The compound, or a pharmaceutically acceptable salt thereof, of claim 1, wherein:
$X^5$ is alkylene.

12. The compound, or a pharmaceutically acceptable salt thereof, of claim 1, wherein:
$R^5$ is phenyl optionally substituted with one, two, or three acylamino, amino, halo, or nitro.

13. The compound, or a pharmaceutically acceptable salt thereof, of claim 1, wherein:
$R^5$ is 4-(t-butoxycarbonyl)piperazin-1-yl, phenyl, 4-aminophenyl, 4-(phenylcarbonylamino)-phenyl, 4-fluorophenyl, or 4-nitrophenyl.

14. The compound, or a pharmaceutically acceptable salt thereof, of claim 1, wherein:
$R^3$ is hydrogen;
$X^2$ is alkylene; and
$R^2$ is aryl, cycloalkyl, heteroaryl, or heterocycloalkyl where the aryl, cycloalkyl, heteroaryl, and heterocycloalkyl are optionally substituted with one, two, or three alkyl, alkoxy, halo, or haloalkoxy.

15. The compound, or a pharmaceutically acceptable salt thereof, of claim 1, wherein:
$R^3$ is hydrogen;
$X^2$ is —CH$_2$—; and
$R^2$ is aryl, cycloalkyl, heteroaryl, or heterocycloalkyl, where the aryl, cycloalkyl, heteroaryl, and heterocycloalkyl are optionally substituted with one, two, or three alkyl, alkoxy, halo, or haloalkoxy.

16. The compound, or a pharmaceutically acceptable salt thereof, of claim 1, wherein:
$R^3$ is hydrogen;
$X^2$ is —CH$_2$—; and
$R^2$ is aryl where the aryl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro.

17. The compound, or a pharmaceutically acceptable salt thereof, of claim 1, wherein:
$R^3$ is hydrogen;
$X^2$ is —CH$_2$—; and
$R^2$ is cyclohexyl, benzo[2,1,3]oxadiazol-5-yl, phenyl, naphth-2-yl, 2-methylphenyl, 3-methylphenyl, 4-methylphenyl, 3-methoxyphenyl, 4-methoxyphenyl, 3,5-dimethoxyphenyl, 3,4,5-trimethoxyphenyl, 2-chlorophenyl, 3-chlorophenyl, 4-chlorophenyl, 3,4-dichlorophenyl, 2-fluorophenyl, 3-fluorophenyl, 4-fluorophenyl, 4-(difluoromethoxy)-phenyl, 4-(trifluoromethoxy)-phenyl, 3-fluoro-4-methoxy-phenyl, piperidin-4-yl, or N-(t-butoxycarbonyl)piperidin-4-yl.

18. The compound of claim 1, wherein the compound is:
1-(3,4-dichloro-phenylmethyl)-1H-indole-6-carboxylic acid hydroxyamide;
1-(2-methyl-phenylmethyl)-1H-indole-6-carboxylic acid hydroxyamide;
1-(3,4,5-trimethoxy-phenylmethyl)-1H-indole-6-carboxylic acid hydroxyamide;
1-(3-fluoro-phenylmethyl)-1H-indole-6-carboxylic acid hydroxyamide;
1-(3-methyl-phenylmethyl)-1H-indole-6-carboxylic acid hydroxyamide;
1-(benzyl)-1H-indole-6-carboxylic acid hydroxyamide;
1-(3,5-dimethoxy-phenylmethyl)-1H-indole-6-carboxylic acid hydroxyamide;
1-(1-methyl-1-phenylmethyl)-1H-indole-6-carboxylic acid hydroxyamide;
1-(4-fluoro-phenylmethyl)-1H-indole-6-carboxylic acid hydroxyamide;
1-(2-fluoro-phenylmethyl)-1H-indole-6-carboxylic acid hydroxyamide;
1-(2-chloro-phenylmethyl)-1H-indole-6-carboxylic acid hydroxyamide;
1-(3-methoxy-phenylmethyl)-1H-indole-6-carboxylic acid hydroxyamide;
1-(naphth-2-ylmethyl)-1H-indole-6-carboxylic acid hydroxyamide;
1-(3-phenylpropyl)-1H-indole-6-carboxylic acid hydroxyamide;
1-(cyclohexylmethyl)-1H-indole-6-carboxylic acid hydroxyamide;
1-[4-(trifluoromethoxy)-phenylmethyl]-1H-indole-6-carboxylic acid hydroxyamide;
1-(4-chloro-phenylmethyl)-1H-indole-6-carboxylic acid hydroxyamide;
1-(benzo[2,1,3]oxadiazol-5-ylmethyl)-1H-indole-6-carboxylic acid hydroxyamide;
1-(4-methyl-phenylmethyl)-1H-indole-6-carboxylic acid hydroxyamide;
1-(3-fluoro-4-methoxy-phenylmethyl)-1H-indole-6-carboxylic acid hydroxyamide;
1-[4-(difluoromethoxy)-phenylmethyl]-1H-indole-6-carboxylic acid hydroxyamide;
1-(4-methoxy-phenylmethyl)-1H-indole-6-carboxylic acid hydroxyamide;
1-(phenethyl)-1H-indole-6-carboxylic acid hydroxyamide;
1-(3-chloro-phenylmethyl)-1H-indole-6-carboxylic acid hydroxyamide;
1-[N-(t-butoxycarbonyl)piperidin-4-ylmethyl]-1H-indole-6-carboxylic acid hydroxyamide; or
1-(piperidin-4-ylmethyl)-1H-indole-6-carboxylic acid hydroxyamide;
or a pharmaceutically acceptable salt thereof.

19. The compound of claim 1, wherein the compound is:
1-methyl-3-(4-nitro-phenylmethyl)-1H-indole-5-carboxylic acid hydroxyamide;
1-ethyl-3-(phenylmethyl)-1H-indole-5-carboxylic acid hydroxyamide;
1-methyl-3-[4-(phenylcarbonylamino)-phenylmethyl]-1H-indole-5-carboxylic acid hydroxyamide;
1-isopropyl-3-(phenylmethyl)-1H-indole-5-carboxylic acid hydroxyamide;
1-methyl-3-(4-amino-phenylmethyl)-1H-indole-5-carboxylic acid hydroxyamide;

1-methyl-3-(4-fluoro-phenylmethyl)-1H-indole-5-carboxylic acid hydroxyamide;
1-phenyl-3-(phenylmethyl)-1H-indole-5-carboxylic acid hydroxyamide; or
1-methyl-3-[4-(t-butoxycarbonyl)piperazin-1-ylmethyl]-1H-indole-5-carboxylic acid hydroxyamide;
or a pharmaceutically acceptable salt thereof.

20. The compound of claim 1, wherein the compound is 1-(4-methoxy-phenylmethyl)-1H-indole-6-carboxylic acid hydroxyamide; or a pharmaceutically acceptable salt thereof.

21. A pharmaceutical composition comprising a therapeutically effective amount of a compound of claim 1, or a pharmaceutically acceptable salt thereof, and a pharmaceutically acceptable excipient.

* * * * *